(12) United States Patent
Eto et al.

(10) Patent No.: US 9,706,933 B2
(45) Date of Patent: Jul. 18, 2017

(54) BLOOD PRESSURE MEASUREMENT DEVICE

(75) Inventors: Mika Eto, Takatsuki (JP); Yukiya Sawanoi, Nara (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 703 days.

(21) Appl. No.: 12/993,216

(22) PCT Filed: May 21, 2009

(86) PCT No.: PCT/JP2009/059358
§ 371 (c)(1),
(2), (4) Date: Feb. 3, 2011

(87) PCT Pub. No.: WO2009/142266
PCT Pub. Date: Nov. 26, 2009

(65) Prior Publication Data
US 2011/0125035 A1 May 26, 2011

(30) Foreign Application Priority Data

May 22, 2008 (JP) ................................ 2008-134541
May 22, 2008 (JP) ................................ 2008-134542
May 22, 2008 (JP) ................................ 2008-134543

(51) Int. Cl.
*A61B 5/02* (2006.01)
*A61B 5/0225* (2006.01)
*A61B 5/022* (2006.01)

(52) U.S. Cl.
CPC ........ *A61B 5/0225* (2013.01); *A61B 5/02225* (2013.01)

(58) Field of Classification Search
USPC ................................................. 600/485–515
See application file for complete search history.

(56) References Cited

U.S. PATENT DOCUMENTS 5,038,790 A * 8/1991 Malkamaki .................... 600/490
5,156,158 A * 10/1992 Shirasaki ....................... 600/493
(Continued)

FOREIGN PATENT DOCUMENTS

JP    63-35230    *  2/1988
JP    63-145636 A    6/1988
(Continued)

OTHER PUBLICATIONS

Office Action for Russian Application No. 2010151962/14 dated Apr. 26, 2013, with English translation thereof (7 pages).
(Continued)

*Primary Examiner* — Michael Kahelin
*Assistant Examiner* — Mitchell E Alter
(74) *Attorney, Agent, or Firm* — Osha Liang LLP

(57) ABSTRACT

In a sphygmomanometer, a value representing a perimeter of a measuring portion is obtained. A parameter for controlling a drive voltage of a pump is determined based on the value. The drive voltage is determined based on the parameter and an internal pressure of a fluid bladder to pressurize the fluid bladder. In pressurizing process, a diastolic blood pressure value is calculated. A systolic blood pressure value is estimated, and when the internal pressure of the fluid bladder reaches the pressure, the pressurizing is stopped. A gap of a valve for discharging the fluid from the fluid bladder is determined based on a perimeter of a measuring portion, and the fluid bladder is depressurized with the gap constant. In the depressurizing process, the systolic blood pressure value is calculated. When the systolic blood pressure value is calculated, the fluid is discharged from the fluid bladder, and the measurement is terminated.

6 Claims, 44 Drawing Sheets

(56) References Cited

U.S. PATENT DOCUMENTS

| | | | |
|---|---|---|---|
| 5,178,152 A * | 1/1993 | Ozawa | A61B 5/02208 600/493 |
| 6,322,517 B1 * | 11/2001 | Yamamoto et al. | 600/494 |
| 6,602,200 B1 * | 8/2003 | Kubo | A61B 5/0225 600/485 |
| 2004/0127801 A1 * | 7/2004 | Takahashi et al. | 600/485 |
| 2007/0239042 A1 * | 10/2007 | Takahashi | F16K 31/0682 600/498 |
| 2008/0312544 A1 * | 12/2008 | Mochizuki | 600/492 |
| 2009/0312651 A1 * | 12/2009 | Sano et al. | 600/493 |
| 2009/0312652 A1 * | 12/2009 | Yamakoshi et al. | 600/493 |

FOREIGN PATENT DOCUMENTS

| | | |
|---|---|---|
| JP | 64-040030 A | 2/1989 |
| JP | 3-121045 A | 5/1991 |
| JP | 4-250133 A | 9/1992 |
| JP | 5-329113 A | 12/1993 |
| JP | 6-047011 A | 2/1994 |
| JP | 6-245911 A | 9/1994 |
| JP | 7-313473 A | 12/1995 |
| JP | 10-314132 A | 12/1998 |
| JP | 3149873 B2 | 1/2001 |
| JP | 2001-70263 A | 3/2001 |
| JP | 2006-288531 A | 10/2006 |
| JP | 2007-167171 A | 7/2007 |
| WO | 01/17427 A1 | 3/2001 |

OTHER PUBLICATIONS

Patent Abstracts of Japan, Publication No. 06-245911, dated Sep. 6, 1994, 1 page.
Patent Abstracts of Japan, Publication No. 05-329113, dated Dec. 14, 1993, 1 page.
Patent Abstracts of Japan, Publication No. 04-250133, dated Sep. 7, 1992, 1 page.
Patent Abstracts of Japan, Publication No. 03-121045, dated May 23, 1991, 1 page.
Patent Abstracts of Japan, Publication No. 64-040030, dated Feb. 10, 1989, 1 page.
Patent Abstracts of Japan, Publication No. 07-313473, dated Dec. 5, 1995, 1 page.
Patent Abstracts of Japan, Publication No. 10-314132, dated Dec. 2, 1998, 1 page.
Patent Abstracts of Japan, Publication No. 2006-288531, dated Oct. 26, 2006, 1 page.
Patent Abstracts of Japan, Publication No. 06-047011, dated Feb. 22, 1994, 1 page.
International Search Report issued in PCT/JP2009/059358, mailed on Jun. 16, 2009, with translation, 7 pages.
Patent Abstracts of Japan, Publication No. 2001-070263, dated Mar. 21, 2001, 1 page.

* cited by examiner

Depressurizing rate [mmHg/sec]

The amount of discharge of fluid [ml/sec]

Pressurized pulse wave amplitude with respect to constant volume change [mmHg]

Depressurizing rate [mmHg/sec]

The amount of discharge of fluid [ml/sec]

- - - Measurement portion is thin
— · — Measurement portion is thick

Pressurized pulse wave amplitude with respect to constant volume change [mmHg]

- - - Measurement portion is thin
— · — Measurement portion is thick

BLOOD PRESSURE MEASUREMENT DEVICE

TECHNICAL FIELD

This invention relates to a blood pressure measurement device, and more particularly to a blood pressure measurement device for measuring blood pressure using a cuff including a fluid bladder.

BACKGROUND ART

An example of blood pressure calculation method used by an electronic sphygmomanometer is an oscillometric method. In the oscillometric method, a cuff including a fluid bladder wrapped around a portion of a living body is pressurized and depressurized. A volume change of the fluid bladder transmitted by a volume change of a pressurized blood vessel is recognized as a pressure change of the fluid bladder (pressurized pulse wave amplitude), and thereby a blood pressure is calculated.

The fluid bladder has such property that the pressure of the fluid bladder and the volume of the fluid bladder have a relationship as shown in FIG. 33. More specifically, the description will be made with reference to FIG. 33. In a region in which the pressure of the fluid bladder is low as shown in portion A, the volume of the fluid bladder rapidly increases in response to an increase of the volume of the fluid bladder. On the other hand, as shown in portion B, as the pressure of the fluid bladder increases, an increasing rate of the volume of the fluid bladder in response to an increase of the pressure of the fluid bladder gradually decreases.

An electronic sphygmomanometer for measuring a blood pressure during depressurizing process of a fluid bladder will be described. At this occasion, FIG. 34 illustrates a case where a fluid density in a fluid bladder is low, and FIG. 35 illustrates a case where a fluid density in a fluid bladder is high. More specifically, FIGS. 34 and 35 illustrate a volume change of the fluid bladder (portion (B)), a change of a fluid density in the fluid bladder (portion (C)), and a pressure change of the fluid bladder (portion (D)) according to a volume change of a blood vessel (portion (A)). Further, FIG. 36 illustrates a case where a discharge rate of the fluid discharged from the fluid bladder is fast, namely, the amount of discharge per unit time is large, and FIG. 37 illustrates a case where a discharge rate of the fluid discharged from the fluid bladder is slow, namely, the amount of discharge per unit time is small. More specifically, FIGS. 36 and 37 illustrate a volume change of the fluid bladder (portion (B)) and a pressure change of the fluid bladder (portion (C)) according to a volume change of a blood vessel (portion (A)).

It is understood from FIGS. 34 to 37 that the electronic sphygmomanometer for measuring the blood pressure during depressurizing process of the fluid bladder has the following features in detection accuracy of a volume change of the blood vessel.

(1) As the pressure of the fluid bladder is higher, the density of the fluid in the fluid bladder is higher.

(2) As the volume of the fluid bladder is larger, a density change of the fluid in the fluid bladder caused by a volume change of the blood vessel is smaller. Accordingly, detection accuracy of the volume change of the blood vessel is low.

(3) In a case where the volume change of the fluid bladder is the same, detection accuracy changes as follows. As the pressure of the fluid bladder is higher, a density change of the fluid in the fluid bladder caused by the volume change of the fluid bladder is larger, and accordingly detection accuracy of the volume change of the blood vessel is high.

(4) Even when the pressure of the fluid bladder is the same, a magnitude of the volume change of the fluid bladder caused by a volume change of the blood vessel changes according to the amount of discharge of the fluid in the fluid bladder. Accordingly, detection accuracy of the volume change of the blood vessel is different.

(5) As the amount of discharge of the fluid in the fluid bladder is larger, the volume change of the fluid bladder caused by the volume change of the blood vessel is smaller. Accordingly, the detection accuracy of the volume change of the blood vessel becomes low.

Therefore, in the electronic sphygmomanometer for using the oscillometric method to measure the blood pressure during depressurizing process of the fluid bladder, the detection accuracy of the volume change of the blood vessel relies on the density of the fluid in the fluid bladder and the amount of discharge of the fluid discharged from the fluid bladder.

In the electronic sphygmomanometer for reducing the pressure of the fluid bladder at a constant rate and measuring the blood pressure during depressurizing process, the pressure is reduced at a constant rate as shown in FIG. 38A. Therefore, the amount of fluid discharged from the fluid bladder is controlled by a valve according to the pressure of the fluid bladder and a perimeter of a measurement portion as shown in FIG. 38B. As a result, as shown in FIG. 38C, in a region in which the pressure of the fluid bladder is high, a pressurized pulse wave amplitude with respect to a constant volume change of the blood vessel is large, and in a region in which the pressure of the fluid bladder is low, a pressurized pulse wave amplitude with respect to a constant volume change of the blood vessel is small. On the other hand, the amount of change of the volume change of the blood vessel caused by the pressure change of the fluid bladder is different according to a perimeter of a measurement portion. Therefore, these are the causes of errors in blood pressure measurement.

Subsequently, an electronic sphygmomanometer for measuring a blood pressure during pressurizing process of a fluid bladder will be described. At this occasion, FIG. 39 illustrates a case where a fluid density in a fluid bladder is low, and FIG. 40 illustrates a case where a fluid density in a fluid bladder is high. More specifically, FIGS. 39 and 40 illustrate a volume change of the fluid bladder (portion (B)), a change of a fluid density in the fluid bladder (portion (C)), and a pressure change of the fluid bladder (portion (D)) according to a volume change of a blood vessel (portion (A)). Further, FIG. 41 illustrates a case where an inflow of a fluid into a fluid bladder is fast, i.e., the amount of inflow per unit time is large, and FIG. 42 illustrates a case where an inflow of a fluid into a fluid bladder is slow, i.e., the amount of inflow per unit time is small. More specifically, FIGS. 41 and 42 illustrate a volume change of the fluid bladder (portion (B)) and a pressure change of the fluid bladder (portion (C)) according to a volume change of a blood vessel (portion (A)).

It is understood from FIGS. 39 to 42 that the electronic sphygmomanometer for measuring the blood pressure during pressurizing process of the fluid bladder has the following features in detection accuracy of a volume change of the blood vessel.

(1) As the pressure of the fluid bladder is higher, the fluid density in the fluid bladder is higher.

(2) As the volume of the fluid bladder is larger, a change of a fluid density in the fluid bladder caused by a volume change of the fluid bladder is smaller. Accordingly, detection accuracy of the volume change of the blood vessel is low.

(3) In a case where the volume change of the fluid bladder is the same, detection accuracy changes as follows. As the pressure of the fluid bladder is higher, a fluid density change in the fluid bladder caused by the volume change of the fluid bladder is larger, and accordingly detection accuracy of the volume change of the blood vessel is high.

(4) Even when the pressure of the fluid bladder is the same, a magnitude of the volume change of the fluid bladder caused by a volume change of the blood vessel changes according to the amount of inflow of the fluid in the fluid bladder. Accordingly, detection accuracy of the volume change of the blood vessel is different.

(5) As the amount of inflow of the fluid into the fluid bladder is larger, the volume change of the fluid bladder caused by the volume change of the blood vessel is smaller. Accordingly, the detection accuracy of the volume change of the blood vessel becomes low.

Therefore, in the electronic sphygmomanometer for using the oscillometric method to measure the blood pressure during pressurizing process of the fluid bladder, the detection accuracy of the volume change of the blood vessel relies on the density of the fluid in the fluid bladder and the amount of inflow of the fluid into the fluid bladder.

In the electronic sphygmomanometer for increasing the pressure of the fluid bladder at a constant rate and measuring the blood pressure during pressurizing process, the pressure is increased at a constant rate as shown in FIG. 43A. Therefore, the amount of fluid flowing into the fluid bladder is controlled by a pump according to the pressurizing rate of the fluid bladder and a perimeter of a measurement portion. At this occasion, the amount of fluid flowing into the fluid bladder changes according to the pressure of the fluid bladder and the perimeter of the measurement portion as shown in FIG. 43B. As a result, as shown in FIG. 43C, in a region in which the pressure of the fluid bladder is high, a pressurized pulse wave amplitude with respect to a volume change of the blood vessel is large, and in a region in which the pressure of the fluid bladder is low, a pressurized pulse wave amplitude with respect to a constant volume change of the blood vessel is small. On the other hand, the amount of change of the pressurized pulse wave amplitude caused by the pressure change of the fluid bladder is different according to the perimeter of the measurement portion. Therefore, these are the causes of errors in blood pressure measurement.

In an electronic sphygmomanometer for pressurizing a fluid bladder by keeping a constant drive voltage of a pump for pressurizing the fluid bladder, the pressurizing rate of the fluid bladder changes according to the pressure of the fluid bladder and a perimeter of a measurement portion as shown in FIG. 44A. In addition, as shown in FIG. 44B, the amount of fluid flowing into the fluid bladder changes according to the pressure of the fluid bladder. As a result, as shown in FIG. 44C, in a region in which the pressure of the fluid bladder is high, a pressurized pulse wave amplitude with respect to a constant volume change of the blood vessel is large, and in a region in which the pressure of the fluid bladder is low, a pressurized pulse wave amplitude with respect to a constant volume change of the blood vessel is small. On the other hand, the amount of change of the volume change of the blood vessel caused by the pressure change of the fluid bladder is different according to a perimeter of a measurement portion. Therefore, these are the causes of errors in blood pressure measurement.

Japanese Unexamined Patent Publication No. H6-245911 (hereinafter, Document 1) discloses a technique for adjusting the amount of discharge of a valve according to a perimeter of a measurement portion or a technique using a fluid storage unit in communication with a fluid bladder and performing control for keeping a constant summation of volumes of the fluid bladder and the fluid storage unit according to a winding perimeter of the fluid bladder to a measurement portion. Therefore, even when the perimeter of the measurement portion is different, the depressurizing rate is kept constant.

Further, Japanese Unexamined Patent Publication No. H5-329113 (hereinafter, Document 2) discloses a method previously arranging a volume change property of a fluid bladder with respect to a pressure of the fluid bladder, converting a signal of the pressure change of the fluid bladder into a volume change, and measuring a blood pressure value using the volume change.

Further, Japanese Unexamined Patent Publication No. H4-250133 (hereinafter, Document 3) discloses a method for closing a valve for discharging a fluid in a fluid bladder in a pulse wave appearance period to prevent attenuation of a volume change of a blood vessel caused by a volume change of the fluid bladder.

Patent Document 1: Japanese Unexamined Patent Publication No. H6-245911

Patent Document 2: Japanese Unexamined Patent Publication No. H5-329113

Patent Document 3: Japanese Unexamined Patent Publication No. H4-250133

SUMMARY OF THE INVENTION

However, in the method disclosed in document 1, a difference of a depressurizing rate caused by a difference of the perimeter of the measurement portion can be eliminated, but the amount of discharge of the valve changes in synchronization with the pressure of the fluid bladder in order to maintain the depressurizing rate at a constant rate, and therefore, a pressurized pulse wave amplitude changes according to the pressure of the fluid bladder. Therefore, even when a summation of volumes of the fluid bladder and the fluid storage unit is controlled to be constant, only a difference of the volume caused by the perimeter of the measurement portion is eliminated, and a magnitude of a pressure change of the fluid bladder with respect to a volume change of the blood vessel changes according to the pressure of the fluid bladder. Therefore, an error occurs in blood pressure measurement.

On the other hand, in the method disclosed in the document 2, it is necessary previously give the pressure of the fluid bladder and volume change character. However, this change character unlimitedly changes according to a wrapping method of the fluid bladder, a thickness of an arm, softness of a human body, and the like, and sufficient correction cannot be performed. Further, it is necessary to perform multiple, more complicated corrections (flow amount detection, size detection of a measurement portion, wrapping condition detection, detection of softness of a human body, and the like), and a complicated apparatus is needed. Therefore, this is not practical.

Further, in the method disclosed in document 3, the volume change of the blood vessel can be correctly recognized as the pressure change of the fluid bladder. However, it is difficult to reduce the pressure in order to close the valve every time a pulse wave appears.

In other words, in these methods disclosed in the above documents, the pressure and the volume of the fluid bladder is not in proportional relationship. Therefore, when the blood pressure measurement is performed while the pressure is reduced, the flow amount of the fluid discharged from the fluid bladder is different according to the perimeter of the measurement portion and the pressure of the fluid bladder. On the other hand, when the blood pressure measurement is performed while the pressure is increased, the amount of inflow of the fluid into the fluid bladder is different according to the perimeter of the measurement and the pressure of the fluid bladder. Therefore, the detection accuracy of the pressurized pulse wave amplitude with respect to the volume change of the blood vessel is different according to the perimeter of the measurement portion and the pressure of the fluid bladder. Therefore, even when the volume change of the blood vessel is the same, an error occurs in the magnitude of the pressurized pulse wave amplitude according to the blood pressure value and the perimeter of the measurement portion, and the accuracy of the blood pressure measurement is reduced.

One or more embodiments of the present invention provides a blood pressure measurement device capable of improving the accuracy of the blood pressure measurement.

According to one aspect of the present invention, a blood pressure measurement device comprising a fluid bladder, a pressurizing unit for pressurizing the fluid bladder by injecting a fluid into the fluid bladder, a depressurizing unit for depressurizing the fluid bladder by discharging the fluid from the fluid bladder, a sensor for measuring an internal pressure change of the fluid bladder, a blood pressure measurement unit for calculating a systolic blood pressure value and a diastolic blood pressure value based on the internal pressure change of the fluid bladder obtained by the sensor, and a control unit for controlling the pressurizing unit, the depressurizing unit, and the blood pressure measurement unit, wherein the control unit controls the pressurizing unit and/or the depressurizing unit so as to achieve proportional relationship between an amount of change of the fluid per unit time with respect to the fluid bladder and an internal pressure change rate of the fluid bladder in one of pressurizing process in which the pressurizing unit injects the fluid into the fluid bladder and depressurizing process in which the depressurizing unit discharges the fluid from the fluid bladder, and wherein the blood pressure measurement unit calculates one of the systolic blood pressure value and the diastolic blood pressure value based on the internal pressure change of the fluid bladder obtained by the sensor in the pressurizing process and the blood pressure measurement unit calculates the other of the systolic blood pressure value and the diastolic blood pressure value based on the internal pressure change of the fluid bladder obtained by the sensor in the depressurizing process.

According to one or more embodiments of the present invention, the control unit may determine an amount of control for controlling an amount of discharge of the fluid discharged by the depressurizing unit so as to achieve proportional relationship between the amount of discharge from the fluid bladder, serving as the amount of change per unit time of the fluid with respect to the fluid bladder, and a depressurizing rate, serving as the internal pressure change rate, of the fluid bladder in the depressurizing process and controls the amount of discharge for controlling the amount of discharge. The blood pressure measurement unit may calculate a diastolic blood pressure value based on the internal pressure change of the fluid bladder obtained by the sensor in the depressurizing process in which the depressurizing unit discharges the fluid from the fluid bladder.

According to one or more embodiments of the present invention, the control unit may determine an amount of control for controlling an amount of discharge of the fluid discharged by the depressurizing unit so as to achieve proportional relationship between the amount of discharge from the fluid bladder, serving as the amount of change per unit time of the fluid with respect to the fluid bladder, and a depressurizing rate, serving as the internal pressure change rate, of the fluid bladder in the depressurizing process and controls the amount of discharge for controlling the amount of discharge. The blood pressure measurement unit may calculate a systolic blood pressure value based on the internal pressure change of the fluid bladder obtained by the sensor in the depressurizing process in which the depressurizing unit discharges the fluid from the fluid bladder.

According to one or more embodiments of the present invention, the depressurizing unit may include a valve arranged on the fluid bladder. The amount of control for controlling the amount of discharge may be a gap of the valve, and the control unit may determine a gap of the valve such that the internal pressure of the fluid bladder attains a depressurizing rate in which a predetermined number or more pulses are included in a time varying within a predetermined range sandwiching the systolic blood pressure, wherein the gap of the valve may be smaller than a gap determined in a case where the diastolic blood pressure value is calculated by the blood pressure measurement unit based on the internal pressure change of the fluid bladder obtained by the sensor in the depressurizing process in which the depressurizing unit discharges the fluid from the fluid bladder, and wherein the amount of discharge for controlling the amount of discharge may be controlled by controlling the gap of the valve such that the gap of the valve is maintained at the determined gap in the depressurizing process.

According to one or more embodiments of the present invention, the control unit may include an acquisition unit for obtaining information about a perimeter of a measuring portion, and the control unit may determine the gap of the valve according to the perimeter.

According to one or more embodiments of the present invention, the blood pressure measurement device may further include an input unit for inputting a perimeter, and information about the perimeter may be obtained from an input from the input unit.

According to one or more embodiments of the present invention, the acquisition unit may obtain the information about the perimeter based on a pressurizing time of the pressurizing unit in which the internal pressure of the fluid bladder reaches a predetermined pressure.

According to one or more embodiments of the present invention, the blood pressure measurement device may further include a wrapping member for wrapping the fluid bladder to wrap around the measurement portion. The wrapping member may include a slide resistor. The acquisition unit may obtain the information about the perimeter based on a resistance value obtained from the slide resistor by using the wrapping member to wrap the fluid bladder around the measurement portion.

According to one or more embodiments of the present invention, the depressurizing unit may includes a valve arranged on the fluid bladder. The amount of control for controlling the amount of discharge may be a gap of the valve, and the control unit may control the amount of discharge for controlling the amount of discharge by controlling the gap of the valve such that the gap of the valve is maintained at the determined gap in the depressurizing process.

According to one or more embodiments of the present invention, the blood pressure measurement unit may further calculate a blood pressure value based on the internal pressure change of the fluid bladder obtained by the sensor in the pressurizing process in which the pressurizing unit injects the fluid into the fluid bladder, and the control unit may determine the gap of the valve according to the blood pressure value calculated based on the internal pressure change of the fluid bladder in the pressurizing process.

According to one or more embodiments of the present invention, the blood pressure measurement unit may further calculate a cycle of a pulse wave based on the internal pressure change of the fluid bladder obtained by the sensor in the pressurizing process in which the pressurizing unit injects the fluid into the fluid bladder, and the control unit may determine the gap of the valve according to the cycle of the pulse wave calculated based on the internal pressure change of the fluid bladder in the pressurizing process.

According to one or more embodiments of the present invention, the control unit may control the pressurizing unit upon determining an amount of control for controlling the pressurizing unit based on the internal pressure of the fluid bladder so as to achieve proportional relationship between the amount of injection of the fluid per unit time into the fluid bladder injected by the pressurizing unit, serving as the amount of change per unit time of the fluid with respect to the fluid bladder in the pressurizing process, and a pressurizing rate, serving as the internal pressure change rate, of the fluid bladder. The blood pressure measurement unit may calculate the diastolic blood pressure value based on the internal pressure change of the fluid bladder obtained by the sensor in the pressurizing process in which the pressurizing unit injects the fluid into the fluid bladder.

According to one or more embodiments of the present invention, the control unit may control the pressurizing unit upon determining an amount of control for controlling the pressurizing unit based on the internal pressure of the fluid bladder so as to achieve proportional relationship between the amount of injection of the fluid per unit time into the fluid bladder injected by the pressurizing unit, serving as the amount of change per unit time of the fluid with respect to the fluid bladder in the pressurizing process, and a pressurizing rate, serving as the internal pressure change rate, of the fluid bladder. The blood pressure measurement unit may calculate the systolic blood pressure value based on the internal pressure change of the fluid bladder obtained by the sensor in the pressurizing process in which the pressurizing unit injects the fluid into the fluid bladder.

According to one or more embodiments of the present invention, the pressurizing unit may include a pump for injecting the fluid into the fluid bladder. The amount of control for controlling the pressurizing unit may be a drive voltage for driving the pump, and the control unit may update the drive voltage based on the internal pressure of the fluid bladder with a predetermined timing in the pressurizing process.

According to one or more embodiments of the present invention, the control unit may include an acquisition unit for obtaining information about a perimeter of a measuring portion, and the control unit may determine a control parameter for controlling the drive voltage for driving the pump based on the perimeter.

According to one or more embodiments of the present invention, the control unit controls the depressurizing unit to discharge the fluid from the fluid bladder, when the blood pressure measurement unit calculates the other of the systolic blood pressure value and the diastolic blood pressure value based on the internal pressure change of the fluid bladder obtained by the sensor in the depressurizing process in which the depressurizing unit discharges the fluid from the fluid bladder.

According to another aspect of the present invention, a blood pressure measurement device includes a fluid bladder, a pressurizing unit for pressurizing the fluid bladder by injecting a fluid into the fluid bladder, a depressurizing unit for depressurizing the fluid bladder by discharging the fluid from the fluid bladder, a sensor for measuring an internal pressure change of the fluid bladder, a blood pressure measurement unit for calculating a blood pressure value based on the internal pressure change of the fluid bladder obtained by the sensor in the depressurizing process in which the depressurizing unit discharges the fluid from the fluid bladder, and a control unit for controlling the pressurizing unit, the depressurizing unit, and the blood pressure measurement unit, wherein the control unit determines an amount of control for controlling an amount of discharge of the fluid discharged by the depressurizing unit so as to achieve proportional relationship between the amount of discharge and a depressurizing rate of the fluid bladder in the depressurizing process, and controls the amount of discharge.

According to one or more embodiments of the present invention, the depressurizing unit may include a valve arranged on the fluid bladder. The amount of control may be a gap of the valve, and the control unit may control the amount of discharge by controlling the gap of the valve such that the gap of the valve is maintained at the determined gap in the depressurizing process.

According to one or more embodiments of the present invention, the control unit may determine the gap of the valve, i.e., the amount of control, such that the internal pressure of the fluid bladder attains a depressurizing rate in which a predetermined number of more pulses are included in a time varying from the systolic blood pressure to the diastolic blood pressure.

According to one or more embodiments of the present invention, the pressurizing unit may include a pump. The acquisition unit may obtain the information about the perimeter based on the number of rotations of the pump and the internal pressure of the fluid bladder.

According to one or more embodiments of the present invention, the blood pressure measurement device may further include a measurement unit for measuring an amount of discharge, wherein the control unit may control the amount of discharge of the fluid discharged by the depressurizing unit so as to achieve proportional relationship between the amount of discharge and the depressurizing rate of the fluid bladder in the depressurizing process, based on the amount of discharge measured by the measurement unit and the internal pressure change of the fluid bladder obtained by the sensor.

According to one or more embodiments of the present invention, the blood pressure measurement device may further include an increasing unit for increasing a volume of the fluid bladder, wherein the pressurizing unit may pressurize the fluid bladder by injecting the fluid into the fluid bladder whose volume has been increased by the increasing unit.

According to one or more embodiments of the present invention, the increasing unit may include an injection unit for injecting a non-pressurized fluid into the fluid bladder.

The control unit may control the injection unit to inject the non-pressurized fluid into the fluid bladder before the pressurizing unit injects the fluid into the fluid bladder.

According to one or more embodiments of the present invention, the control unit may control the injection unit to inject a predetermined amount of non-pressurized fluid into the fluid bladder before the pressurizing unit injects the fluid into the fluid bladder.

According to one or more embodiments of the present invention, the control unit may execute a control including the steps of causing the injection unit to inject the non-pressurized fluid into the fluid bladder before the pressurizing unit injects the fluid into the fluid bladder, so that the pressure of the fluid bladder reaches a predetermined pressure or a pressurizing rate of the fluid bladder reaches a predetermined pressurizing rate, releasing the pressure of the fluid bladder to atmospheric pressure after the pressure of the fluid bladder reaches the predetermined pressure or after the pressurizing rate of the fluid bladder reaches the predetermined pressurizing rate, and closing the fluid bladder and causing the pressurizing unit to start injection of the fluid after the pressure of the fluid bladder becomes atmospheric pressure.

According to one or more embodiments of the present invention, a filter may be arranged at a portion connecting an outlet for discharging the fluid with the depressurizing unit and the fluid bladder, wherein the filter allows the fluid to pass through and does not allow the non-pressurized fluid to pass through.

According to one or more embodiments of the present invention, the increasing unit may be a filling member arranged within the fluid bladder.

According to one or more embodiments of the present invention, the filling member may include any one of a sponge, a spring, and microbeads.

According to another aspect of the present invention, a blood pressure measurement device includes a fluid bladder, a pressurizing unit for pressurizing the fluid bladder by injecting a fluid into the fluid bladder, a sensor for measuring an internal pressure change of the fluid bladder, a blood pressure measurement unit for calculating a blood pressure value based on the internal pressure change of the fluid bladder obtained by the sensor in the pressurizing process in which the pressurizing unit injects the fluid into the fluid bladder, and a control unit for controlling the pressurizing unit and the blood pressure measurement unit, wherein the control unit determines an amount of control for controlling the pressurizing unit based on the internal pressure of the fluid bladder so as to achieve proportional relationship between the amount of injection of the fluid per unit time into the fluid bladder injected by the pressurizing unit and a pressurizing rate of the fluid bladder, and controls the pressurizing unit.

According to one or more embodiments of the present invention, the pressurizing unit may include a pump for injecting the fluid into the fluid bladder. The amount of control may be a drive voltage for driving the pump, and the control unit may update the drive voltage based on the internal pressure of the fluid bladder with a predetermined timing in the pressurizing process.

According to one or more embodiments of the present invention, the control unit may determine the drive voltage of the pump, i.e., the amount of control, such that the internal pressure of the fluid bladder attains a pressurizing rate in which a predetermined number of or more pulses are included in a time varying from the diastolic blood pressure to the systolic blood pressure.

According to one or more embodiments of the present invention, the acquisition unit may obtain the information about the perimeter based on the number of rotations of the pump and the internal pressure of the fluid bladder.

According to one or more embodiments of the present invention, the blood pressure measurement device further includes a measurement unit for measuring an amount of injection of the fluid into the fluid bladder, wherein the control unit may control the pressurizing unit so as to achieve proportional relationship between the amount of injection of the fluid per unit time into the fluid bladder injected by the pressurizing unit and the pressurizing rate of the fluid bladder in the pressurizing process, based on the amount of injection of the fluid into the fluid bladder, per unit time, measured by the measurement unit.

According to one or more embodiments of the present invention, the control unit may determine whether the pressurizing rate of the fluid bladder is within an acceptable range, and when the pressurizing rate is determined not to be within the acceptable range, the control unit stops the pressurizing operation of the pressurizing unit.

According to one or more embodiments of the present invention, in the blood pressure measurement device, the detection accuracy of the volume change of the blood vessel can be brought closer to a constant level regardless of the pressure of the fluid bladder. Thereby, blood pressure measurement error can be reduced. Further, even when the volume of the fluid bladder is different according to the perimeter of the measurement portion, a rate of the change of the detection accuracy of the volume change of the blood vessel can be brought closer to a constant rate. Thereby, blood pressure measurement error can be reduced. Further, this eliminates the necessity of correcting the volume of the fluid bladder which is different according to the perimeter of the measurement portion.

DETAILED DESCRIPTION

Figure 1:
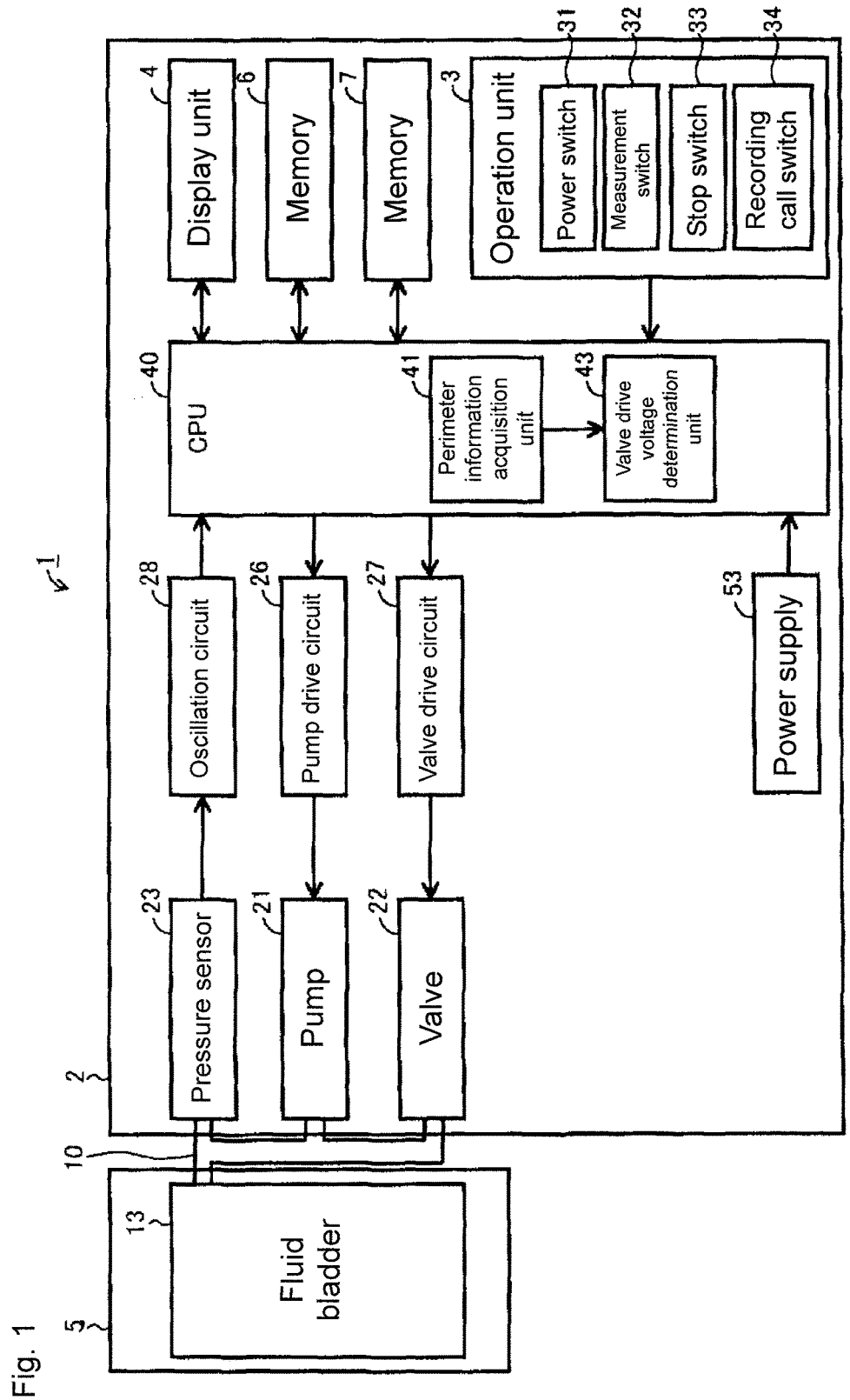
FIG. 1 is a block diagram illustrating a specific example of hardware configuration of a sphygmomanometer serving as a blood pressure measurement device according to the first embodiment.

Embodiments of the present invention will be hereinafter described with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. In the below description, the same parts and constituent elements are denoted with the same reference numerals. The names and the functions thereof are also the same.

First Embodiment

In the first embodiment, a blood pressure measurement device for measuring a blood pressure during depressurizing process of a fluid bladder will be described.

Referring to FIG. 1, a sphygmomanometer 1 serving as a blood pressure measurement device according to the first embodiment includes a main body 2, a cuff 5 wrapped around a measurement portion, and these are connected via a tube 10. An operation unit 3 such as a switch and a display unit 4 for displaying measurement results and the like are arranged on a front surface of the main body 2. The operation unit 3 includes a power switch 31 for giving instruction for turning on and off the power supply, a measurement switch 32 for giving an instruction for starting measurement, a stop switch 33 for giving an instruction for stopping measurement, and a recording call switch 34 for calling and displaying a recorded measurement value. A cuff 5 is arranged with a fluid bladder 13. A fluid injected into the fluid bladder 13 and discharged from the fluid bladder 13 is, for example, air. When the cuff 5 is wrapped around the measurement portion, the fluid bladder 13 is pressed against the measurement portion. Examples of measurement portions include an upper arm and a wrist.

The fluid bladder 13 is connected to a pressure sensor 23 for measuring an internal pressure change of the fluid bladder 13, a pump 21 for injecting and discharging a fluid into/out of the fluid bladder 13, and a valve 22. The pressure sensor 23, the pump 21, and the valve 22 are respectively connected to an oscillation circuit 28, a pump drive circuit 26, and a valve drive circuit 27. Further, the oscillation circuit 28, the pump drive circuit 26, and the valve drive circuit 27 are connected to a CPU (Central Processing Unit) 40 controlling the entire sphygmomanometer 1.

The CPU 40 is further connected to the display unit 4, the operation unit 3, a memory 6 for storing programs executed by the CPU 40 and serving as a work area when a program is executed, a memory 7 storing measurement results and the like, and a power supply 53.

The CPU 40 is driven by receiving power supply from the power supply 53. The CPU 40 includes a perimeter information acquisition unit 41 and a valve drive voltage determination unit 43. These are formed in the CPU 40 by causing the CPU 40 to execute a predetermined program stored in the memory 6 based on an operation signal inputted from the operation unit 3. The perimeter information acquisition unit 41 obtains perimeter information representing the size of the measurement portion, and inputs the perimeter information into the valve drive voltage determination unit 43. The valve drive voltage determination unit 43 determines a voltage (hereinafter, drive voltage Ev) for driving a valve 22 based on the perimeter information. The CPU 40 outputs a control signal to the valve drive circuit 27 according to the drive voltage Ev determined by the valve drive voltage determination unit 43. In addition, the CPU 40 executes a predetermined program stored in the memory 6 and outputs a control signal to the pump drive circuit 26 based on an operation signal inputted from the operation unit 3.

The pump drive circuit 26 and the valve drive circuit 27 drive the pump 21 and the valve 22 according to the control signals. The pump 21 is driven by the control of the pump drive circuit 26 according to the control signal given by the CPU 40, and the pump 21 injects a fluid into the fluid bladder 13. Open/close and opening width (hereinafter referred to as a gap) of the valve 22 is controlled by the valve drive circuit 27 according to the control signal given by the CPU 40, and the fluid in the fluid bladder 13 is discharged through the valve 22.

The pressure sensor 23 is a capacitance-type pressure sensor, and a capacitance value of the pressure sensor 23 changes according to an internal pressure of the fluid bladder 13. The oscillation circuit 28 is converted into a signal of an oscillation frequency according to a capacitance value of the pressure sensor 23, and the signal is inputted to the CPU 40. The CPU 40 executes a predetermined processing based on an internal pressure change of the fluid bladder 13 obtained from the pressure sensor 23, and outputs the control signals to the pump drive circuit 26 and the valve drive circuit 27 according to the result of the processing. In addition, the CPU 40 calculates a blood pressure value based on an internal pressure change of the fluid bladder 13 obtained from the pressure sensor 23, and performs processing for causing the display unit 4 to display a measurement result, thus outputting display data and the control signal to the display unit 4. Further, the CPU 40 performs processing for storing the blood pressure value to the memory 7.

The first specific example of processing executed in response to an operation of the measurement switch 32 in the sphygmomanometer 1 will be described with reference to a flowchart of FIG. 2. The processing shown in the flowchart of FIG. 2 is achieved by causing the CPU 40 to execute a predetermined program stored in the memory 6.

Figure 2:
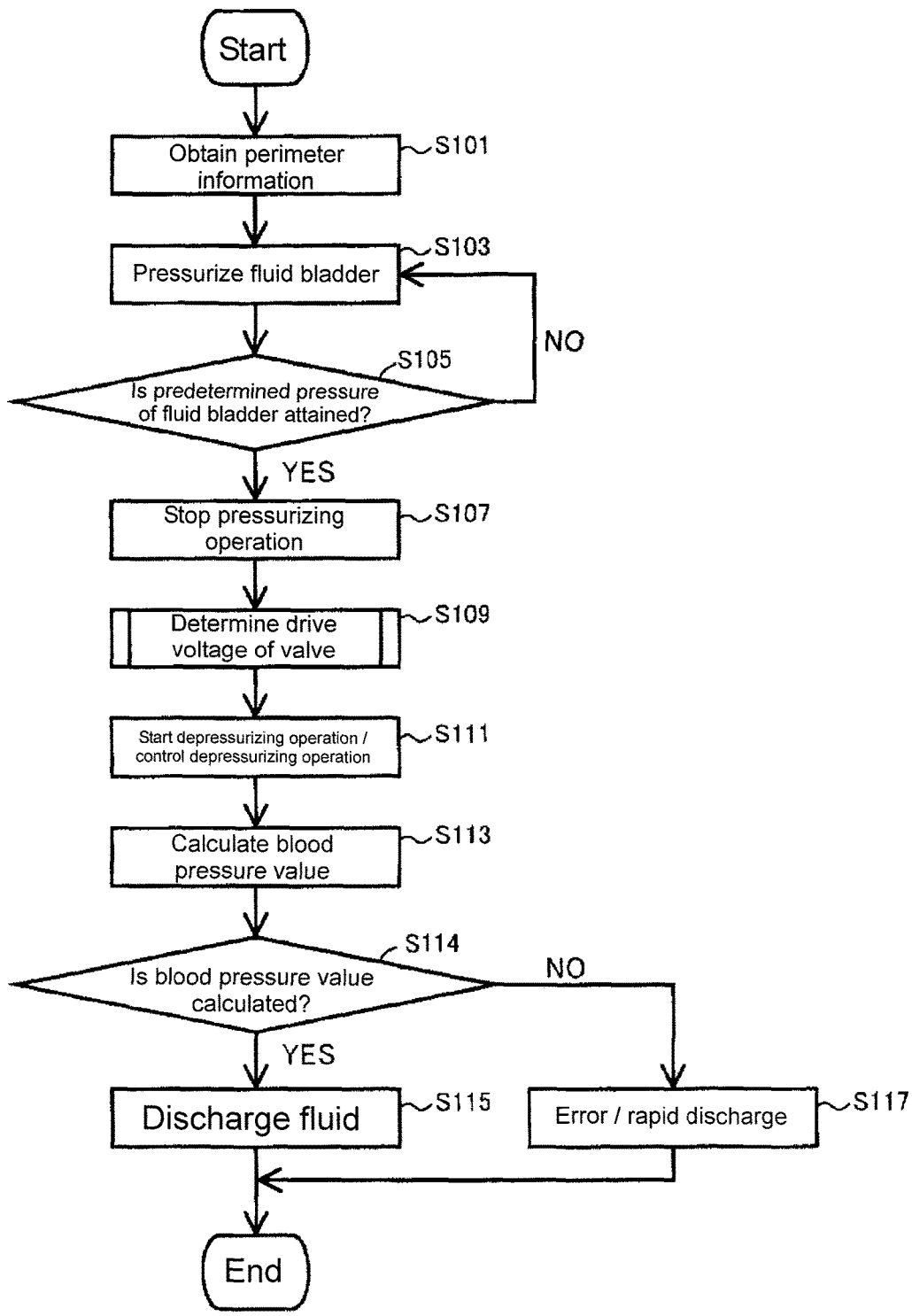
FIG. 2 is a flowchart illustrating a first specific example of processing executed in response to an operation of a measurement switch on the sphygmomanometer according to the first embodiment.

Referring to FIG. 2, the CPU 40 monitors an operation signal inputted from the operation unit 3. When the CPU 40 detects that the measurement switch 32 is operated, the perimeter information acquisition unit 41 of the CPU 40 obtains the perimeter information representing the perimeter of the measurement portion, i.e., the size of the measurement portion in step S101. In this embodiment, a switch constituting the operation unit 3 and the like is used to input perimeter information such as "thick" and "thin" during measurement, and the perimeter information acquisition unit 41 obtains the perimeter information from an operation signal given by the operation unit 3.

Figure 3:
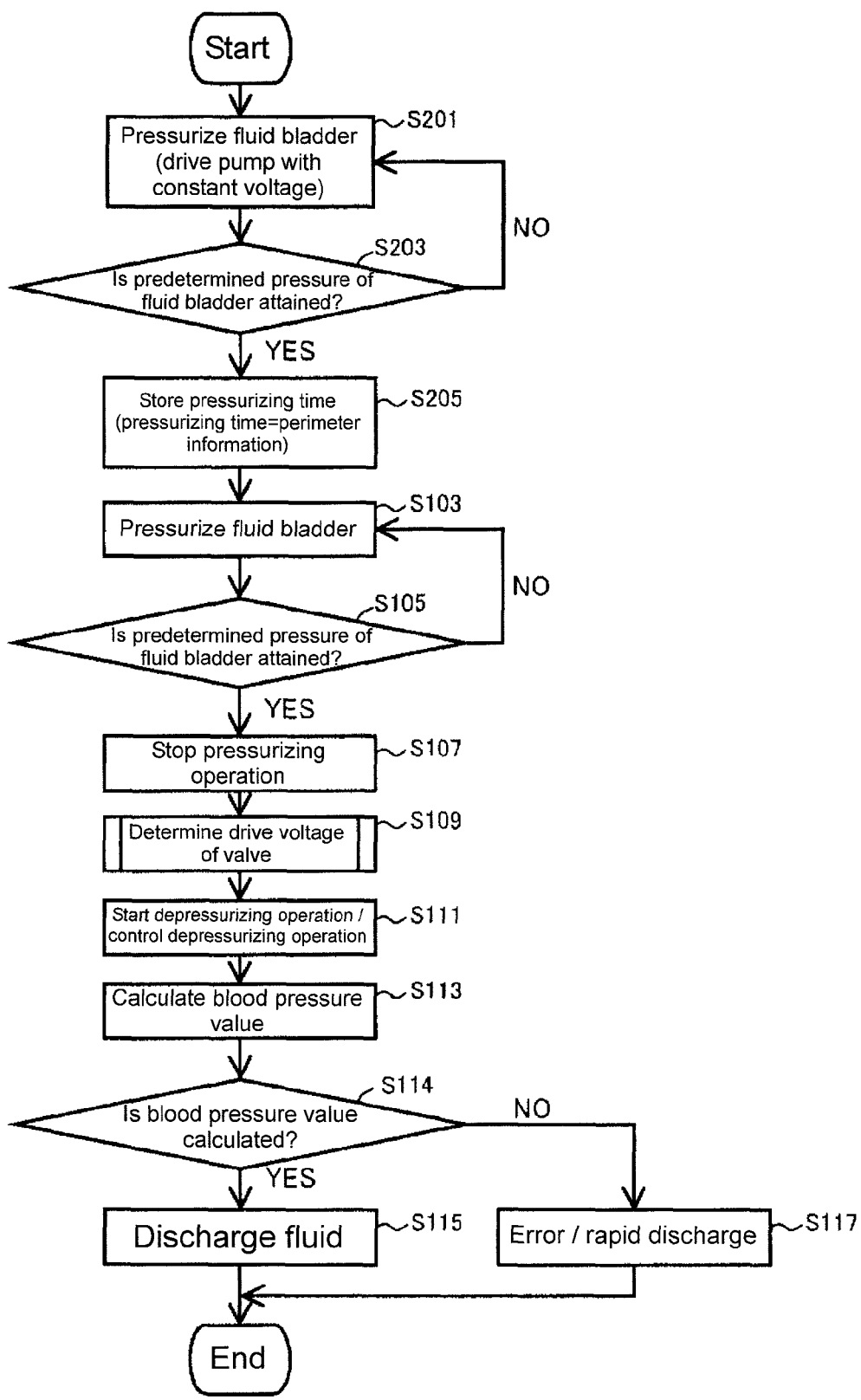
FIG. 3 is a flowchart illustrating a second specific example of processing executed in response to an operation of the measurement switch on the sphygmomanometer according to the first embodiment.
Figure 4A:
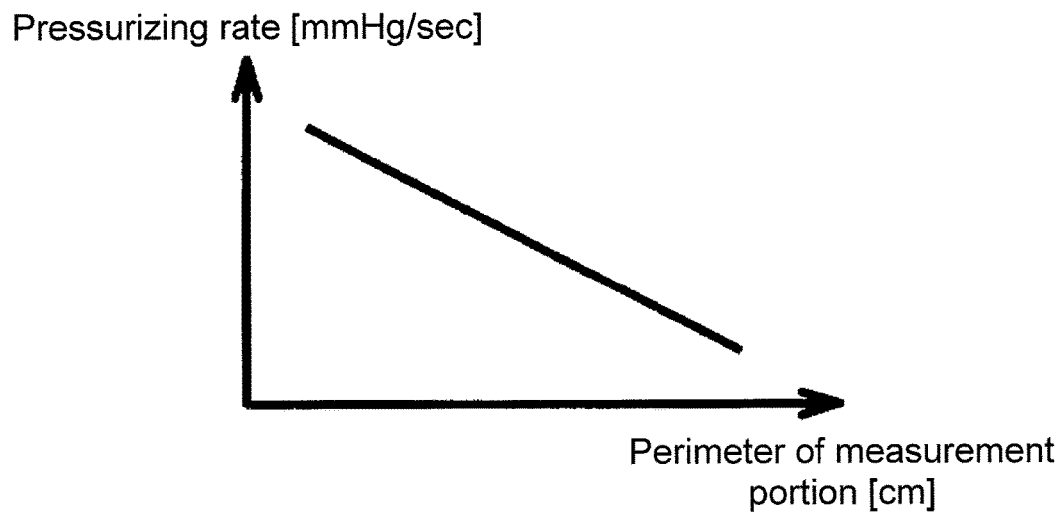
FIG. 4A is a diagram illustrating relationship between a perimeter of a measurement portion and a pressurizing rate.
Figure 4B:
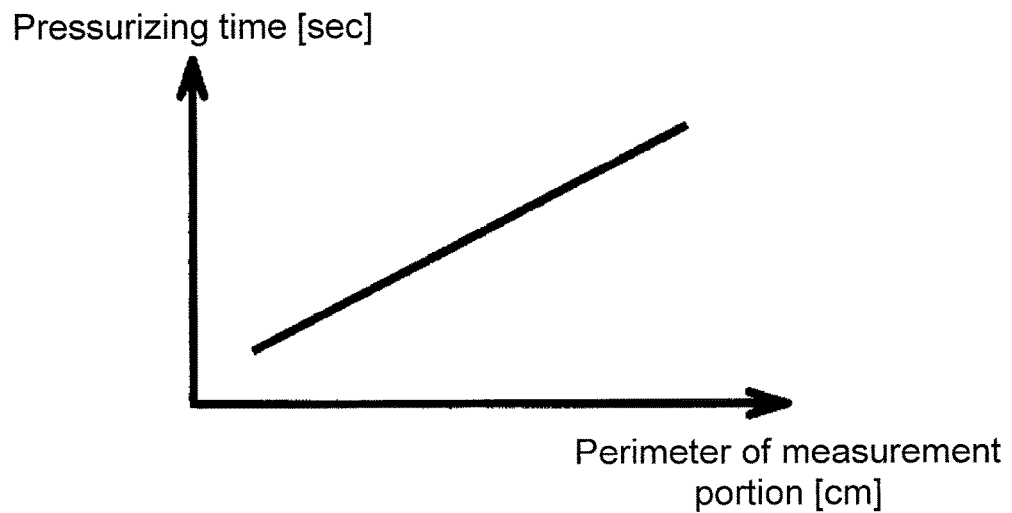
FIG. 4B is a diagram illustrating relationship between a perimeter of a measurement portion and a pressurizing time.

It should be noted that the perimeter information acquisition method performed by the perimeter information acquisition unit 41 is not limited to the above method. For example, in the second specific example of processing executed in response to an operation of the measurement switch 32 in the sphygmomanometer 1, the perimeter information may be obtained in step S201 to S205 instead of step S101 as shown in FIG. 3. More specifically, in step S201, the CPU 40 outputs, to the pump drive circuit 26, the control signal for driving the pump 21 with a predetermined voltage previously defined, and drives the pump 21 with a predetermined voltage, thereby pressurizing the fluid bladder 13 until the fluid bladder 13 reaches a predetermined pressure previously defined. When the fluid bladder 13 reaches the predetermined pressure (YES in step S203), the CPU 40 stores a pressurizing time in which the fluid bladder 13 reaches a predetermined pressure in step S205. As shown in FIG. 4A, in a case where the drive voltage driven by the pump 21 is the same, the pressurizing rate decreases as the perimeter of the measurement portion increases. Therefore, as shown in FIG. 4B, the pressurizing time increases as the perimeter of the measuring portion increases. That is, the pressurizing time for which the fluid bladder 13 reaches the predetermined pressure is said to be an index representing the perimeter of the measuring portion. Accordingly, the perimeter information acquisition unit 41 obtains the pressurizing time stored in step S205 as the perimeter information. Alternatively, the perimeter information acquisition unit 41 can obtain the perimeter information from the pressure of the fluid bladder 13 and the number of rotations of the pump 21, in the same manner, instead of obtaining it from the pressurizing time. As another example, a cloth (not shown) for wrapping the fluid bladder 13 around the measurement portion may include a slide resistor, and the perimeter information acquisition unit 41 may obtain the perimeter information from a resistance value obtained from the slide resistor when the fluid bladder 13 is wrapped around the measurement portion.

In steps S103, S105, the CPU 40 outputs a control signal to the pump drive circuit 26, and the fluid bladder 13 pressurizes the fluid bladder 13 until the fluid bladder reaches the predetermined pressure defined in advance. When the fluid bladder 13 reaches the predetermined pressure (YES in step S105), the CPU 40 outputs a control signal to the pump drive circuit 26 in step S107, and stops pressurizing the fluid bladder 13. Thereafter, in step S109, the valve drive voltage determination unit 43 of the CPU 40 determines the drive voltage Ev of the valve 22 based on the perimeter information obtained in step S101 or step S201 to S205. In step S111, the CPU 40 outputs a control signal to the valve drive circuit 27 so as to drive the valve 22 while maintaining the drive voltage Ev determined in step S109, and starts depressurizing the fluid bladder 13. In step S113, the CPU 40 extracts a vibrational component caused by a volume change of an artery, superposed on the internal pressure of the fluid bladder 13, obtained during decompressing process, and calculates a blood pressure value according to a predetermined calculation. It should be noted that in a case where the depressurizing rate is too fast in step S111 to calculate the blood pressure value in step S113, or on the contrary, the depressurizing rate is too slow in step S111 to discharge the fluid (NO in step S114), the CPU 40 determines an occurrence of an error in step S117, and outputs a control signal to the valve drive circuit 27 to open the valve 22 so as to rapidly discharge the fluid from the fluid bladder 13. In the other case, i.e., where the blood pressure value is calculated in step S113 (YES in step S114), the valve 22 is opened according to the control signal given by the CPU 40 in step S115, so that the fluid is discharged from the fluid bladder 13.

The determination of the drive voltage Ev in the valve drive voltage determination unit 43 in step S109 will be described.

Figure 5:
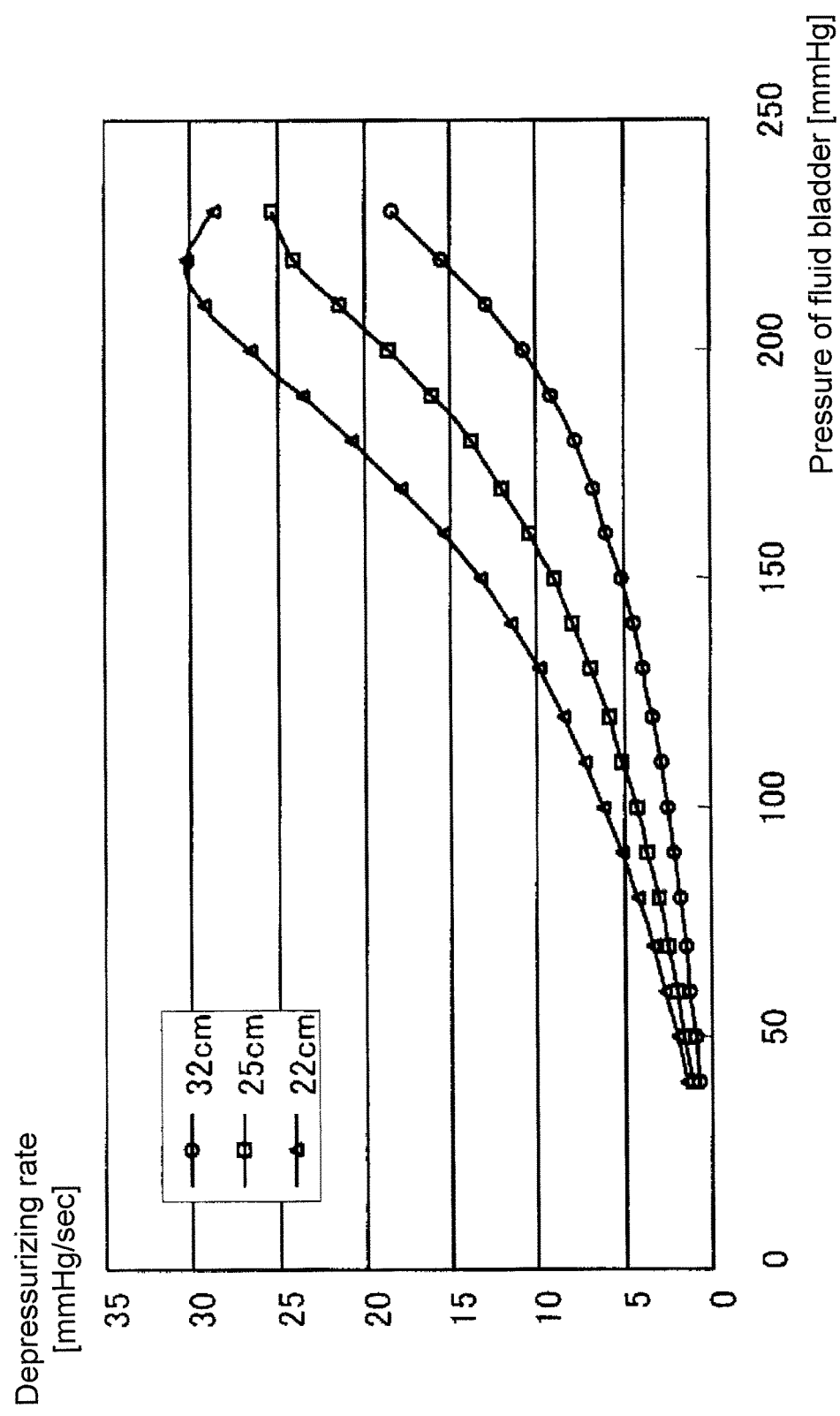
FIG. 5 is a diagram illustrating, for each perimeter of a measurement portion, the degree of change of a depressurizing rate with respect to a pressure of a fluid bladder when a drive voltage of a valve is kept constant.

In this case, when the drive voltage Ev is maintained at a constant voltage, the degree of change of the depressurizing rate with respect to a pressure of the fluid bladder is different according to the perimeter of the measuring portion as shown in FIG. 5. This will be described more specifically with reference to FIG. 5. The smaller the perimeter of the measuring portion is, the larger the degree of change of the depressurizing rate is. The larger the perimeter of the measuring portion is, the smaller the degree of change of the depressurizing rate is. In other words, it is understood from the relationship shown in FIG. 5 that the perimeter of the measuring portion is a parameter for determining the drive voltage Ev.

In step S109, the valve drive voltage determination unit 43 uses the relationship shown in FIG. 5 to determine the drive voltage Ev. As a specific example, the valve drive voltage determination unit 43 determines the drive voltage Ev by substituting the perimeter information obtained in step S101 or steps S201 to S205 into the following expression (1).

$$\text{Drive voltage } Ev = \alpha \times \text{perimeter information} + \beta \quad \text{Expression (1)}$$

Figure 6:
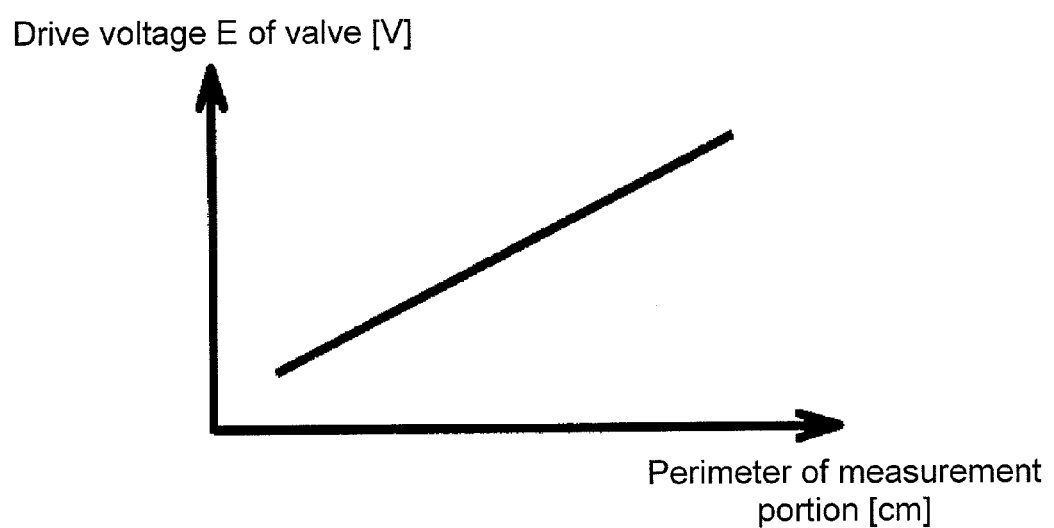
FIG. 6 is a diagram illustrating relationship between a drive voltage of a valve and a perimeter of a measurement portion, which is determined by the sphygmomanometer according to the first embodiment.

When the above expression (1) is used in step S109, the drive voltage Ev is determined as a magnitude in proportional to the perimeter of the measuring portion as shown in FIG. 6.

Figure 7:
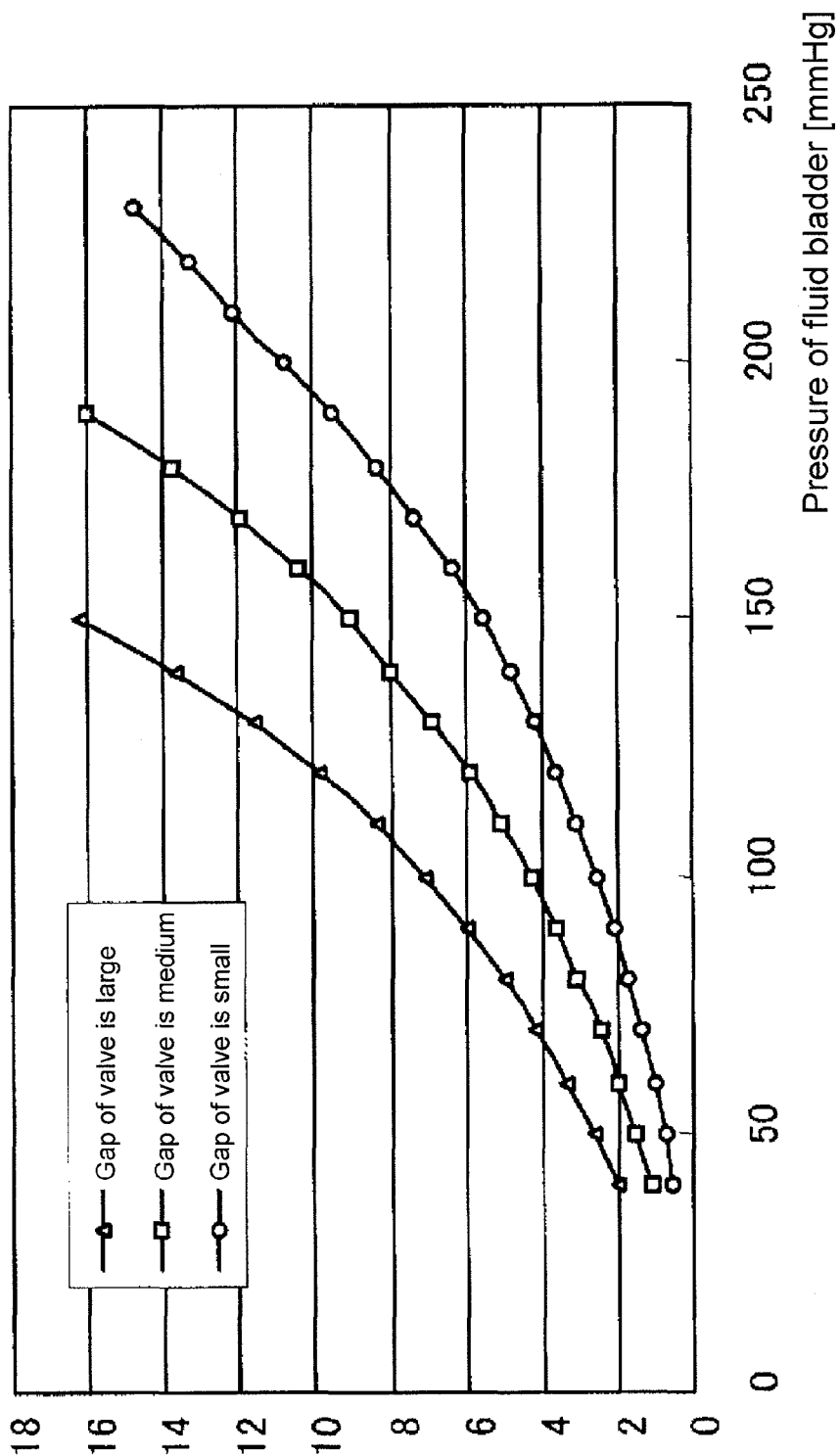
FIG. 7 is a diagram illustrating, for each gap of a valve, the degree of change of a depressurizing rate with respect to a pressure of a fluid bladder when the perimeter of the measurement portion is the same.

It should be noted that in a case where the perimeter of the measuring portion is the same, the degree of change of the depressurizing rate with respect to the pressure of the fluid bladder 13 is different according to a gap of the valve 22, i.e., the magnitude of the drive voltage, as shown in FIG. 7. This will be described more specifically with reference to FIG. 7. The larger the gap of the valve 22 is, the larger the degree of change of the depressurizing rate is. The smaller the gap is, the smaller the degree of change of the depressurizing rate is. Therefore, according to the relationship as shown in FIG. 7, the gap has such size that the depressurizing rate of the fluid bladder 13 between the calculation of the systolic blood pressure and the calculation of the diastolic blood pressure stays within a predetermined rate range. More specifically, the gap has such size achieving a depressurizing rate such that the number of pulses detected between the systolic blood pressure and the diastolic blood pressure during depressurizing process is equal to or more than a predetermined number. According to one or more embodiments of the present invention, the above "predetermined number" is five. This is because, as described in Japanese Unexamined Patent Publication No. 2001-70263 filed by the applicant of the present application, it is adequate to make a setting in view of the performance of algorithm of depressurizing measurement so as to control the depressurizing rate such that about five pulses are measured between the systolic blood pressure and the diastolic blood pressure during depressurizing process. The depressurizing rate allowing five or more pulses to be measured between the systolic blood pressure and the diastolic blood pressure during depressurizing process can be obtained through, for example, experiments and the like, and is assumed to be stored in the memory 6 in advance. More specifically, according to one or more embodiments of the present invention, the value of the depressurizing rate is about 3 mmHg/sec to 13 mmHg/sec. Therefore, the coefficients α, β of the above expression (1) may be such values that causes the blood pressure depressurizing rate of the pressure of the fluid bladder 13 within a range of about the blood pressure value to be in a range of target depressurizing rate, i.e., about 3 mmHg/sec to 13 mmHg/sec. These coefficients α, β can be obtained through, for example, experiments and the like, and is assumed to be stored in the memory 6 in advance. In the above example, the drive voltage Ev is determined by inputting the obtained perimeter information into the above expression (1) in step S109. Alternatively, instead of the expression (1), the memory 6 may store a table defining relationship between the perimeter information and the drive voltage Ev, and the valve drive voltage determination unit 43 may read the drive voltage Ev corresponding to the obtained perimeter information from the table.

[Modification 1]

Figure 8:
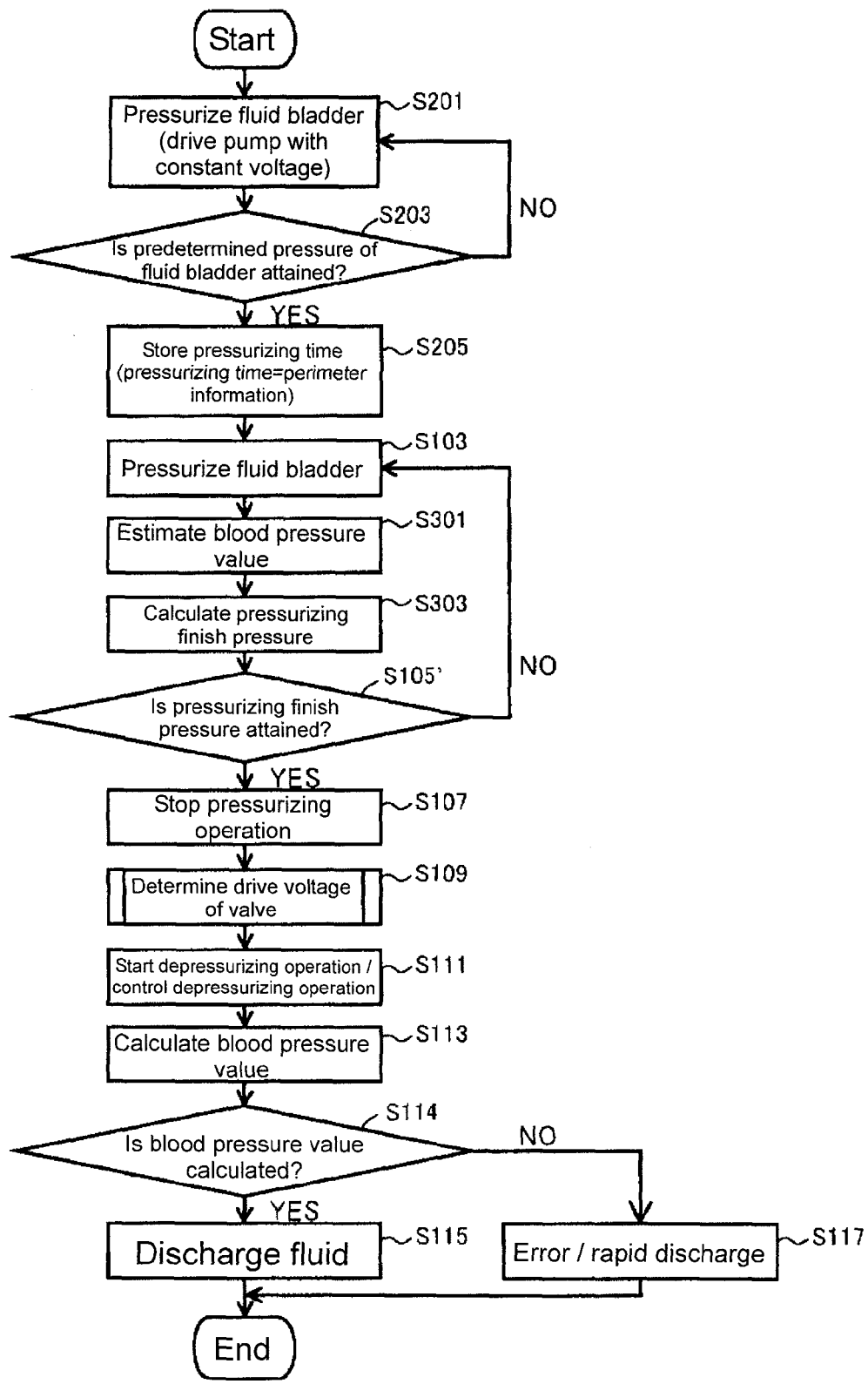
FIG. 8 is a flowchart illustrating a modification of the processing executed in response to an operation of the measurement switch on the sphygmomanometer according to the first embodiment.

A modification of the processing executed in response to an operation of the measurement switch 32 in the sphygmomanometer 1 will be described with reference to a flowchart of FIG. 8. The processing shown in FIG. 8 is performed in the same manner as the second specific example shown in FIG. 3. That is, in steps S201 to S205, the perimeter of the measuring portion is estimated based on the pressurizing time in which the pressure of the fluid bladder 13 attains the predetermined pressure, and in the subsequent pressurizing process, the CPU 40 estimates the systolic blood pressure value based on an internal pressure change of the fluid bladder 13 obtained from the pressure sensor 23 in step S301. In step S303, the pressure of the fluid bladder 13 at the end of the pressurizing process is calculated. The sphygmomanometer 1 is configured to calculate a blood pressure value based on an internal pressure change of the fluid bladder 13 obtained in depressurizing process after the fluid bladder 13 is pressurized to a predetermined pressure. Accordingly, in step S303, the CPU 40 calculates, as a pressurizing finish pressure, a pressure value higher than the systolic blood pressure value estimated in step S301 by the predetermined pressure value. When the pressure of the fluid bladder 13 attains the pressurizing finish pressure calculated in step S303 (YES in step S105'), the drive voltage Ev is thereafter determined in the same manner as the processing shown in FIGS. 2 and 3, and the blood pressure value is calculated in depressurizing process in which control is performed to drive the valve while maintaining the drive voltage Ev.

In the modification, in step S109, the valve drive voltage determination unit 43 determines the drive voltage Ev in view of the systolic blood pressure value estimated in step S301, instead of or in addition to the relationship shown in FIG. 5 described above. As a specific example, the valve drive voltage determination unit 43 determines the drive voltage Ev by substituting the perimeter information obtained in step S101 or steps S201 to S205 into the following expression (2).

Drive voltage $Ev = \alpha \times$ perimeter information $+ \beta +$ offset amount $S$, Offset amount $S =$ estimated systolic blood pressure value $\times \gamma$                                  Expression (2)

Figure 9:
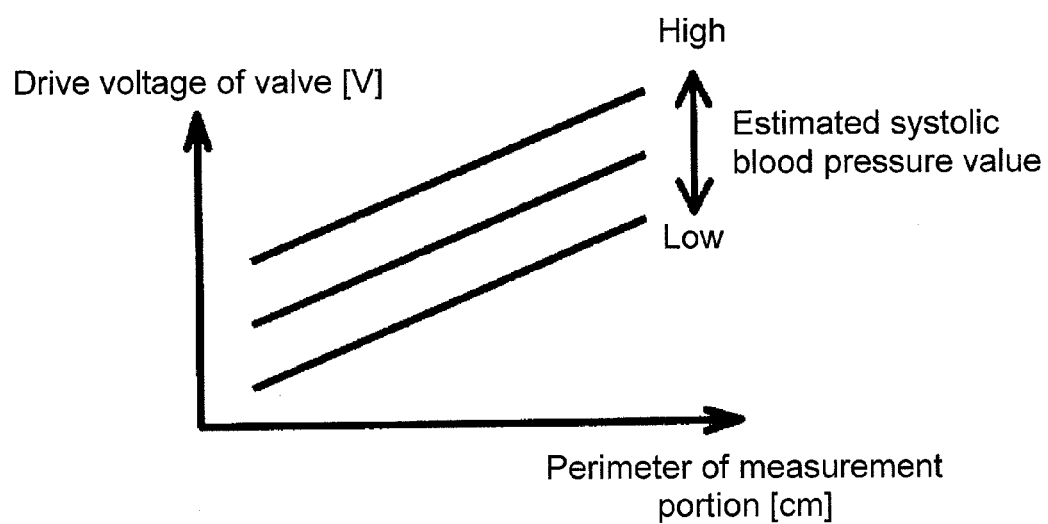
FIG. 9 is a diagram illustrating relationship between a drive voltage of a valve and a perimeter of a measurement portion, which is determined by the sphygmomanometer according to the first modification of the first embodiment.

In the modification, the above expression (2) is used in step S109. Accordingly, as shown in FIG. 9, the drive voltage Ev is determined as a magnitude in proportional to the perimeter of the measuring portion and in accordance with the estimated systolic blood pressure. In the above specific example, the offset amount S is assumed to be calculated based on the estimated systolic blood pressure value. Alternatively, the offset amount S may be calculated based on an estimated diastolic blood pressure value, a pulse pressure, or a cycle of a pulse wave.

Therefore, according to the relationship described with reference to FIG. 7, the gap has such size that causes the blood pressure depressurizing rate of the pressure of the fluid bladder 13 within the range of about the blood pressure value to be in the range of target depressurizing rate. Accordingly, the coefficient γ of the above expression (2) can also be such value that causes the depressurizing rate of the fluid bladder 13 from the calculation of the systolic blood pressure to the calculation of the diastolic blood pressure to be in the range of target depressurizing rate, i.e., about 3 mmHg/sec to 13 mmHg/sec.

Figure 10A:
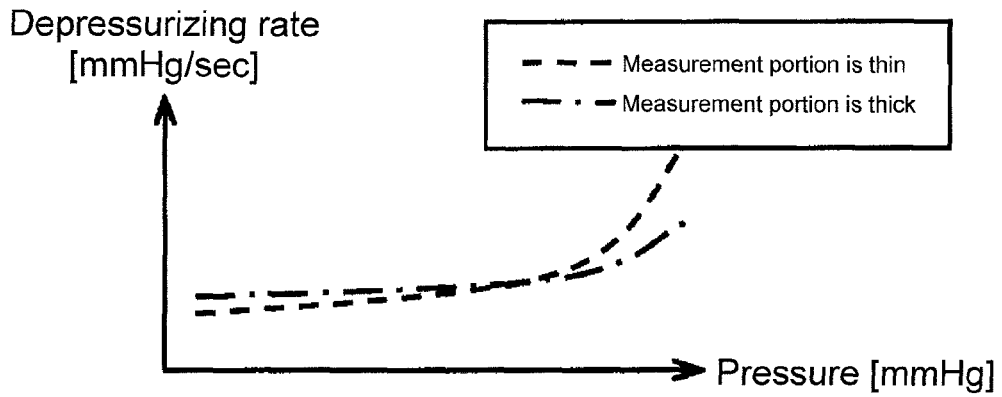
FIG. 10A is a diagram illustrating relationship between a pressure of a fluid bladder and a depressurizing rate in the sphygmomanometer according to the first embodiment.
Figure 10B:
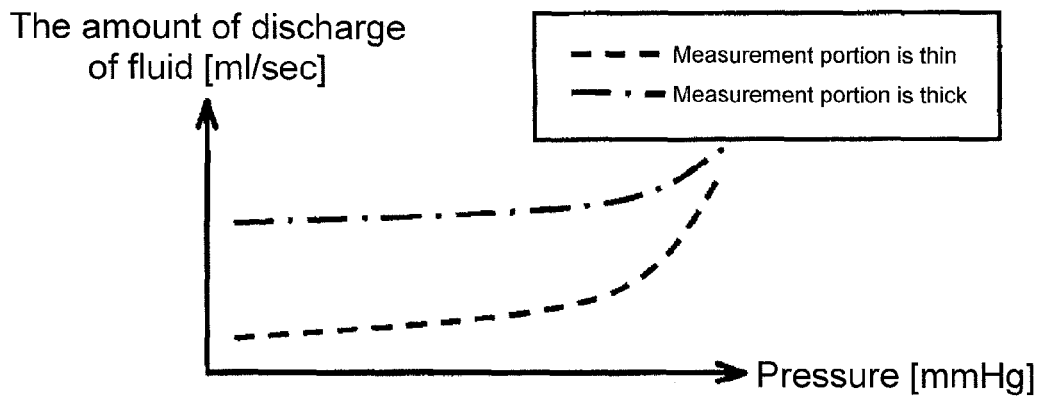
FIG. 10B is a diagram illustrating relationship between a pressure of a fluid bladder and the amount of discharge of a fluid in the sphygmomanometer according to the first embodiment.

In step S111, the CPU 40 performs control so as to drive the valve 22 while maintaining the drive voltage Ev determined in step S109. That is, the gap of the valve 22 is controlled to be a constant during depressurizing process. Accordingly, during the depressurizing process, the depressurizing rate of the fluid bladder 13 changes as shown in FIG. 10A according to a pressure change of the fluid bladder 13. More specifically, as can be seen from FIG. 10A, when the pressure of the fluid bladder 13 is equal to or less than a certain pressure, the depressurizing rate of the fluid bladder 13 has almost the same value regardless of the magnitude of the perimeter of the measuring portion, and is not changed by subsequent (depressurizing) pressure change. During the depressurizing process, the amount of discharge from the valve 22 in the pressure of the fluid bladder 13 changes as shown in FIG. 10B according to a pressure change of the fluid bladder 13. More specifically, as can be seen from FIG. 10B, when the pressure of the fluid bladder 13 is equal to or less than a certain pressure, the amount of discharge from the valve 22 is a value according to the perimeter of the measuring portion, and is not changed by subsequent (depressurizing) pressure change. In other words, it is understood from the relationship shown in FIGS. 10A and 10B that the control for causing the drive voltage Ev to be constant, i.e., the control for causing the gap of the valve 22 to be constant, is equivalent to the control of the drive voltage Ev for achieving proportional relationship between the amount of discharge from the valve 22 and the depressurizing rate of the fluid bladder 13.

Figure 10C:
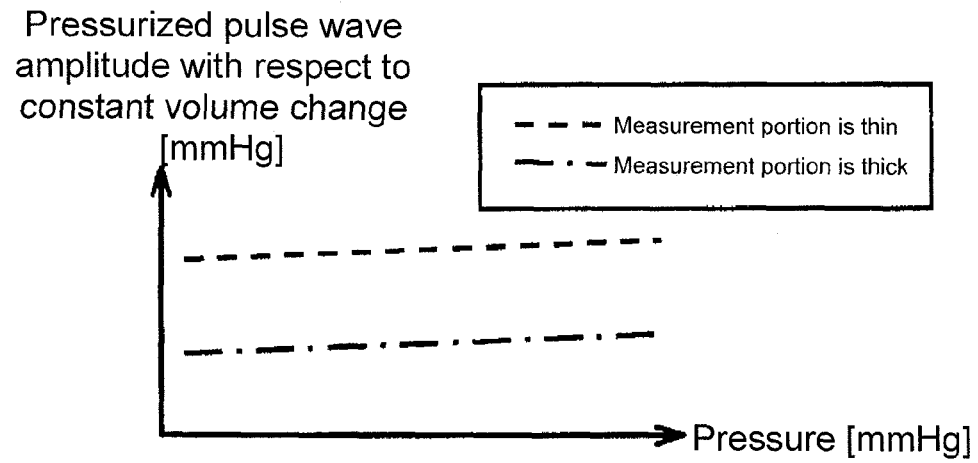
FIG. 10C is a diagram illustrating relationship between a pressure of a fluid bladder and a pressurized pulse wave amplitude value with respect to a constant volume change in the sphygmomanometer according to the first embodiment.

In the sphygmomanometer 1, the CPU 40 performs control as described above, thereby achieving almost proportional relationship between the flow amount of the fluid discharged from the fluid bladder 13 and the depressurizing rate. Accordingly, the detection accuracy of the volume change of the blood vessel can be made almost constant, and the detection accuracy can be improved. Therefore, as shown in FIG. 10C, regardless of the pressure change of the fluid bladder 13, the pressurized pulse wave amplitude with respect to a constant volume change can be a constant value according to the perimeter of the measuring portion.

Figure 11:
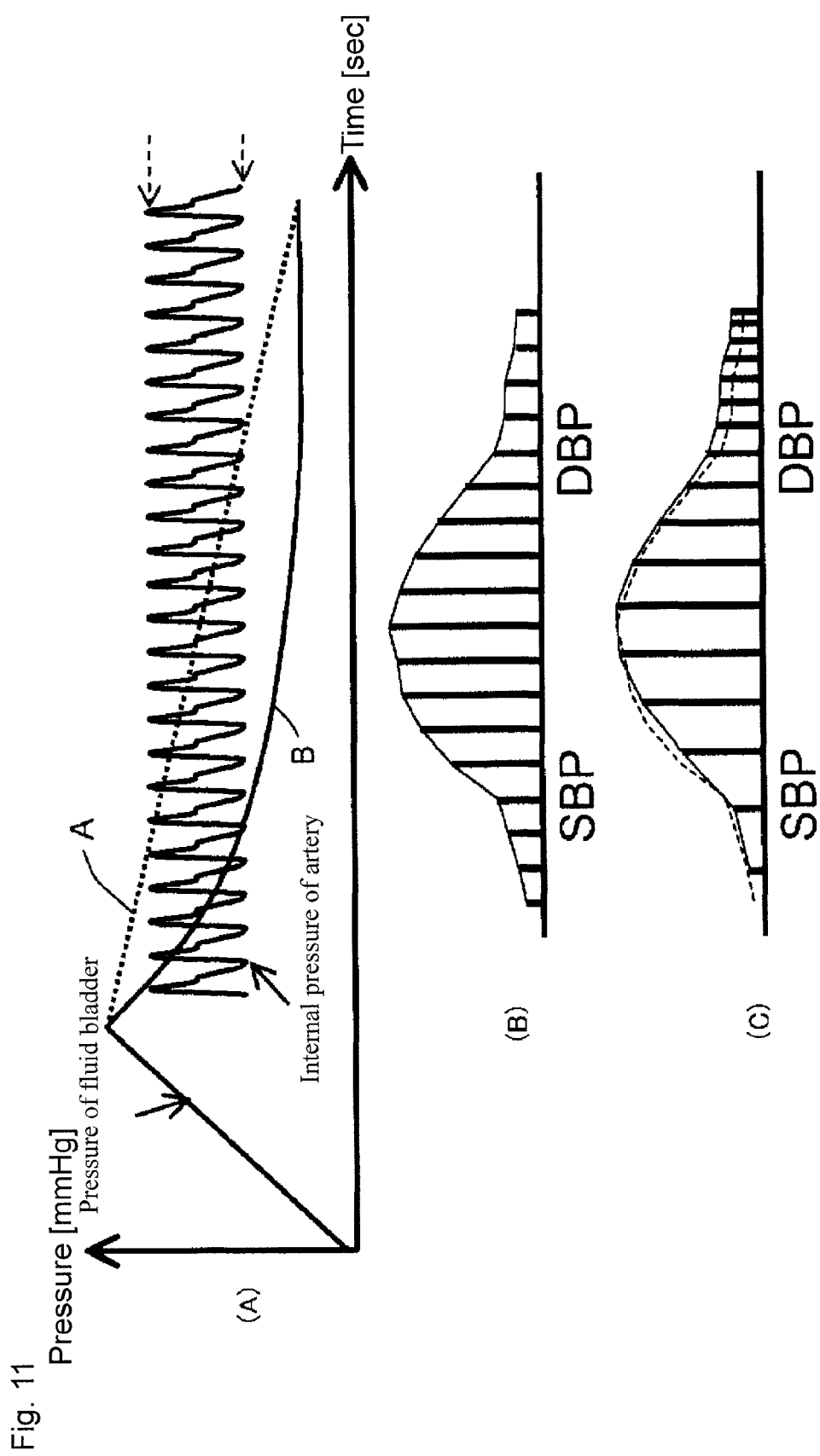
FIG. 11 is a diagram illustrating relationship between a pressure of a fluid bladder and a detected pulse wave amplitude.
Figure 34:
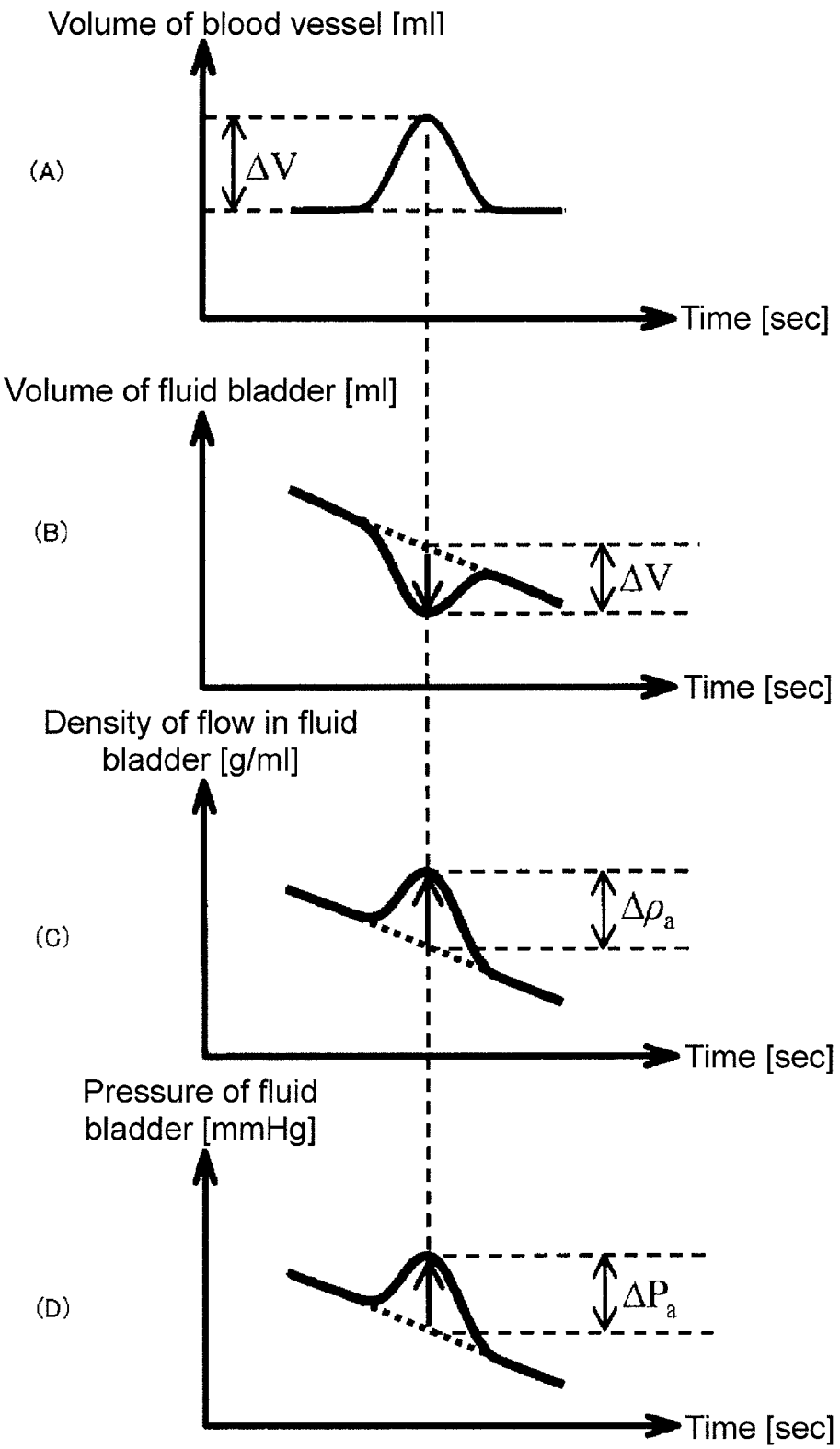
FIG. 34 is a diagram illustrating a volume change of a fluid bladder, a change of a fluid density in the fluid bladder, and a pressure change of the fluid bladder according to a volume change of a blood vessel when the fluid density in the fluid bladder is low in an electronic sphygmomanometer for measuring a blood pressure during depressurizing process of the fluid bladder.
Figure 35:
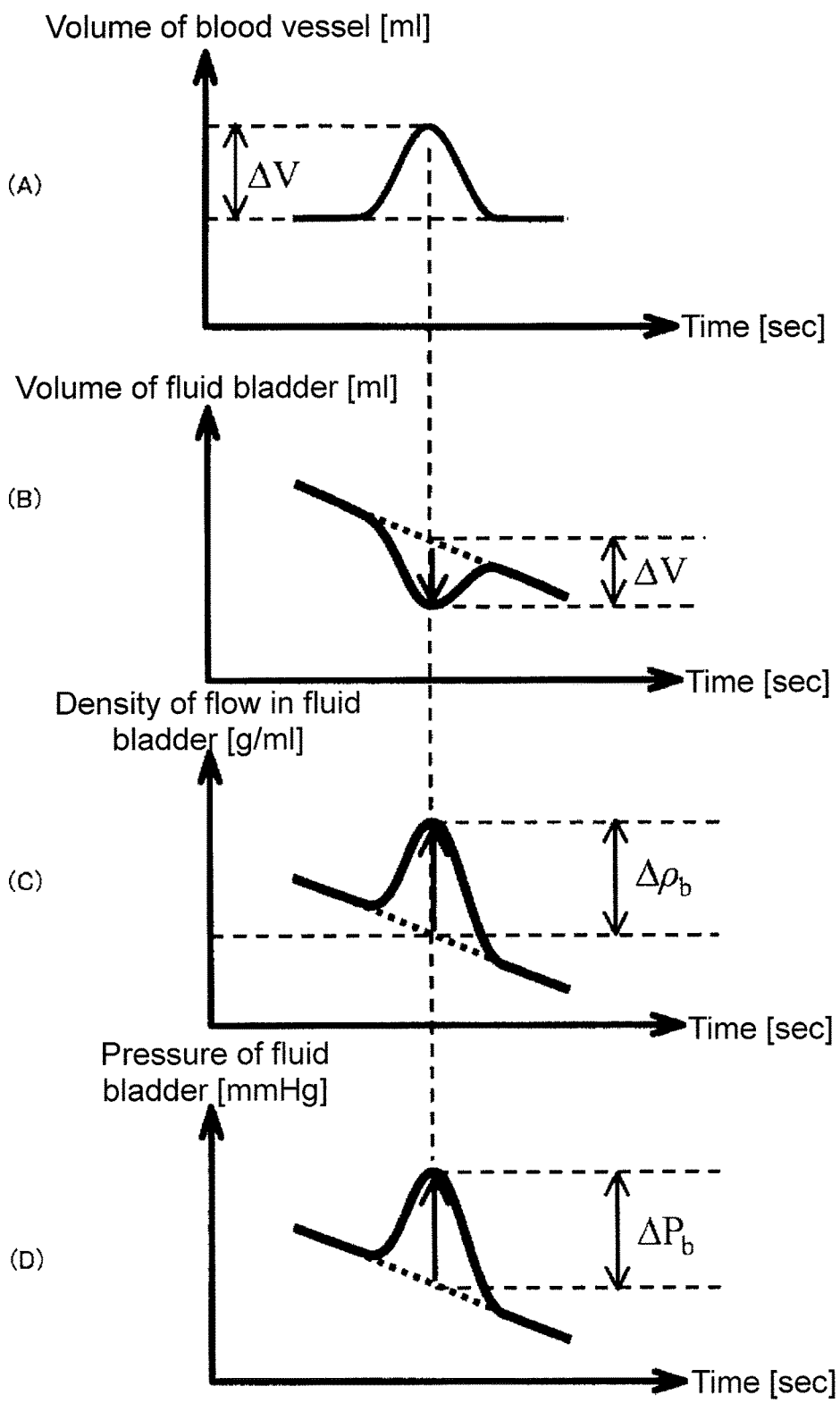
FIG. 35 is a diagram illustrating a volume change of a fluid bladder, a change of a fluid density in the fluid bladder, and a pressure change of the fluid bladder according to a volume change of a blood vessel when the fluid density in the fluid bladder is high in the electronic sphygmomanometer for measuring the blood pressure during depressurizing process of the fluid bladder.
Figure 36:
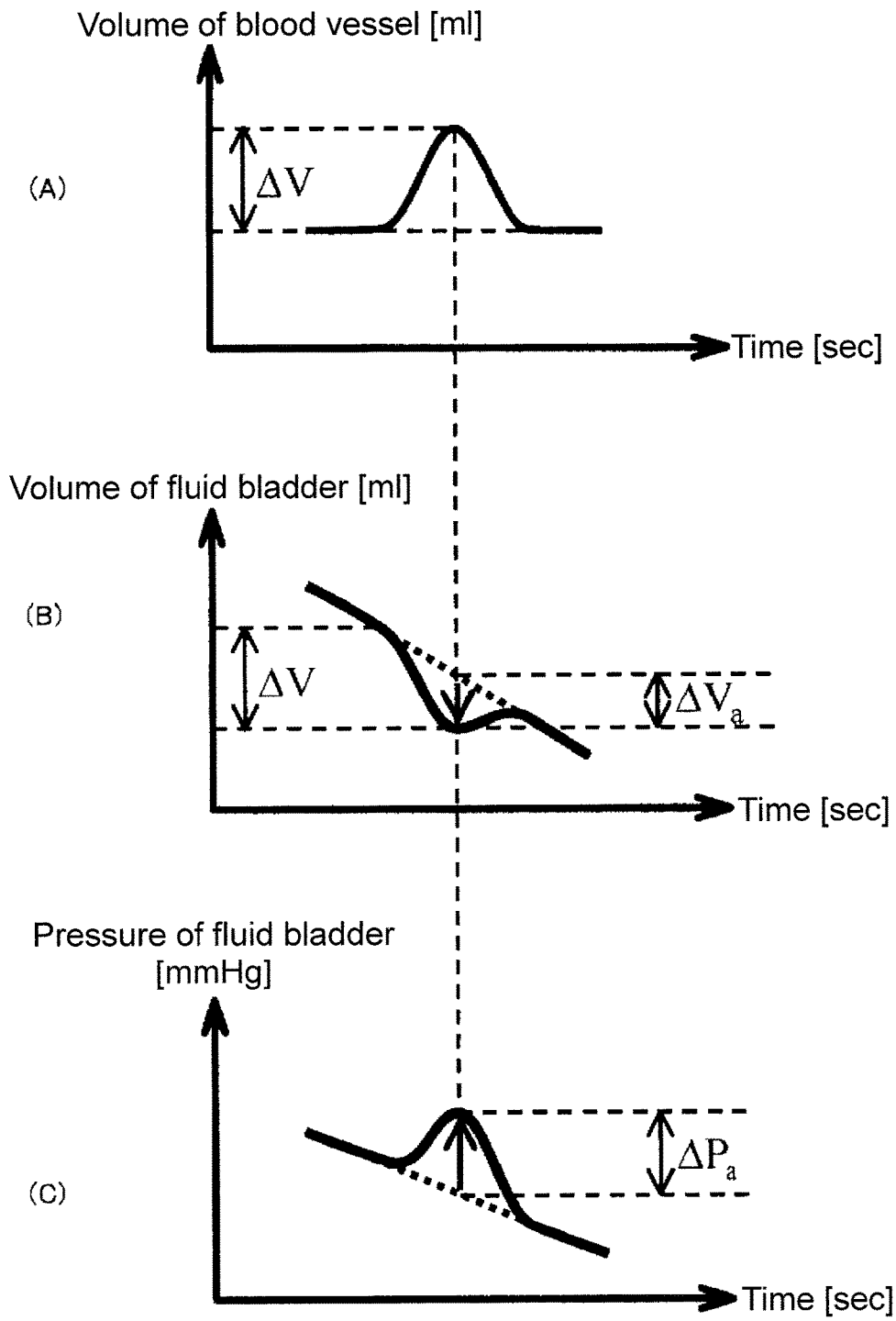
FIG. 36 is a diagram illustrating a volume change of a fluid bladder and a pressure change of the fluid bladder according to a volume change of a blood vessel when a discharge rate of a fluid flowing out of the fluid bladder is fast, i.e., the amount of discharge per unit time is large, in the electronic sphygmomanometer for measuring the blood pressure during depressurizing process of the fluid bladder.
Figure 37:
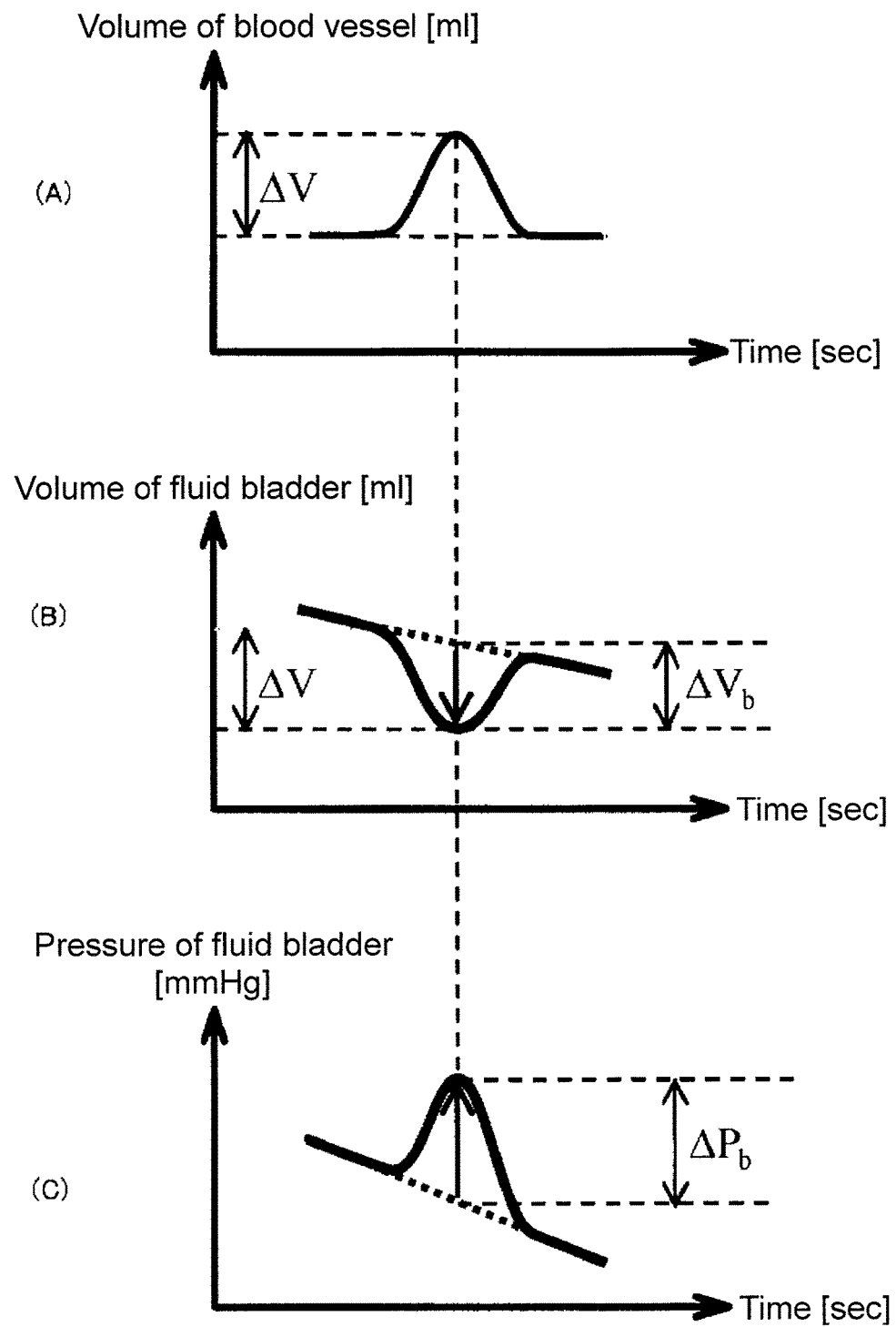
FIG. 37 is a diagram illustrating a volume change of a fluid bladder and a pressure change of the fluid bladder according to a volume change of a blood vessel when a discharge rate of a fluid flowing out of the fluid bladder is slow, i.e., the amount of discharge per unit time is small, in the electronic sphygmomanometer for measuring the blood pressure during depressurizing process of the fluid bladder.
Figure 38A:
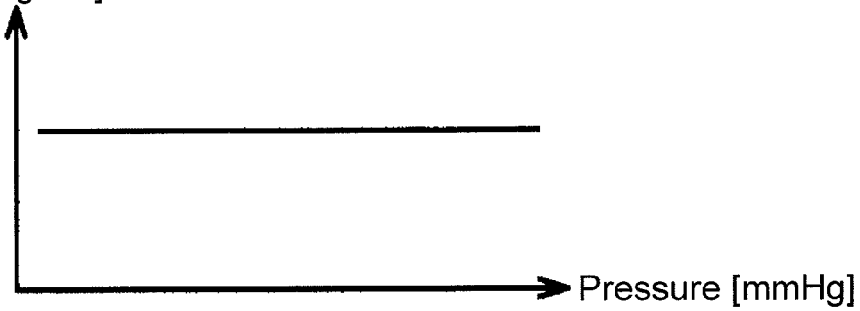
FIG. 38A is a diagram illustrating relationship between a pressure of a fluid bladder and a depressurizing rate in the sphygmomanometer for depressurizing the fluid bladder at a constant rate and measuring the blood pressure during depressurizing process.
Figure 38B:
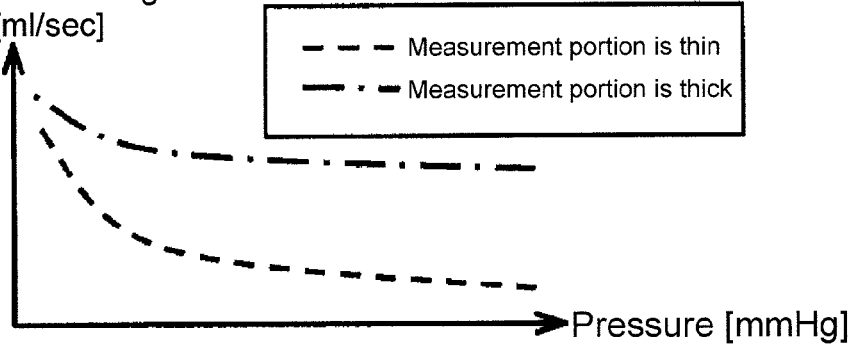
FIG. 38B is a diagram illustrating relationship between a pressure of a fluid bladder and the amount of discharge of a fluid in the sphygmomanometer for depressurizing the fluid bladder at a constant rate and measuring the blood pressure during depressurizing process.
Figure 38C:
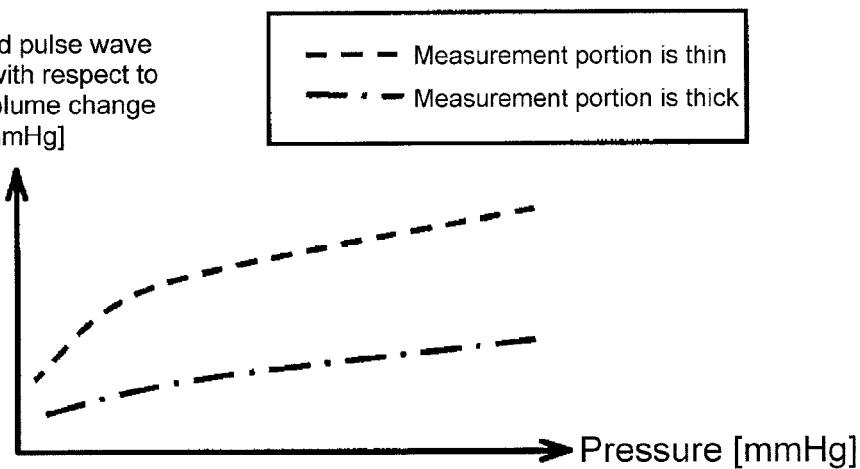
FIG. 38C is a diagram illustrating relationship between a pressure of a fluid bladder and a pressurized pulse wave amplitude value with respect to a constant volume change in the sphygmomanometer for depressurizing the fluid bladder at a constant rate and measuring the blood pressure during depressurizing process.

FIG. 11 is a diagram illustrating relationship between a pressure of the fluid bladder 13 and a detected pulse wave amplitude. (A) shows a pressure change of the fluid bladder 13 according to an elapsed time and a pressure change of a pressure in an artery. In (A), a dotted line A represents a pressure change of the fluid bladder 13 in a case where the pressure of the fluid bladder is controlled to be depressurized with a constant rate in a conventional example. In contrast, in the sphygmomanometer 1 according to the present embodiment, a pressure change of the fluid bladder 13 is represented by a solid line B in a case where the drive voltage Ev is constant, i.e., the fluid bladder is controlled to be depressurized with the gap of the valve 22 being constant. In the sphygmomanometer 1, the drive voltage Ev is constant, i.e., the fluid bladder is controlled to be depressurized with the gap of the valve 22 being constant. Accordingly, a pressure in an artery is measured as shown in (C), whereas in the conventional example, it is measured according to a (depressurizing) pressure change of the fluid bladder 13 as shown in (B). More specifically, in (C), a dotted line represents line segments obtained by connecting each measurement value of the pressure in the artery as shown in (B). As shown in FIGS. 34 and 35, in the conventional sphygmomanometer for controlling the pressure of the fluid bladder so as to depressurize the pressure of the fluid bladder with a constant rate, detection accuracy of a volume change of a blood vessel is lower in a region in which the pressure of the fluid bladder is low than in a region in which the pressure of the fluid bladder is high even when the pressure in the artery is the same. In contrast, as is evident from comparison between (B) and (C), the sphygmomanometer 1 according to the present embodiment has a significantly improved detection accuracy of a volume change of a blood vessel in a region in which the pressure of the fluid bladder 13 is low, compared with the detection accuracy of the conventional sphygmomanometer for controlling the pressure of the fluid bladder so as to depressurize the pressure of the fluid bladder with a constant rate. Likewise, this indicates that detection accuracy of a volume change of a blood vessel is improved in a region in which the pressure is high.

Figure 12:
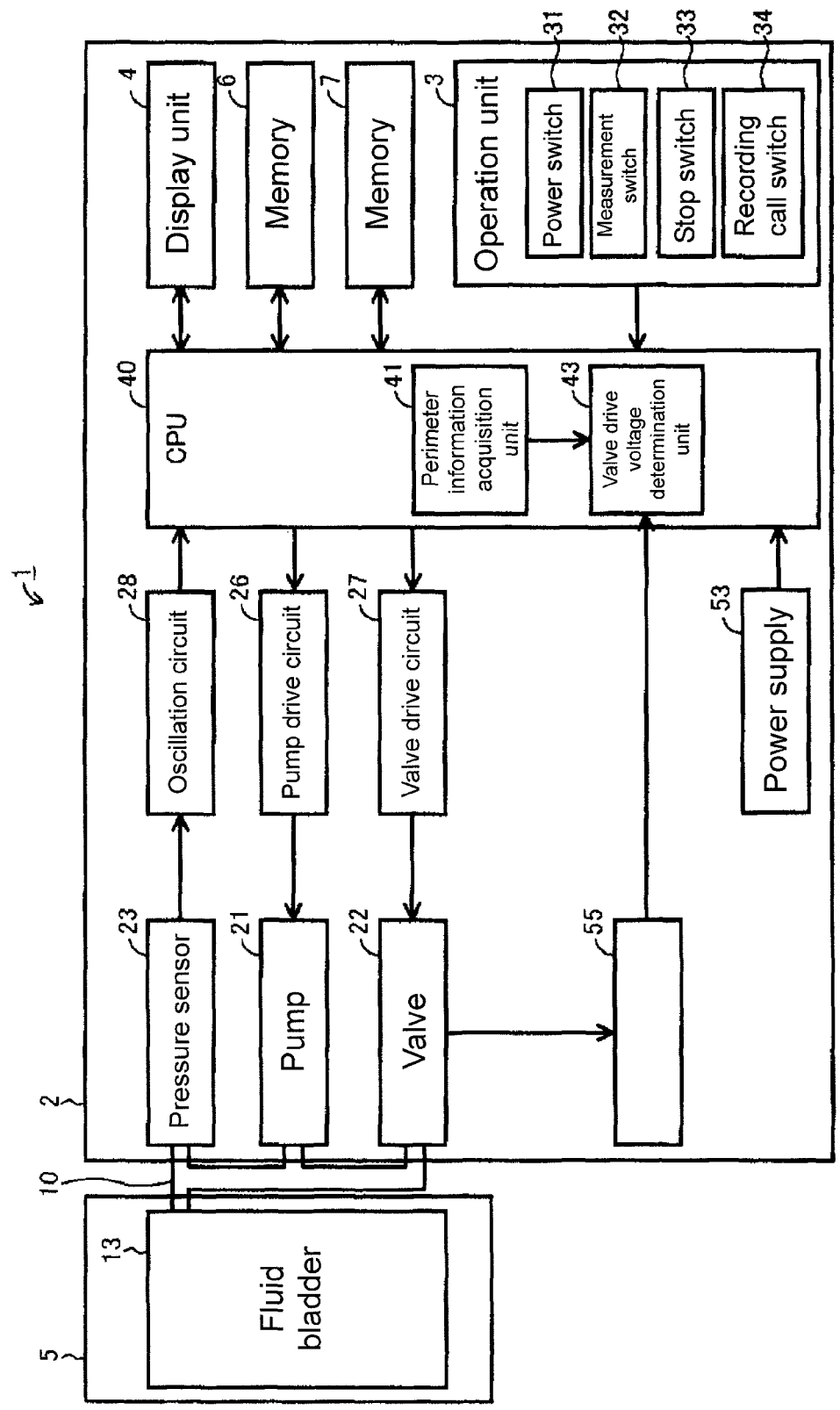
FIG. 12 is a block diagram illustrating another specific example of hardware configuration of a sphygmomanometer serving as a blood pressure measurement device according to the first embodiment.

In the above example, in the depressurizing process in step S111, the CPU 40 maintains the drive voltage Ev at the drive voltage Ev determined by the valve drive voltage determination unit 43 in step S109, i.e., performs control to keep the drive voltage Ev at a constant value. However, the sphygmomanometer 1 may further include a flowmeter 55 for measuring the amount of discharge from the valve 22 as shown in FIG. 12 in addition to the constitution described above, and during depressurizing process, the valve drive voltage determination unit 43 may update the drive voltage Ev so as to maintain proportional relationship between the amount of discharge from the valve 22 and the depressurizing rate. In this case, the CPU 40 performs feedback control to change the drive voltage Ev to a drive voltage Ev determined with particular timing such as a predetermined time interval and maintains the drive voltage Ev. This kind of feedback control achieves almost proportional relationship between the flow amount of the fluid discharged from the fluid bladder 13 and the depressurizing rate. Therefore, the pressurized pulse wave amplitude with respect to a constant volume change of the blood vessel can be made almost constant, and the measurement accuracy can be improved.

[Second Modification]

Figure 13:
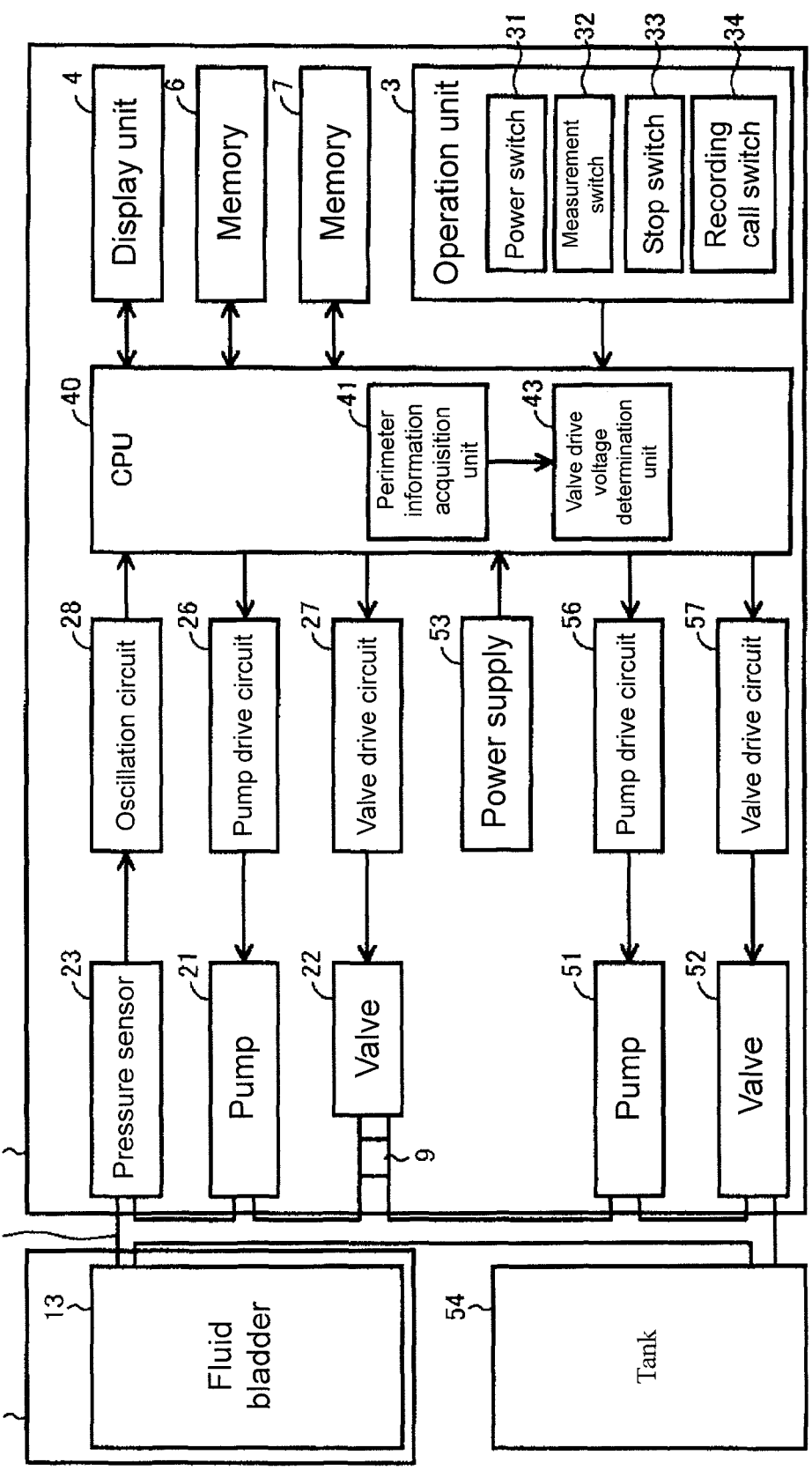
FIG. 13 is a block diagram illustrating a specific example of hardware configuration of a sphygmomanometer according to the second modification of the first embodiment.

A hardware configuration of a sphygmomanometer 1-1, i.e., a modification of the sphygmomanometer 1, will be described with reference to FIG. 13. Referring to FIG. 13, the sphygmomanometer 1-1 further includes a tank 54 storing a non-pressurized fluid and connected to the fluid bladder 13 via the tube 10, in addition to the hardware configuration of the sphygmomanometer 1 as shown in FIG. 1. The tank 54 is connected to the pump 51 and the valve 52. The pump 51 and the valve 52 are respectively connected to a pump drive circuit 56 and a valve drive circuit 57. Further, the pump drive circuit 56 and the valve drive circuit 57 are connected to the CPU 40. The CPU 40 executes a predetermined program stored in the memory 6 based on an operation signal inputted with the operation unit 3. The CPU 40 determines voltages for driving the pump 51 and the valve 52, and outputs control signals to the pump drive circuit 56 and the valve drive circuit 57 according to the determined voltages. When the pump 51 is driven, the non-pressurized fluid stored in the tank 54 flows into the fluid bladder 13 via the tube 10. When the valve 52 is driven, the non-pressurized fluid is discharged from the fluid bladder 13.

A filter 9 is arranged at a portion connecting between the fluid bladder 13 and the valve 22. According to one or more embodiments of the present invention, the filter 9 is made of a material that allows the fluid to pass through but does not allow the non-pressurized fluid to pass through in order to prevent the non-pressurized fluid from leaking out of the valve 22 that injects the fluid into the fluid bladder 13 or discharges the fluid from the fluid bladder 13 when the non-pressurized fluid in the tank 54 moves to the fluid bladder 13.

A specific example of processing executed in response to an operation of the measurement switch 32 in the sphygmomanometer 1-1 will be described with reference to a flowchart of FIG. 14. The processing shown in the flowchart of FIG. 14 is achieved by causing the CPU 40 to execute a predetermined program stored in the memory 6.

Figure 14:
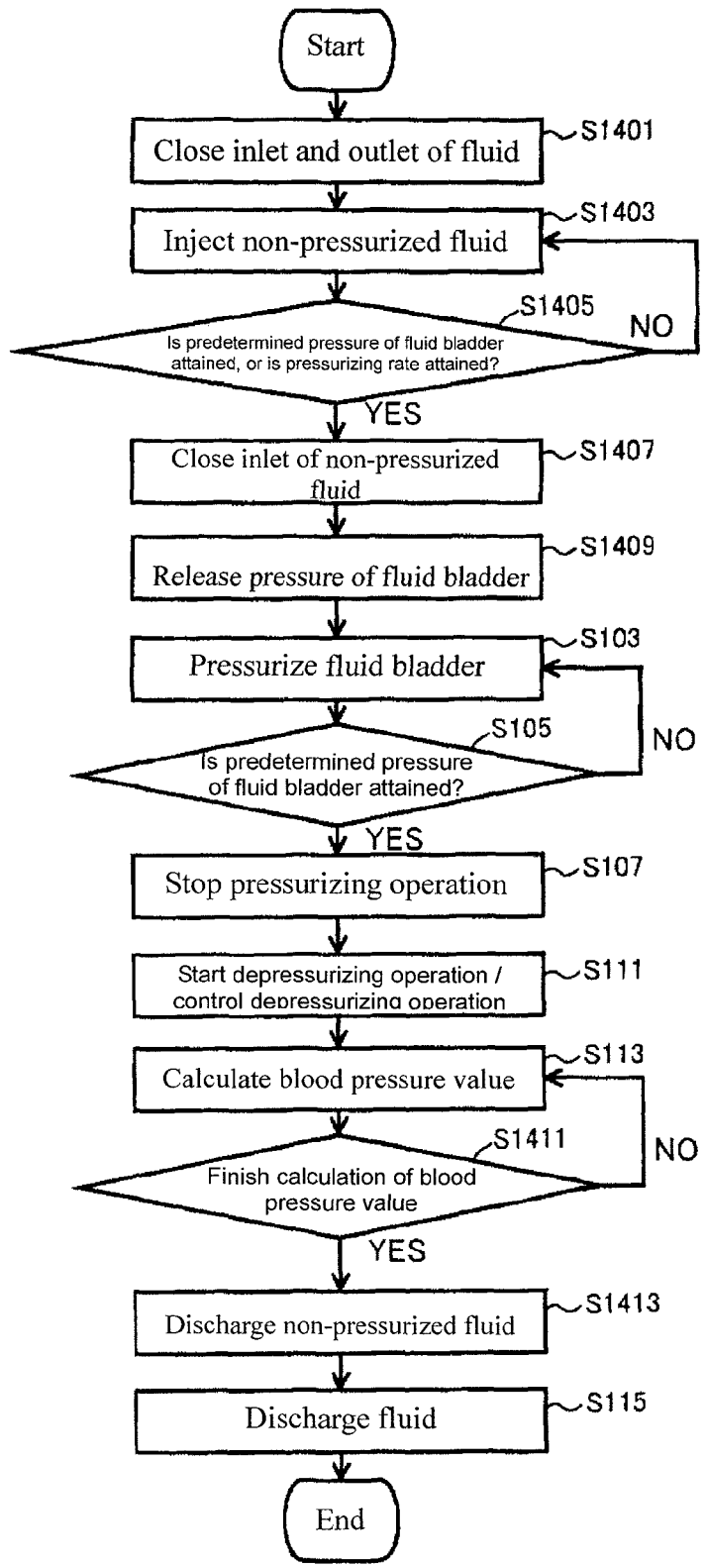
FIG. 14 is a flowchart illustrating a specific example of processing executed in response to an operation of the measurement switch on the sphygmomanometer according to the second modification of the first embodiment.

Referring to FIG. 14, in the modification, in step S1401, the CPU 40 outputs a control signal to the valve drive circuit 27 to close the valve 22, and closes an inlet and an outlet of the fluid into/from the fluid bladder 13. Thereafter, in step S1403, a control signal is outputted to the pump drive circuit 56 to drive the pump 51, and the non-pressurized fluid in the tank 54 is caused to flow into the fluid bladder 13 until the fluid bladder 13 attains a previously defined predetermined pressure or the fluid bladder 13 reaches a predetermined pressurizing rate. That is, the non-pressurized fluid is moved from the tank 54 into the fluid bladder 13. When the internal pressure of the fluid bladder 13 reaches a predetermined pressure or the pressurizing rate of the fluid bladder 13 reaches a predetermined pressurizing rate (YES in step S1405), the CPU 40 outputs a control signal to the valve drive circuit 57 to close the valve 52 in step S1407, and closes the inlet of the non-pressurized fluid into the fluid bladder 13. Then, after closure, the CPU 40 outputs a control signal to the valve drive circuit 27 to open the valve 22 in step S1409, and releases the pressure of the fluid bladder 13. Thereby, a predetermined amount of non-pressurized fluid is injected into the fluid bladder 13, and further, the internal pressure becomes atmospheric pressure.

Thereafter, processings of steps S103 to S107 are executed in the same manner as the processings according to the first embodiment, and the fluid bladder 13 is pressurized until the fluid bladder 13 reaches a predetermined pressure previously defined. In that state, the pressurizing of the fluid bladder 13 is stopped. Then, thereafter, the fluid bladder 13 is depressurized in step S111, and at the same time, the blood pressure value is calculated in step S113.

When the sphygmomanometer 1-1 finishes calculation of the blood pressure value (YES in step S1411), the CPU 40 outputs a control signal to the valve drive circuit 57 to open the valve 52 in step S1413, and discharges the non-pressurized fluid from the fluid bladder 13. Thereafter, in step S115, the valve 22 is opened according to a control signal given by the CPU 40, and the fluid is discharged from the fluid bladder 13.

Figure 33:
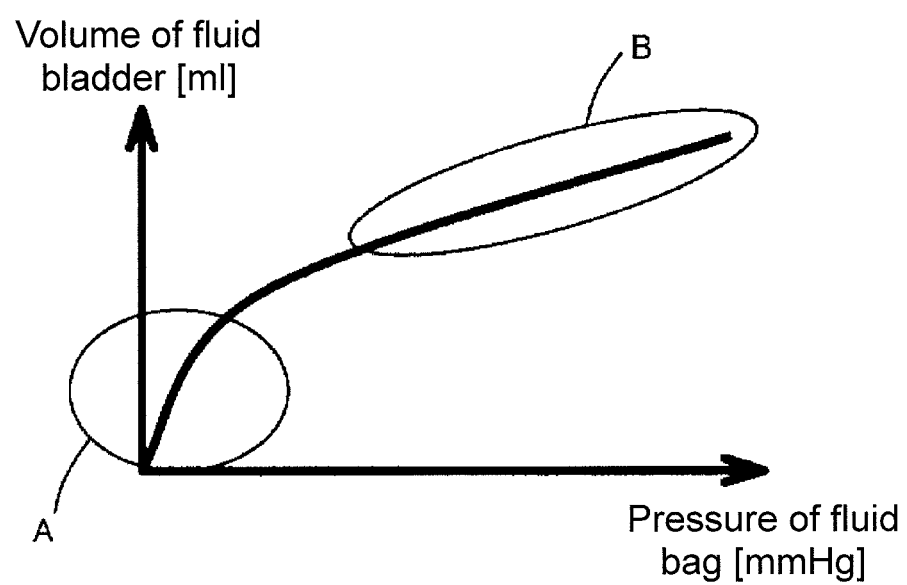
FIG. 33 is a diagram illustrating a character of a fluid bladder.

The sphygmomanometer 1-1 is characterized as follows. Before pressurizing the fluid bladder 13 in the step S103, the sphygmomanometer 1-1 injects a predetermined amount of non-pressurized fluid into the fluid bladder 13 to increase the volume of the fluid bladder 13, thereby reducing the volume of the fluid flowing into the fluid bladder 13. Accordingly, compared with the method for causing all the fluid to flow from an initial state, the sphygmomanometer 1-1 reduces a volume change of the fluid bladder 13 in a region in which the internal pressure of the fluid bladder 13 is low as shown by portion A in FIG. 33, as described above with reference to FIG. 33. Therefore, in the sphygmomanometer 1-1, the detection accuracy of the volume change of the blood vessel can be improved.

Figure 15A:
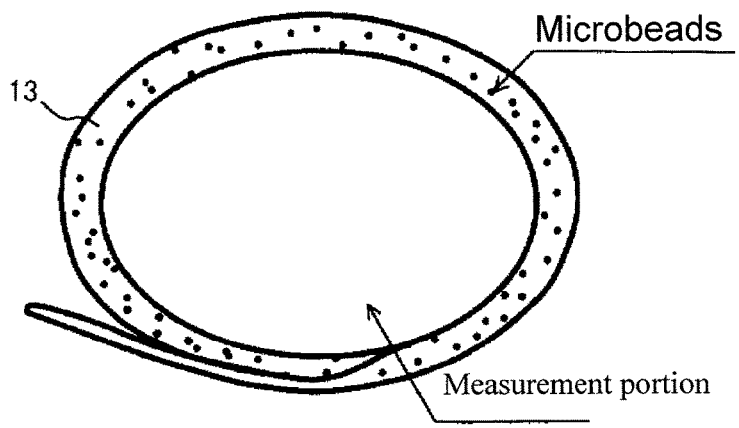
FIG. 15A is a diagram illustrating another specific example of the sphygmomanometer according to the second modification of the first embodiment.
Figure 15B:
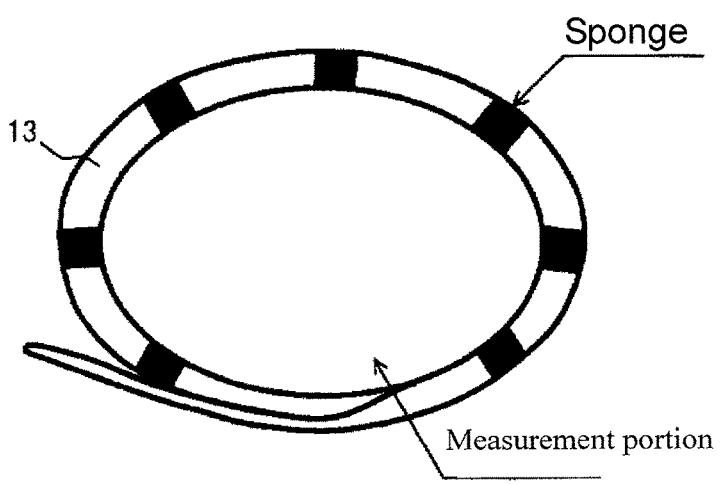
FIG. 15B is a diagram illustrating another specific example of the sphygmomanometer according to the second modification of the first embodiment.
Figure 15C:
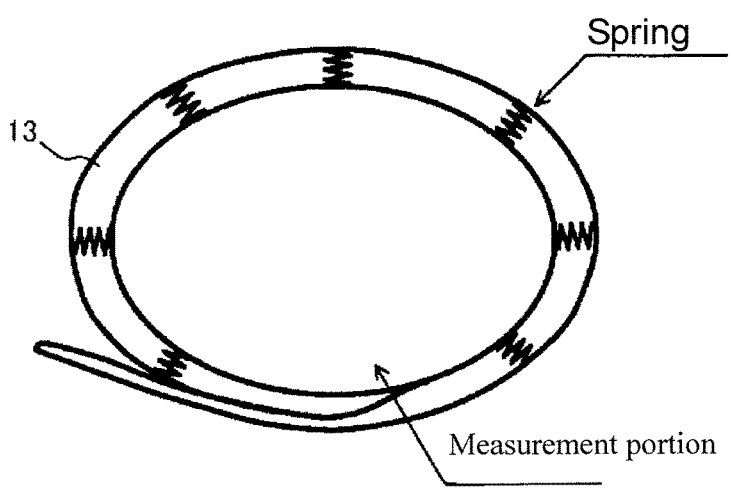
FIG. 15C is a diagram illustrating another specific example of the sphygmomanometer according to the second modification of the first embodiment.

In the above example, the volume change of the volume change of the fluid bladder 13 is reduced in a low pressure region by flowing the non-pressurized fluid into the fluid bladder 13. Alternatively, the volume change may be reduced by previously arranging a filling member in the fluid bladder 13. For example, as shown in FIG. 15A, a gel material such as microbeads serving as the filling member may be previously caused to flow into the fluid bladder 13. Further, for example, as shown in FIGS. 15B and 15C, an elastic material such as a sponge and a spring serving as the filling member may be previously arranged in the fluid bladder 13. When such filling materials are previously arranged in the fluid bladder 13, the volume of the fluid bladder 13 can be increased before the fluid bladder 13 is pressurized. It should be noted that the filling material is not limited to the above gel material and the elastic member. The filling material may be other material. Alternatively, the filling material may be a combination of these materials.

Further, the control of the sphygmomanometer 1 according to the first embodiment during depressurizing process and the constitution of the sphygmomanometer 1-1 according to the modification may be combined. That is, in the processings of the sphygmomanometer 1-1, the processing of step S109 may be performed after the pressurizing of the fluid bladder 13 is stopped in step S107, and the fluid bladder 13 may be depressurized by controlling with the gap of the valve 22 being controlled to be constant. Accordingly, relationship between the flow amount of the fluid discharged from the fluid bladder 13 and the depressurizing rate can be brought closer to proportional relationship. Therefore, the detection accuracy of the volume change of the blood vessel can be made almost constant, and the detection accuracy can be improved.

Second Embodiment

In the second embodiment, a blood pressure measurement device for measuring a blood pressure during pressurizing process of a fluid bladder will be described.

Figure 16:
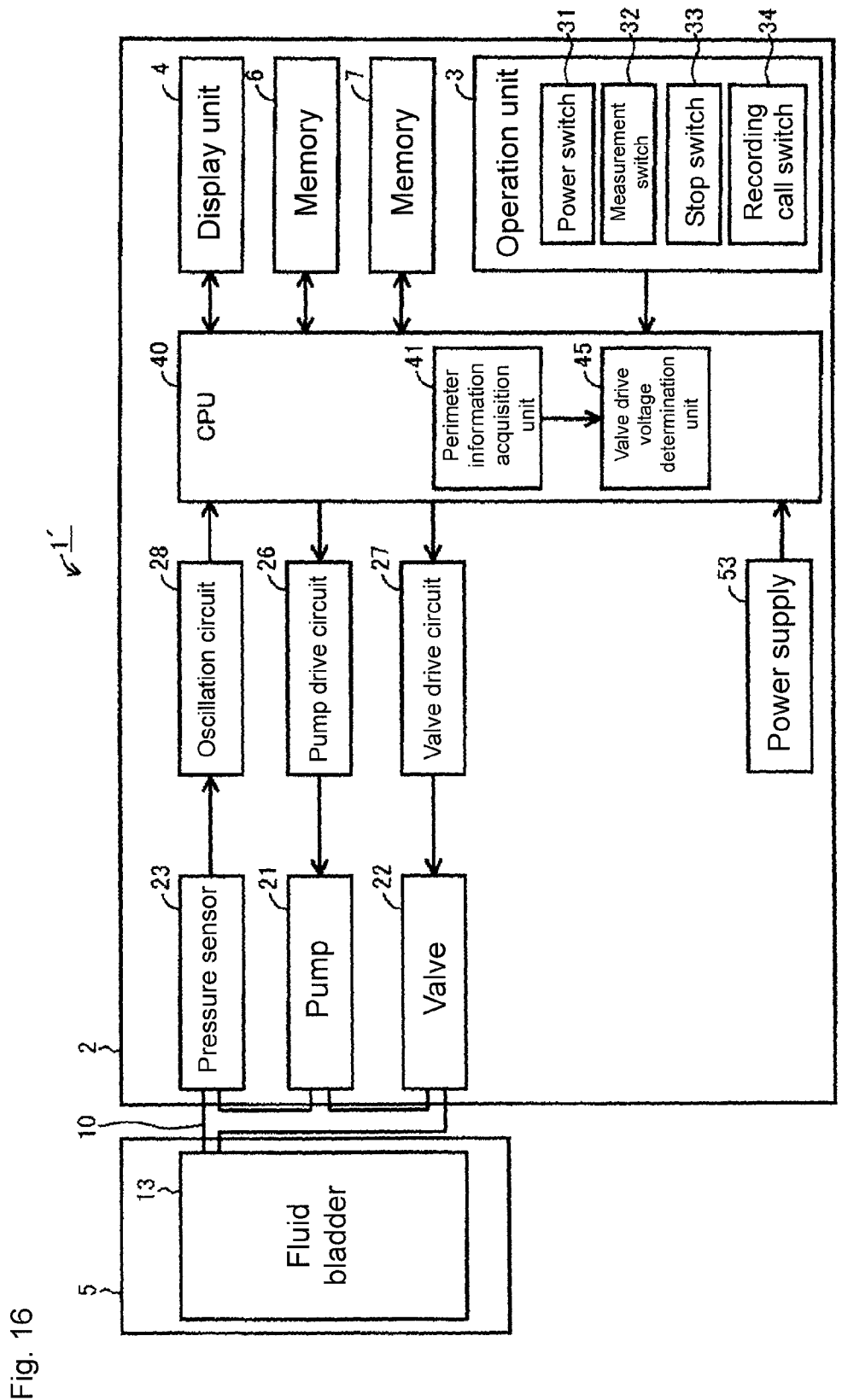
FIG. 16 is a block diagram illustrating a specific example of hardware configuration of a sphygmomanometer serving as a blood pressure measurement device according to the second embodiment.

Referring to FIG. 16, a sphygmomanometer 1' serving as a blood pressure measurement device according to the second embodiment has almost the same hardware configuration as the sphygmomanometer 1 according to the first embodiment as shown in FIG. 1.

In the sphygmomanometer 1' according to the second embodiment, the CPU 40 includes a pump drive voltage determination unit 45 in place of the valve drive voltage determination unit 43. The perimeter information acquisition unit 41 and the pump drive voltage determination unit 45 are formed in the CPU 40 by causing the CPU 40 to execute a predetermined program stored in the memory 6 based on an operation signal inputted from the operation unit 3. The perimeter information acquisition unit 41 obtains perimeter information representing the size of the measurement portion, and inputs the perimeter information into the pump drive voltage determination unit 45. The pump drive voltage determination unit 45 determines a control parameter Ap for controlling a voltage (hereinafter drive voltage Ep) for driving the pump 21 based on the perimeter information. Further, the pump drive voltage determination unit 45 determines the drive voltage Ep based on the control parameter Ap and an internal pressure P, i.e., a pressure of the fluid bladder 13 measured by the pressure sensor 23 inputted via the oscillation circuit 28. CPU 40 outputs, to the pump drive circuit 26, a control signal according to the drive voltage Ep determined by the pump drive voltage determination unit 45. In addition, the CPU 40 executes a predetermined program stored in the memory 6 and outputs a control signal to the valve drive circuit 27 based on an operation signal inputted from the operation unit 3.

A specific example of processing executed in response to an operation of the measurement switch 32 in the sphygmomanometer 1' will be described with reference to a flowchart of FIG. 17. The processing shown in the flowchart of FIG. 17 is achieved by causing the CPU 40 to execute a predetermined program stored in the memory 6.

Figure 17:
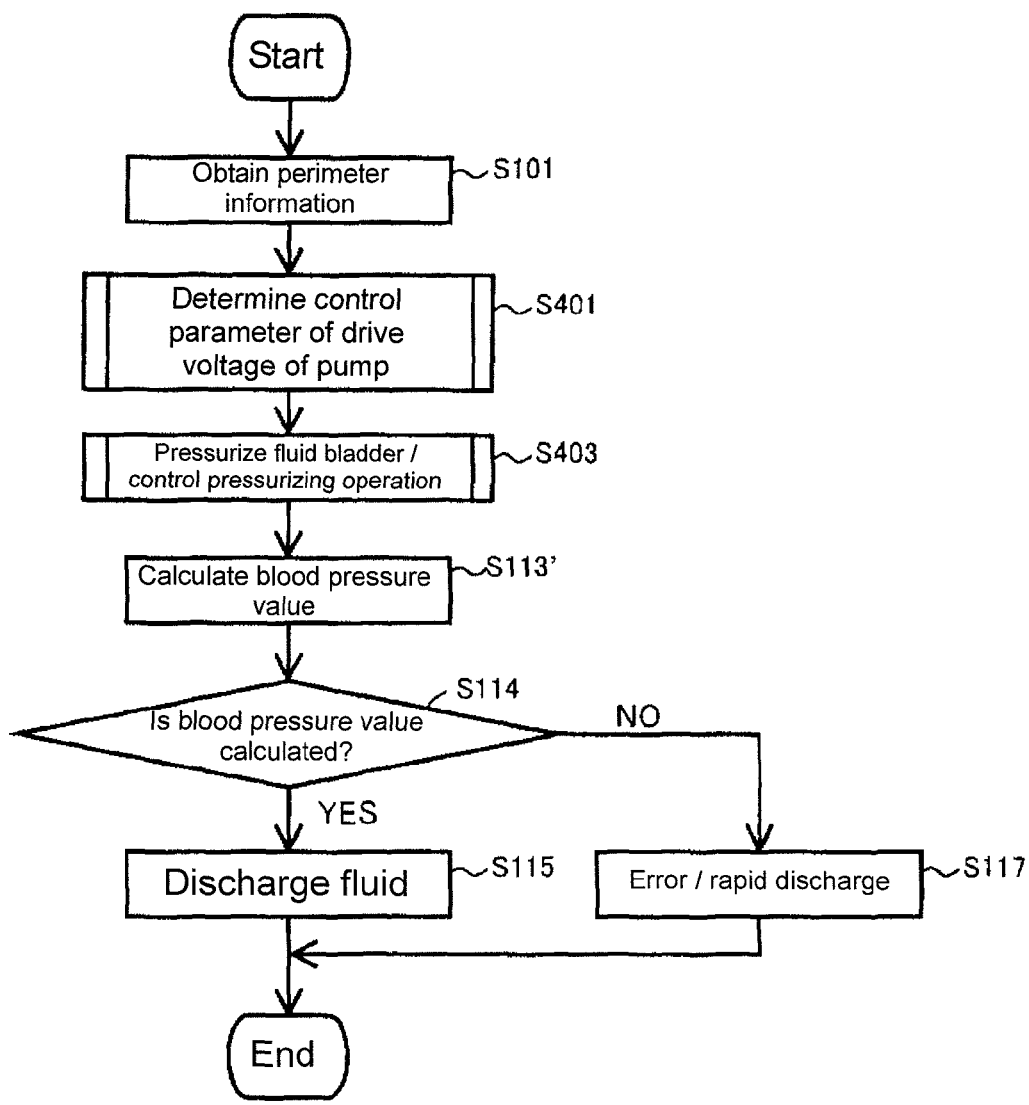
FIG. 17 is a flowchart illustrating a specific example of processing executed in response to an operation of the measurement switch on the sphygmomanometer according to the second embodiment.

Referring to FIG. 17, the perimeter information acquisition unit 41 of the CPU 40 obtains the perimeter information representing the perimeter of the measurement portion, i.e., the size of the measurement portion in the same manner as step S101 of the processing shown in FIG. 2 in the first embodiment. In the second embodiment, as described in the first embodiment with reference to FIGS. 3 and 4, the pressurizing time in which the fluid bladder 13 reaches the predetermined pressure may be obtained as the perimeter information. Alternatively, as described above, when a cloth (not shown) for wrapping the fluid bladder 13 around the measurement portion includes a slide resistor, the perimeter information may be obtained from a resistance value obtained from the slide resistor.

In step S401, the pump drive voltage determination unit 45 of the CPU 40 determines the control parameter Ap for controlling the drive voltage Ep of the pump 21 based on the perimeter information obtained in step S101.

In step S403, the CPU 40 uses the internal pressure P and the control parameter Ap determined in step S401 to determine the drive voltage Ep, and outputs a control signal for driving the pump 21 with the determined drive voltage Ep to the pump drive circuit 26, thereby pressurizing the fluid bladder 13. It should be noted that in step S403, the CPU 40 performs the above processings with predetermined timing to determine the drive voltage Ep according to an internal pressure change of the fluid bladder 13. Examples of predetermined timings include a predetermined time interval, a timing in which the pressure of the fluid bladder 13 reaches a predetermined pressure, and the like. Then, in step S113', the CPU 40 extracts a vibrational component caused by a volume change of an artery, superposed on the internal pressure of the fluid bladder 13, obtained during compressing process, and calculates a blood pressure value according to a predetermined calculation. It should be noted that in a case where the pressurizing rate is too fast in step S403 to calculate the blood pressure value in step S113', or on the contrary, the pressurizing rate is too slow in step S403 to pressurize the fluid (NO in step S114), the CPU 40 determines an occurrence of an error in step S117, and outputs a control signal to the valve drive circuit 27 to open the valve 22 so as to rapidly discharge the fluid from the fluid bladder 13. In the other case, i.e., where the blood pressure value is calculated in step S113' (YES in step S114), the valve 22 is opened according to the control signal given by the CPU 40 in step S115, so that the fluid is discharged from the fluid bladder 13.

The determination of the control parameter Ap in the pump drive voltage determination unit 45 in step S401 and the determination of the drive voltage Ep in the pump drive voltage determination unit 45 in step S403 will be described.

Figure 18:
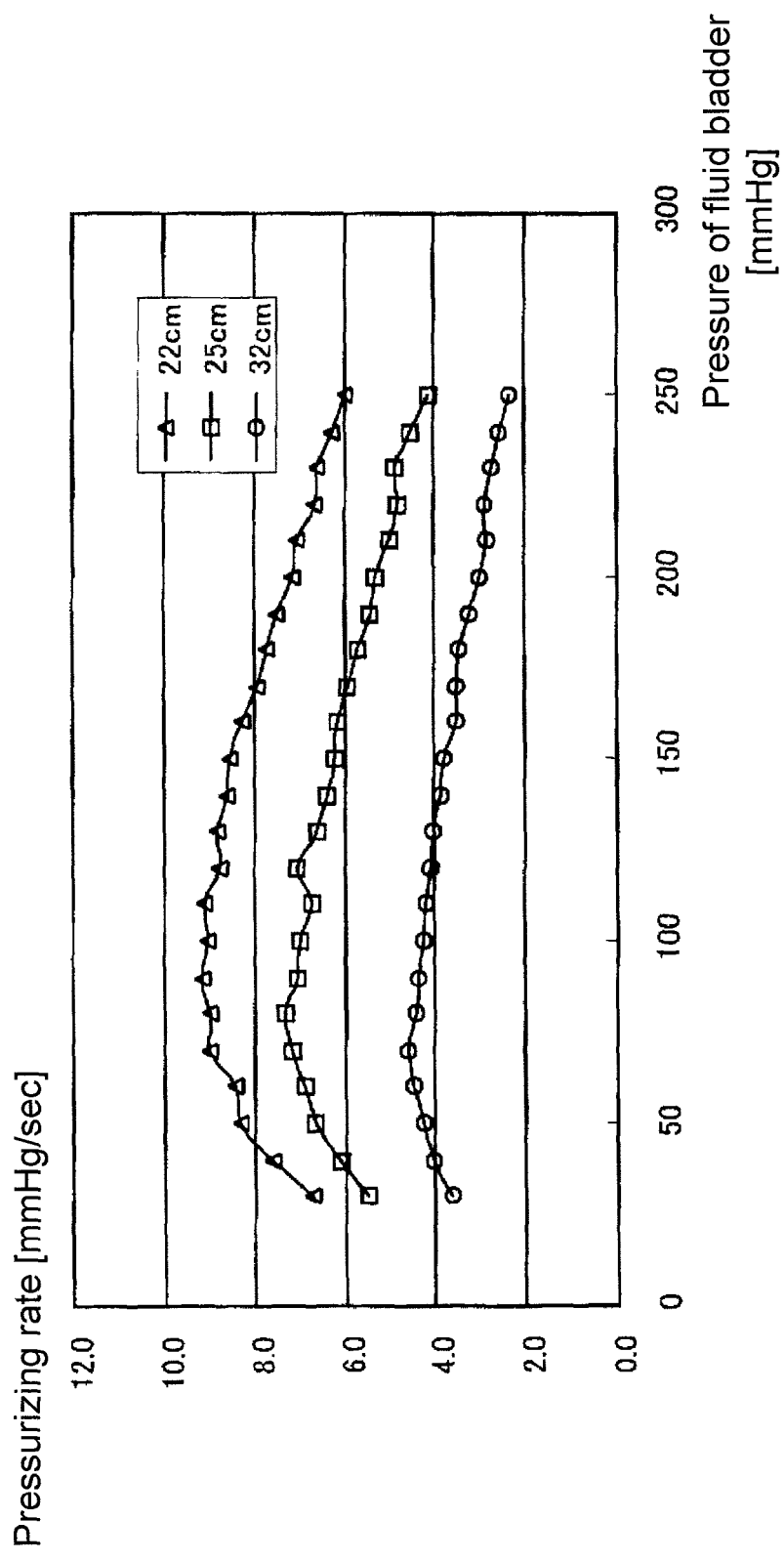
FIG. 18 is a diagram illustrating, for each perimeter of a measurement portion, a relationship between a pressure of a fluid bladder and a pressurizing rate when a drive voltage of a pump is kept constant.

FIG. 18 is a diagram illustrating, for each perimeter of a measurement portion, a relationship between a pressure of the fluid bladder 13 and a pressurizing rate when a drive voltage Ep is kept constant. Referring to FIG. 18, the smaller the perimeter of the measuring portion is, the larger the overall pressurizing rate is. On the other hand, the larger the perimeter of the measuring portion is, the smaller the overall pressurizing rate is. Further, the smaller the perimeter of the measuring portion is, the larger the degree of change of the pressurizing rate is. The larger the perimeter of the measuring portion is, the smaller the degree of change of the pressurizing rate is. In other words, it is understood from the relationship shown in FIG. 18 that the perimeter of the measuring portion is a parameter for determining the drive voltage Ep.

Accordingly, in step S401, the pump drive voltage determination unit 45 uses the relationship as shown in FIG. 18 to determine the control parameter Ap. As a specific example, the pump drive voltage determination unit 45 determines the control parameter Ap by substituting the perimeter information obtained in step S101 or step S201 into the following expression (3).

Control parameter $Ap = \alpha' \times \text{perimeter information} + \beta'$  Expression (3)

Figure 19:
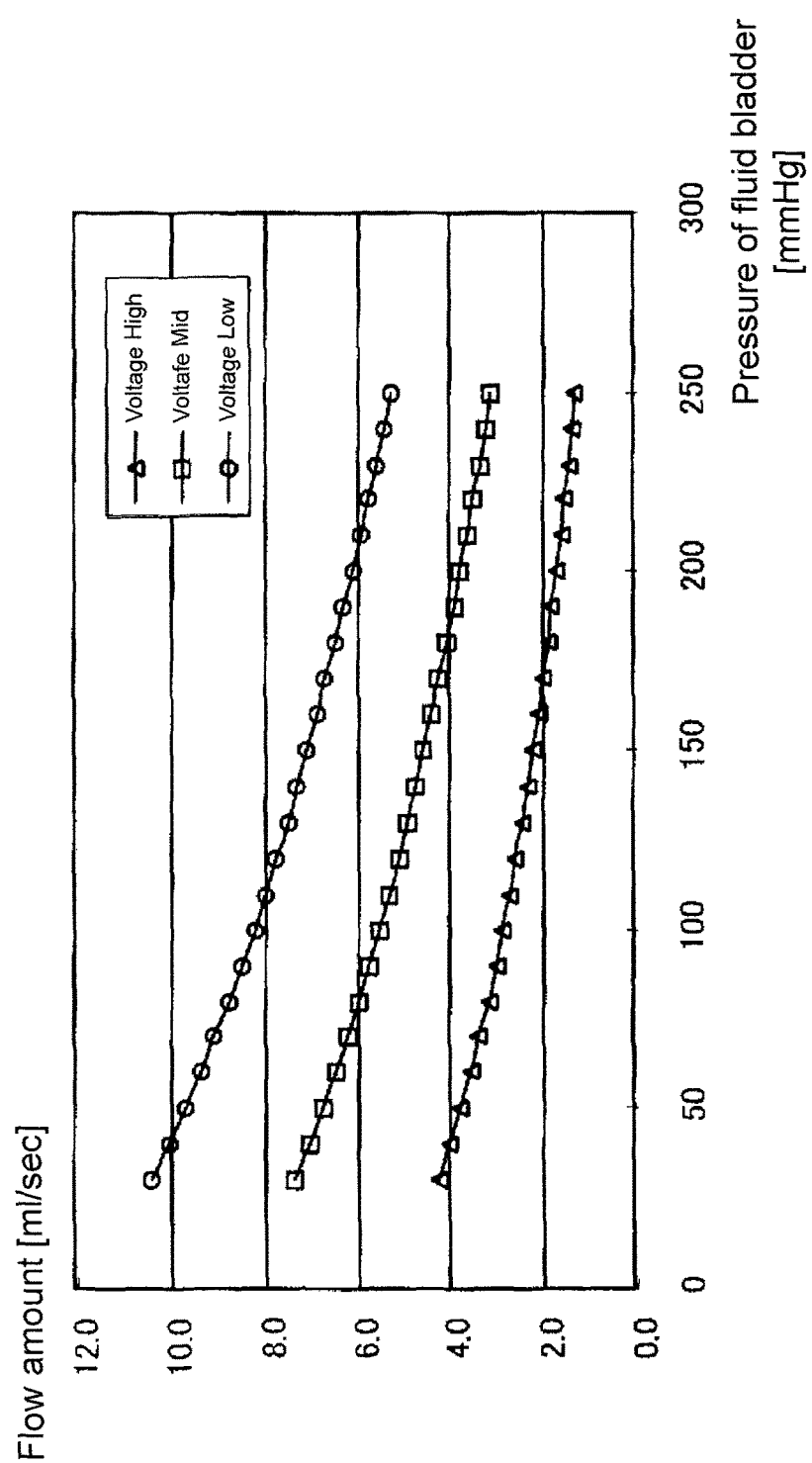
FIG. 19 is a diagram illustrating, for each drive voltage of a pump, a relationship between a pressure of a fluid bladder and the amount of inflow of a fluid into a the fluid bladder per unit time.

FIG. 19 is a diagram illustrating, for each drive voltage Ep, a relationship between a pressure of the fluid bladder 13 and an inflow rate of the fluid into the fluid bladder 13, i.e., the amount of inflow per unit time, in a case where the perimeter of the measuring portion is fixed to a certain size. Referring to FIG. 19, as the drive voltage Ep is larger (higher), i.e., driving force of the pump 21 is larger, the overall inflow rate is large. On the contrary, as the drive voltage Ep is smaller (lower), i.e., driving force of the pump 21 is smaller, the overall inflow rate is small. Further, the larger the drive voltage Ep is, the larger the degree of change of the inflow rate is. The smaller the drive voltage Ep is, the smaller the degree of change of the inflow rate is.

Accordingly, in step S403, the pump drive voltage determination unit 45 uses the relationship as shown in FIG. 19 to determine the drive voltage Ep. As a specific example, the pump drive voltage determination unit 45 determines the drive voltage Ep by substituting the control parameter Ap and the internal pressure P of the fluid bladder 13 thus determined into the following expression (4).

Drive voltage $Ep = \text{control parameter } Ap \times \text{internal pressure } P$  Expression (4)

Figure 20:
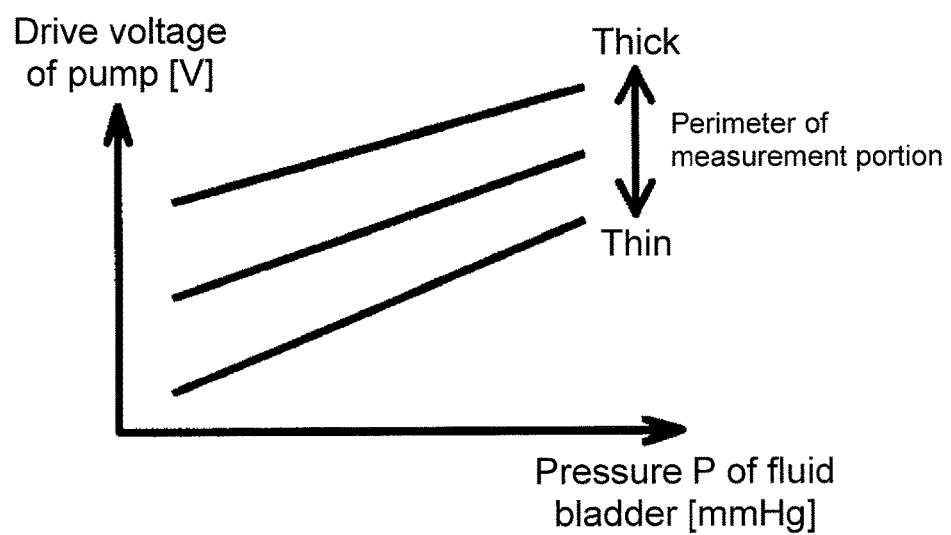
FIG. 20 is a diagram illustrating relationship between a drive voltage of a pump, pressure of the fluid bladder and a perimeter of a measurement portion, which is determined by the sphygmomanometer according to the second embodiment.

When the above expressions (3), (4) are used in steps S401, S403, the drive voltage Ep is determined as a magnitude in proportional to the perimeter of the measuring portion and the internal pressure P as shown in FIG. 20. Further, in step S403, when the pressure of the fluid bladder 13 reaches the predetermined pressure in step S105, the drive voltage Ep is determined as described above, and further, pressurizing process is performed. Likewise, the drive voltage Ep may be thereafter determined (updated) with a predetermined timing. When the drive voltage Ep is determined with the above timing, the pump drive voltage determination unit 45 determines the drive voltage Ep by substituting the internal pressure P into the expression (3).

More specifically, according to one or more embodiments of the present invention, the drive voltage Ep has such magnitude achieving a pressurizing rate such that the number of pulses detected between the systolic blood pressure and the diastolic blood pressure during pressurizing process is equal to or more than a predetermined number. According to one or more embodiments of the present invention, the above "predetermined number" is five. According to one or more embodiments of the present invention, the pressurizing rate allowing five or more pulses to be measured between the systolic blood pressure and the diastolic blood pressure during pressurizing process is about 3 mmHg/sec to 13 mmHg/sec. Accordingly, the coefficients $\alpha'$, $\beta'$ of the above expression (3) can be such values that cause the pressurizing rate of the fluid bladder 13 from the calculation of the systolic blood pressure to the calculation of the diastolic blood pressure to be in a range of target pressurizing rate, i.e., about 3 mmHg/sec to 13 mmHg/sec. These coefficients $\alpha'$, $\beta'$ can be obtained through, for example, experiments, the relationship as shown in FIG. 19, and the like, and is assumed to be stored in the memory 6 of the sphygmomanometer 1' in advance. In the above example, the control parameter Ap is determined by inputting the obtained perimeter information into the above expression (3) in step S401. Alternatively, instead of the expression (3), the memory 6 may store a table defining relationship between the perimeter information and the control parameter Ap, and the pump drive voltage determination unit 45 may read the control parameter Ap corresponding to the obtained perimeter information from the table. Likewise, instead of the expression (4), the memory 6 may store a table defining relationship between the perimeter information and the drive voltage Ep, and the pump drive voltage determination unit 45 may read the drive voltage Ep corresponding to the obtained perimeter information from the table.

Figure 21A:
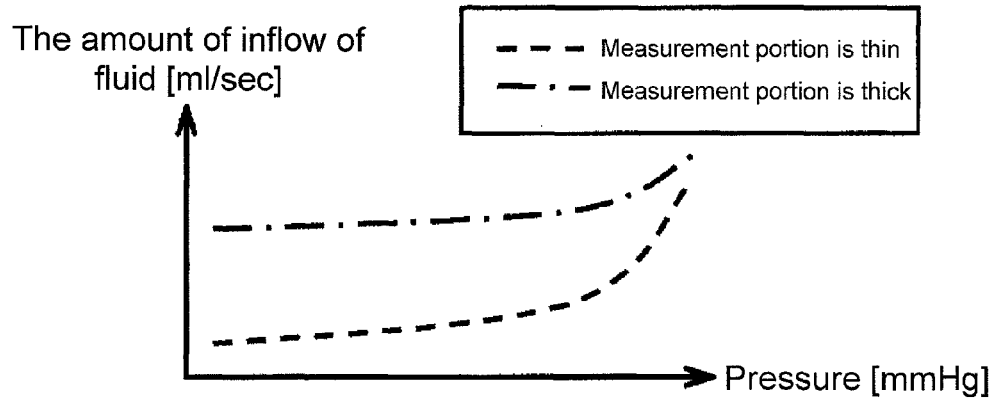
FIG. 21A is a diagram illustrating relationship between a pressure of a fluid bladder and the amount of inflow of a fluid into the fluid bladder per unit time in the sphygmomanometer according to the second embodiment.
Figure 21B:
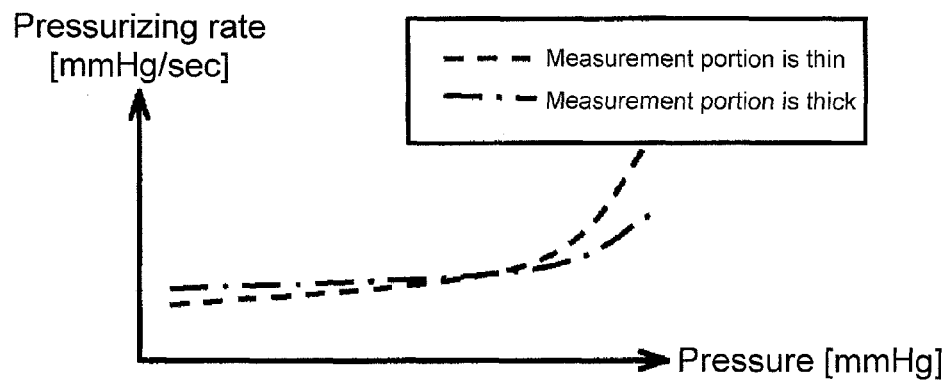
FIG. 21B is a diagram illustrating relationship between a pressure of a fluid bladder and a pressurizing rate of the fluid bladder in the sphygmomanometer according to the second embodiment.
Figure 21C:
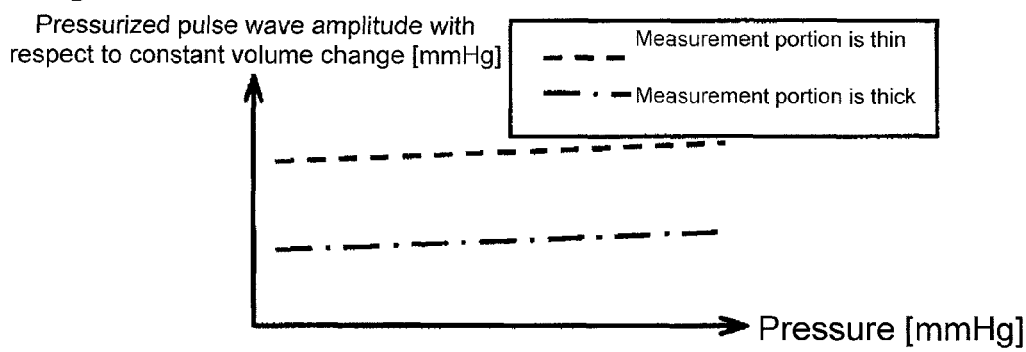
FIG. 21C is a diagram illustrating relationship between a pressure of a fluid bladder and a pressurized pulse wave amplitude value with respect to a constant volume change in the sphygmomanometer according to the second embodiment.

In step S403, the CPU 40 updates the drive voltage Ep according to the internal pressure P while pressurizing the fluid bladder 13. Accordingly, during pressurizing process, the amount of inflow of the fluid into the fluid bladder 13 per unit time is controlled as shown in FIG. 21A according to the pressure of the fluid bladder 13. At this occasion, the pressurizing rate of the fluid bladder 13 changes (increases) as shown in FIG. 21B according to the pressure change of the fluid bladder 13. Accordingly, the sphygmomanometer 1' achieves almost proportional relationship between the flow amount of the fluid injected into the fluid bladder 13 per unit time and the pressurizing rate of the fluid bladder 13. Therefore, the measurement accuracy can be improved. Therefore, as shown in FIG. 21C, regardless of the pressure change of the fluid bladder 13, the pressurized pulse wave amplitude with respect to a constant volume change can be a constant value according to the perimeter of the measuring portion.

Figure 22:
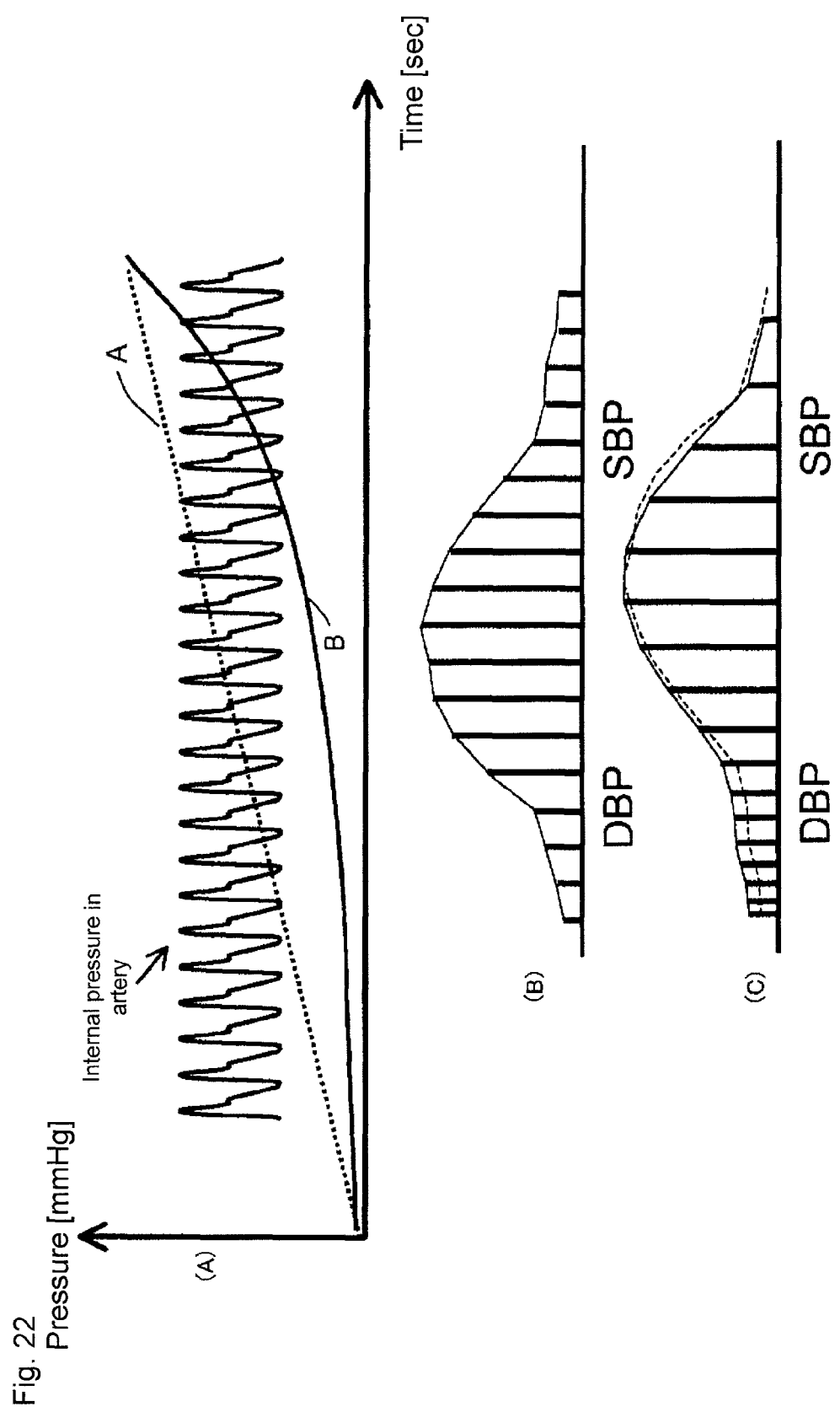
FIG. 22 is a diagram illustrating relationship between a pressure of a fluid bladder and a detected pulse wave amplitude.
Figure 39:
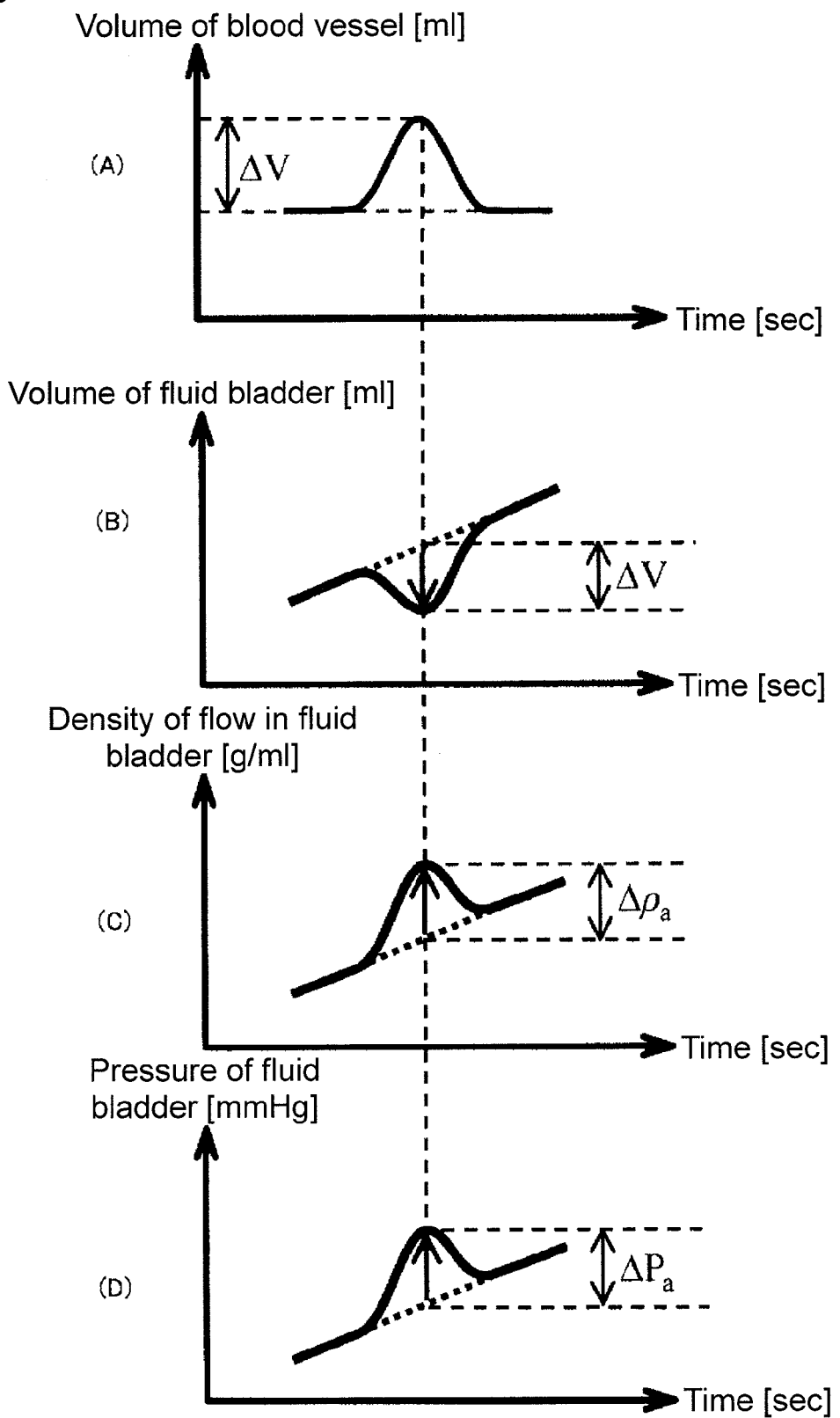
FIG. 39 is a diagram illustrating a volume change of a fluid bladder, a change of a fluid density in the fluid bladder, and a pressure change of the fluid bladder according to a volume change of a blood vessel when the fluid density in the fluid bladder is low in an electronic sphygmomanometer for measuring a blood pressure during pressurizing process of the fluid bladder.
Figure 40:
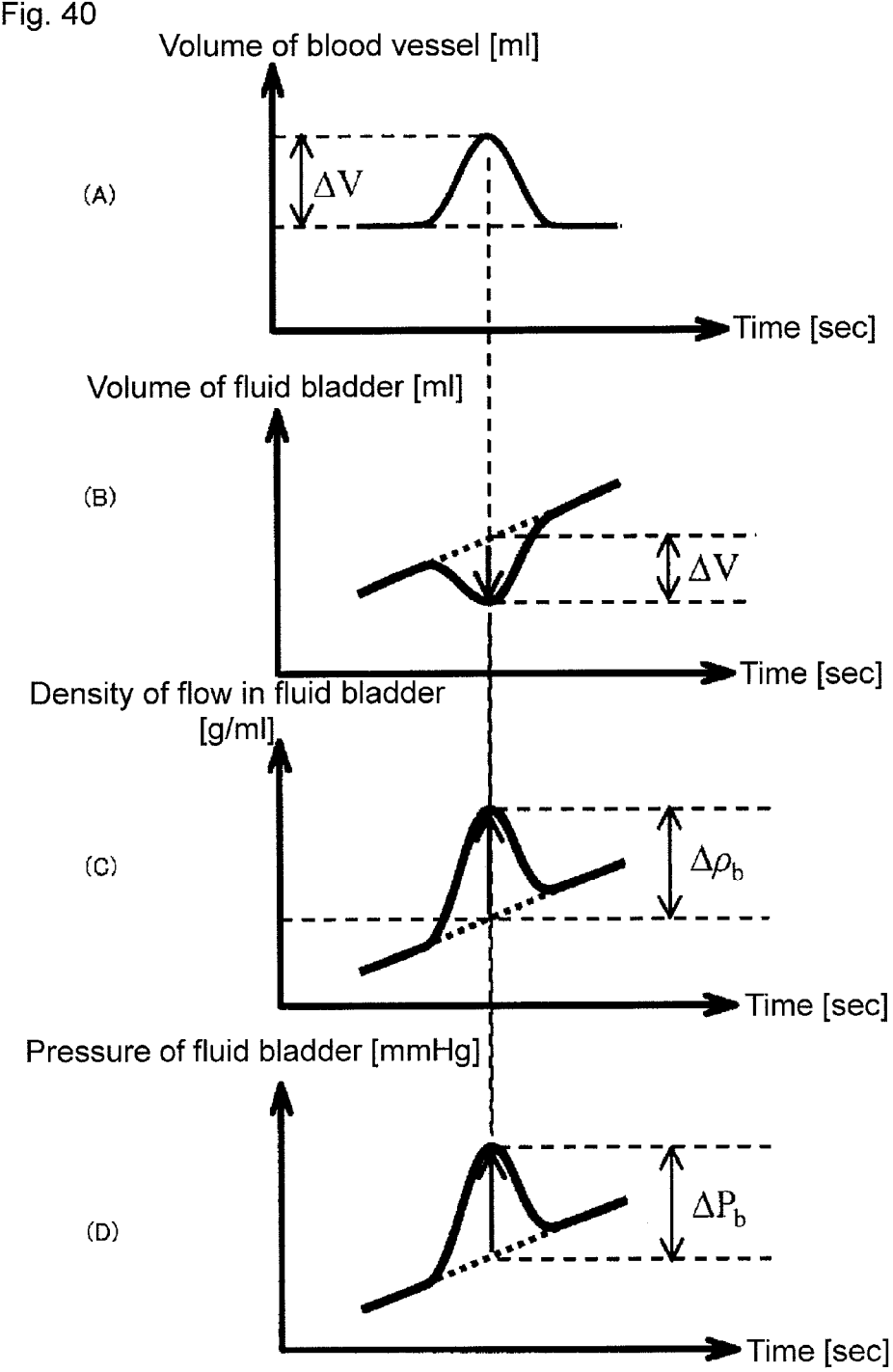
FIG. 40 is a diagram illustrating a volume change of a fluid bladder, a change of a fluid density in the fluid bladder, and a pressure change of the fluid bladder according to a volume change of a blood vessel when the fluid density in the fluid bladder is high in the electronic sphygmomanometer for measuring the blood pressure during pressurizing process of the fluid bladder.
Figure 41:
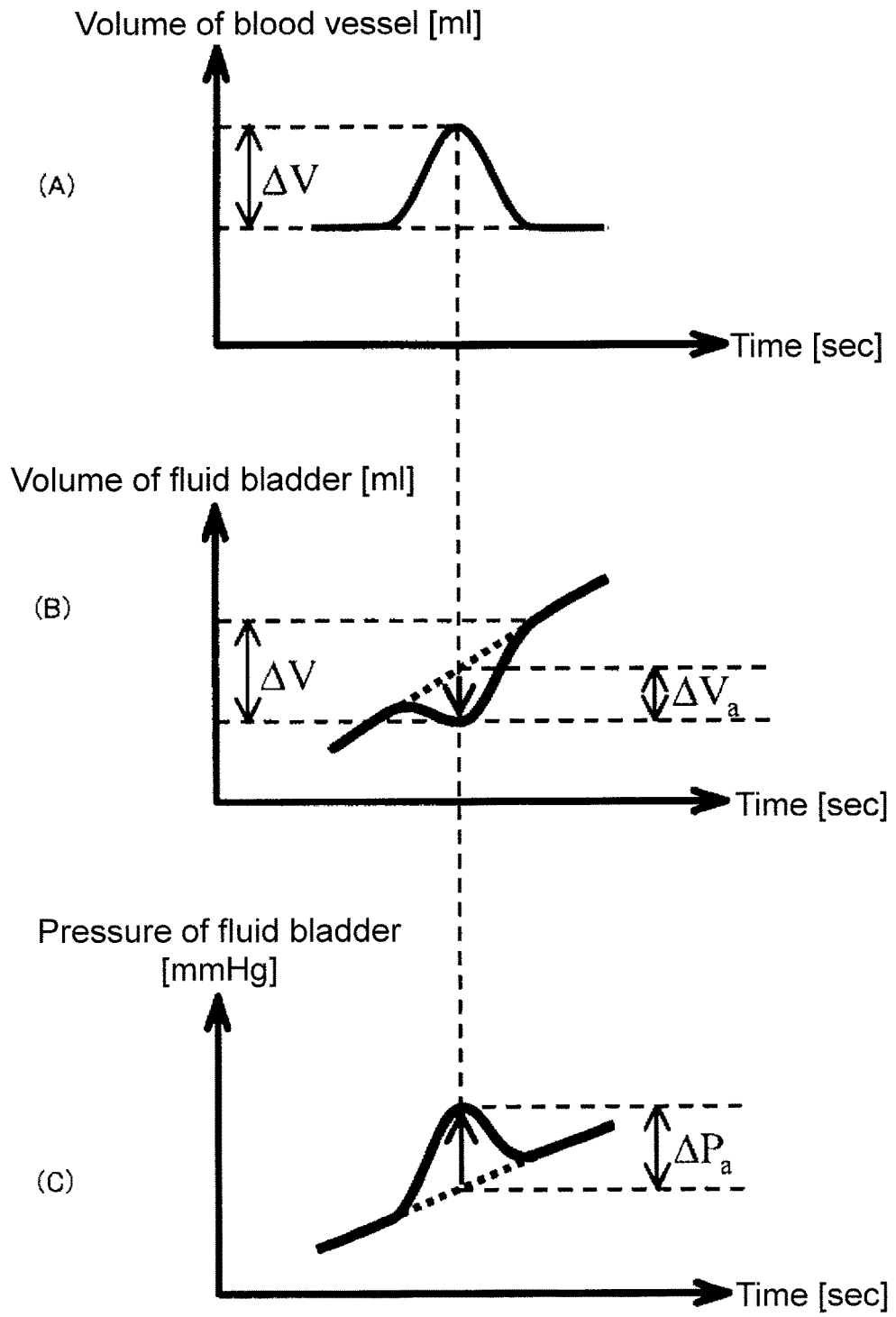
FIG. 41 is a diagram illustrating a volume change of a fluid bladder and a pressure change of the fluid bladder according to a volume change of a blood vessel when an inflow of a fluid flowing into the fluid bladder is fast, i.e., the amount of inflow per unit time is large, in the electronic sphygmomanometer for measuring the blood pressure during pressurizing process of the fluid bladder.
Figure 42:
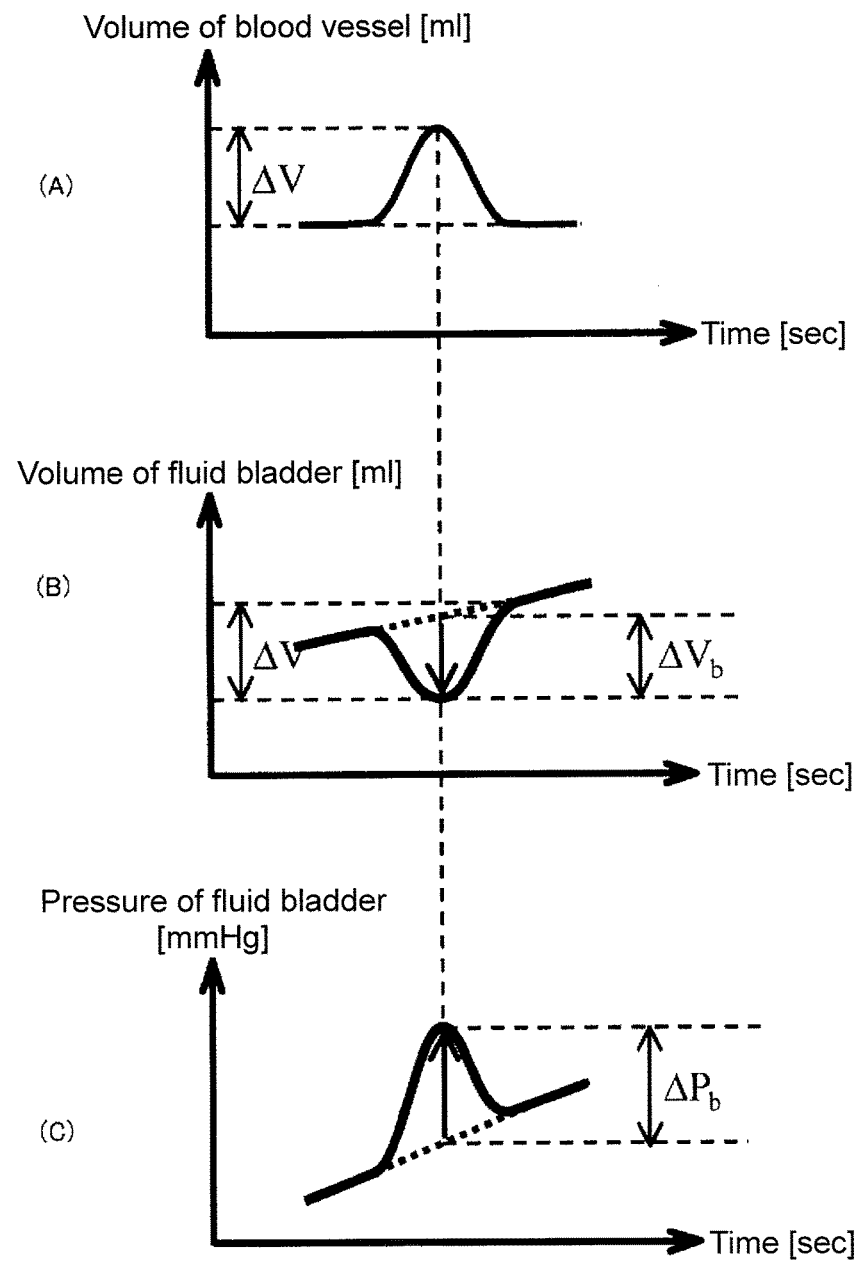
FIG. 42 is a diagram illustrating a volume change of a fluid bladder and a pressure change of the fluid bladder according to a volume change of a blood vessel when an inflow of a fluid flowing into the fluid bladder is slow, i.e., the amount of inflow per unit time is small, in the electronic sphygmomanometer for measuring the blood pressure during pressurizing process of the fluid bladder.
Figure 43A:
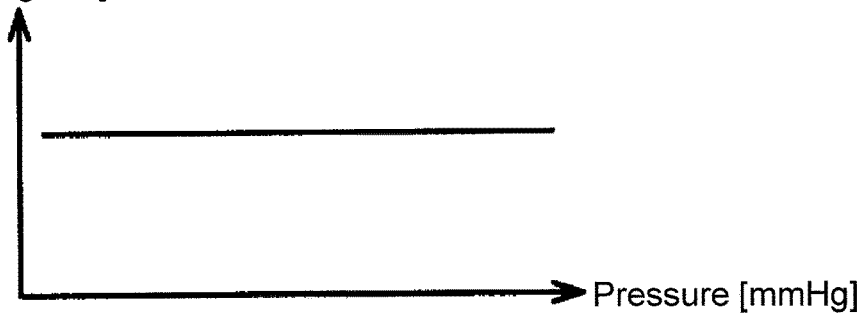
FIG. 43A is a diagram illustrating relationship between a pressure of a fluid bladder and a pressurizing rate in the sphygmomanometer for pressurizing the fluid bladder at a constant rate and measuring the blood pressure during pressurizing process.
Figure 43B:
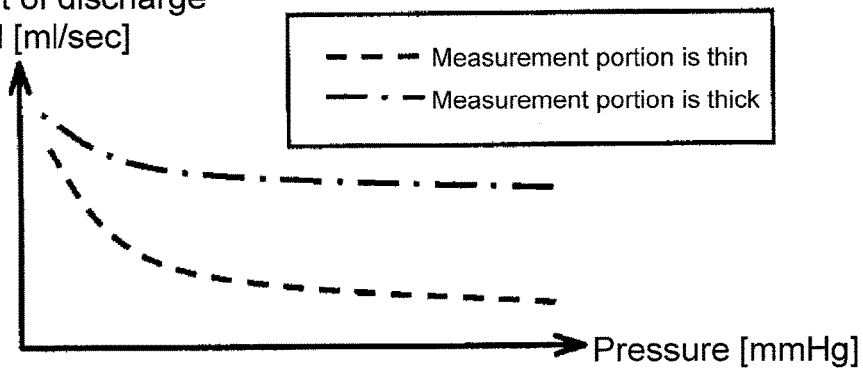
FIG. 43B is a diagram illustrating relationship between a pressure of a fluid bladder and the amount of inflow of a fluid into the fluid bladder per unit time in the sphygmomanometer for pressurizing the fluid bladder at a constant rate and measuring the blood pressure during pressurizing process.
Figure 43C:
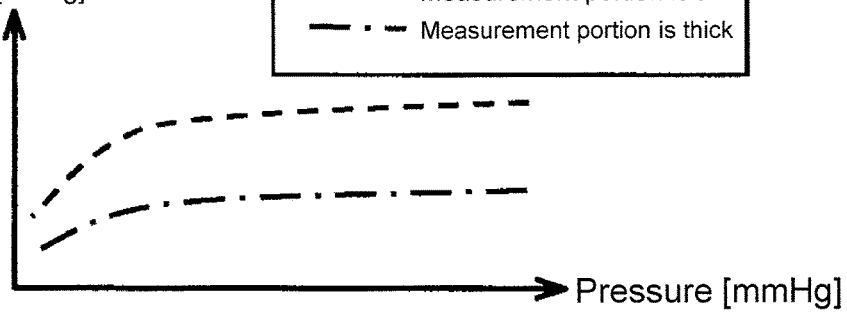
FIG. 43C is a diagram illustrating relationship between a pressure of a fluid bladder and a pressurized pulse wave amplitude value with respect to a constant volume change in the sphygmomanometer for pressurizing the fluid bladder at a constant rate and measuring the blood pressure during pressurizing process.
Figure 44A:
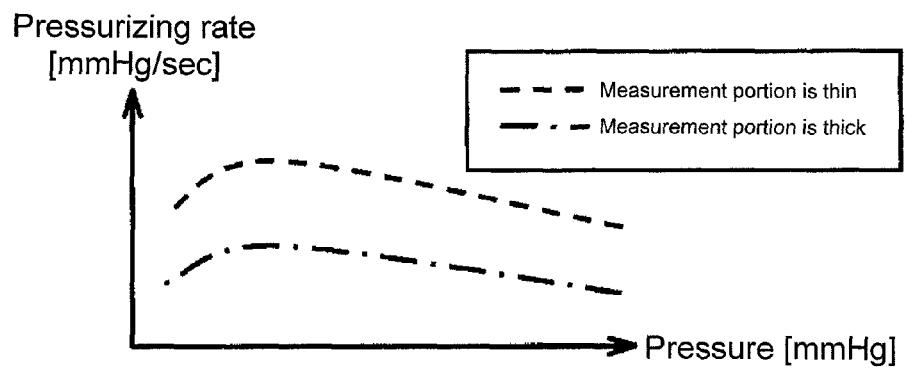
FIG. 44A is a diagram illustrating relationship between a pressure of a fluid bladder and a pressurizing rate in an electronic sphygmomanometer for measuring a blood pressure during pressurizing process of the fluid bladder with a constant drive voltage of a pump pressurizing the fluid bladder.
Figure 44B:
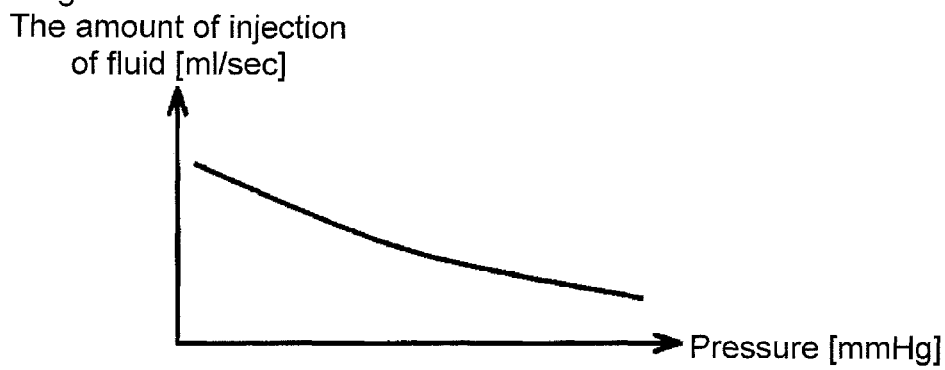
FIG. 44B is a diagram illustrating relationship between a pressure of a fluid bladder and the amount of inflow of a fluid into the fluid bladder per unit time in the electronic sphygmomanometer for measuring a blood pressure during pressurizing process of the fluid bladder with a constant drive voltage of a pump pressurizing the fluid bladder.
Figure 44C:
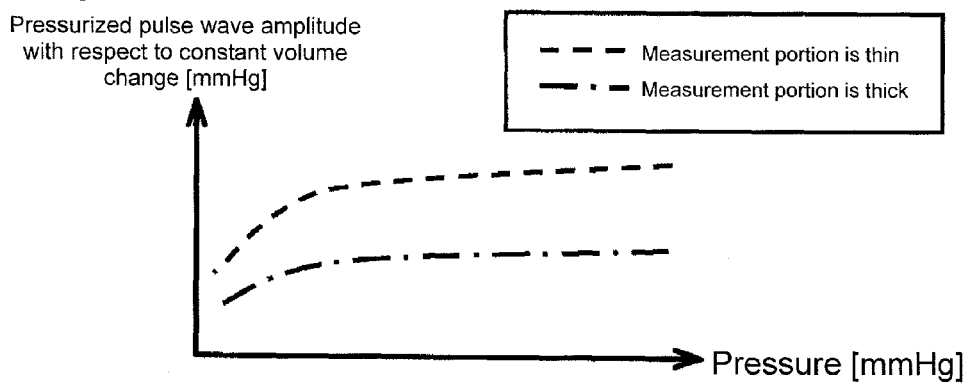
FIG. 44C is a diagram illustrating relationship between a pressure of a fluid bladder and a pressurized pulse wave amplitude value with respect to a constant volume change in the electronic sphygmomanometer for measuring a blood pressure during pressurizing process of the fluid bladder with a constant drive voltage of a pump pressurizing the fluid bladder.

FIG. 22 is a diagram illustrating relationship between a pressure of the fluid bladder 13 and a detected pulse wave amplitude. (A) shows a pressure change of the fluid bladder 13 according to an elapsed time and a pressure change of a pressure in an artery. In (A), a dotted line A represents a pressure change of the fluid bladder 13 in a case where the pressure of the fluid bladder is controlled to be pressurized with a constant rate in a conventional example. In contrast, in the sphygmomanometer 1' according to the present embodiment, a pressure change of the fluid bladder 13 is represented by a solid line B in a case where the drive voltage Ep is controlled to be updated and pressurized according to the internal pressure P, i.e., the pressure of the fluid bladder 13. In the sphygmomanometer 1', the drive voltage Ep of the pump 21 is updated according to the pressure of the fluid bladder 13 during pressurizing process. Accordingly, a pressure in an artery is measured as shown in (C), whereas in the conventional example, it is measured according to a (pressurizing) pressure change of the fluid bladder 13 as shown in (B). More specifically, in (C), a dotted line represents line segments obtained by connecting each measurement value of the pressure in the artery as shown in (B). As shown in FIGS. 39 and 40, in the conventional sphygmomanometer for controlling the pressure of the fluid bladder so as to pressurize the pressure of the fluid bladder with a constant rate, detection accuracy of a volume change of a blood vessel is lower in a region in which a fluid density of the fluid bladder is low than in a region in which the fluid density of the fluid bladder is high even when the pressure in the artery is the same. In contrast, as is evident from comparison between (B) and (C), the sphygmomanometer 1' according to the present embodiment has significantly improved detection accuracy of a volume change of a blood vessel in a region in which the pressure of the fluid bladder 13 is low, compared with the detection accuracy of the conventional sphygmomanometer for controlling the pressure of the fluid bladder so as to pressurize the pressure of the fluid bladder with a constant rate. Likewise, this indicates that detection accuracy of a volume change of a blood vessel is improved in a region in which the pressure is high.

Figure 23:
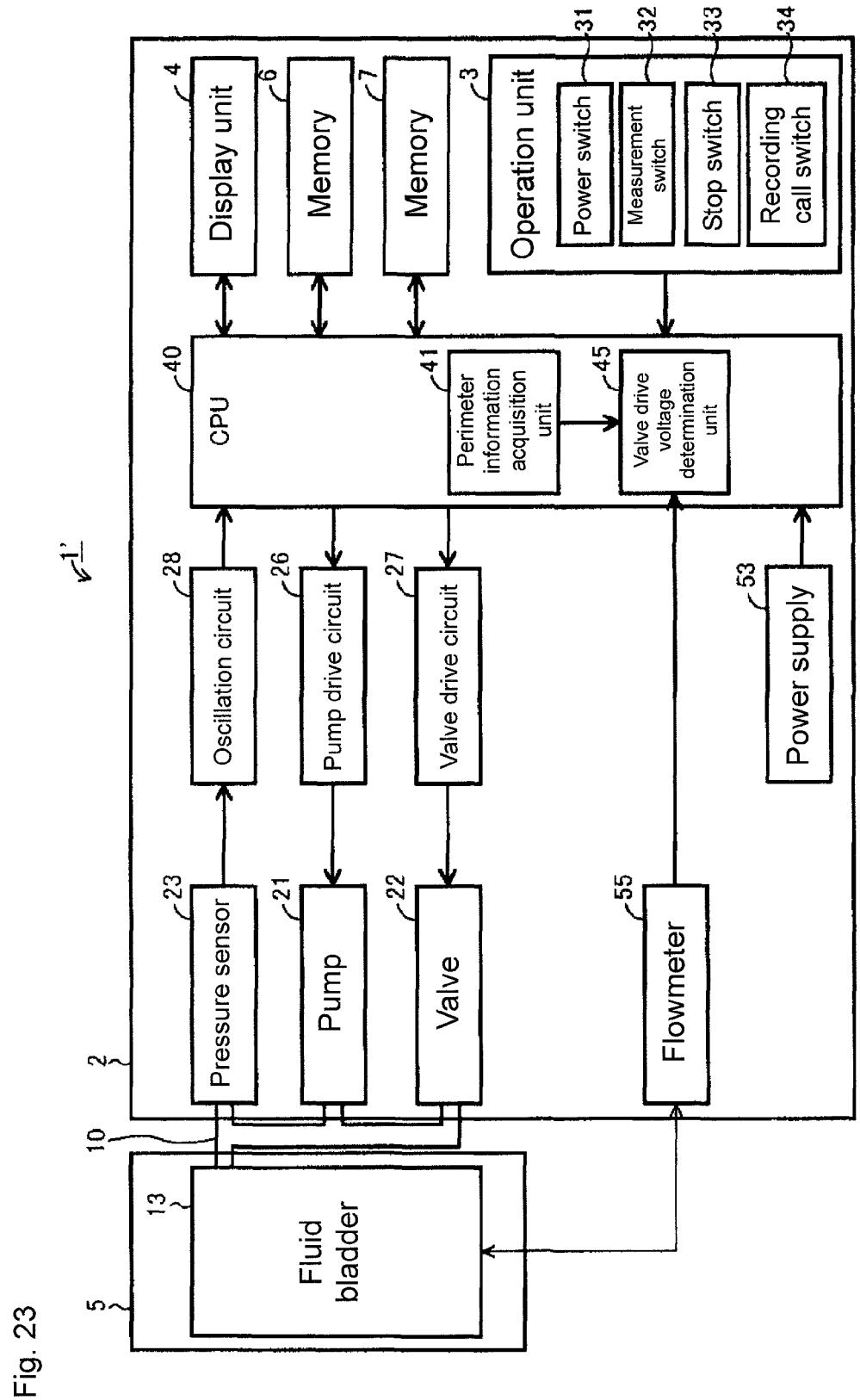
FIG. 23 is a block diagram illustrating another specific example of hardware configuration of a sphygmomanometer serving as a blood pressure measurement device according to the second embodiment.

In the above example, in the pressurizing process in step S403, the CPU 40 updates the drive voltage Ep based on the pressure of the fluid bladder 13. However, the sphygmomanometer 1' may further include a flowmeter 55 for measuring the amount of inflow of the fluid into the fluid bladder 13 as shown in FIG. 23 in addition to the constitution described above, and during pressurizing process, the pump drive voltage determination unit 45 may update the drive voltage Ep so as to maintain proportional relationship between the amount of inflow of the fluid into the fluid bladder 13 per unit time and the pressurizing rate. This also enables relationship between the amount of inflow of the fluid into the fluid bladder 13 per unit time and the pressurizing rate to be brought closer to proportional relationship. Therefore, the pressurized pulse wave amplitude with respect to a constant volume change of the blood vessel can be made almost constant, and the measurement accuracy can be improved.

[Modification]

Figure 24:
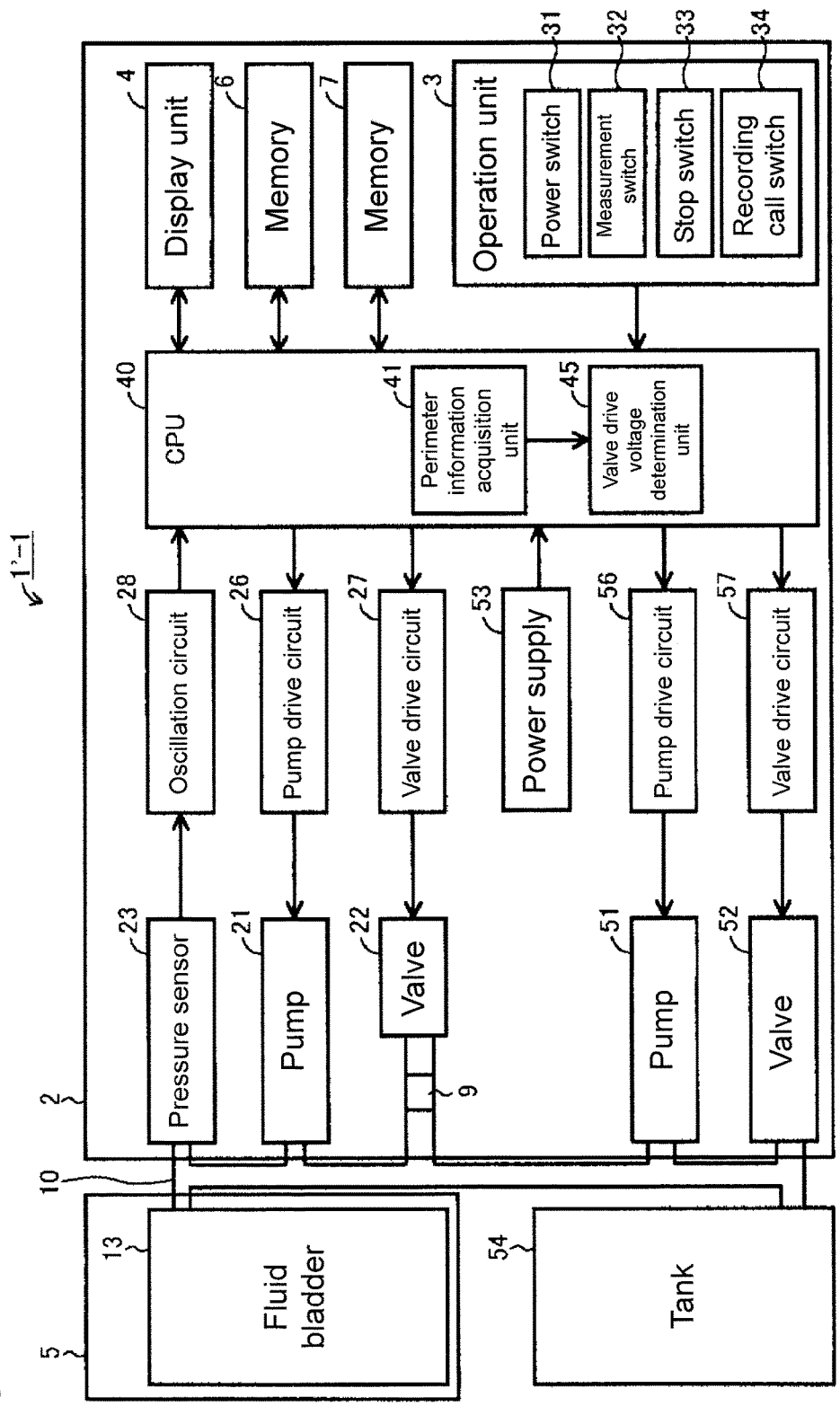
FIG. 24 is a block diagram illustrating a specific example of hardware configuration of a sphygmomanometer according to a modification of the second embodiment.

A hardware configuration of a sphygmomanometer 1'-1, i.e., a modification of the sphygmomanometer 1', will be described with reference to FIG. 24. The sphygmomanometer 1' has the same structure as the sphygmomanometer 1-1. More specifically, the sphygmomanometer 1'-1 will be described with reference to FIG. 24. The sphygmomanometer 1'-1 further includes a tank 54 storing a non-pressurized fluid and connected to the fluid bladder 13 via the tube 10, in addition to the hardware configuration of the sphygmomanometer 1' as shown in FIG. 16. The tank 54 is connected to the pump 51 and the valve 52. The pump 51 and the valve 52 are respectively connected to a pump drive circuit 56 and a valve drive circuit 57. Further, the pump drive circuit 56 and the valve drive circuit 57 are connected to the CPU 40. The CPU 40 executes a predetermined program stored in the memory 6 based on an operation signal inputted with the operation unit 3. The CPU 40 determines voltages for driving the pump 51 and the valve 52, and outputs control signals to the pump drive circuit 56 and the valve drive circuit 57 according to the determined voltages. When the pump 51 is driven, the non-pressurized fluid stored in the tank 54 flows into the fluid bladder 13 via the tube 10. When the valve 52 is driven, the non-pressurized fluid is discharged from the fluid bladder 13.

A filter 9 is arranged at a portion connecting between the fluid bladder 13 and the valve 22. The filter 9 is made of a material that allows the fluid to pass through but does not allow the non-pressurized fluid to pass through in order to prevent the non-pressurized fluid from leaking out of the valve 22 that injects the fluid into the fluid bladder 13 or discharges the fluid from the fluid bladder 13 when the non-pressurized fluid in the tank 54 moves to the fluid bladder 13.

A specific example of processing executed in response to an operation of the measurement switch 32 in the sphygmomanometer 1'-1 will be described with reference to a flowchart of FIG. 25. The processing shown in the flowchart of FIG. 25 is achieved by causing the CPU 40 to execute a predetermined program stored in the memory 6.

Figure 25:
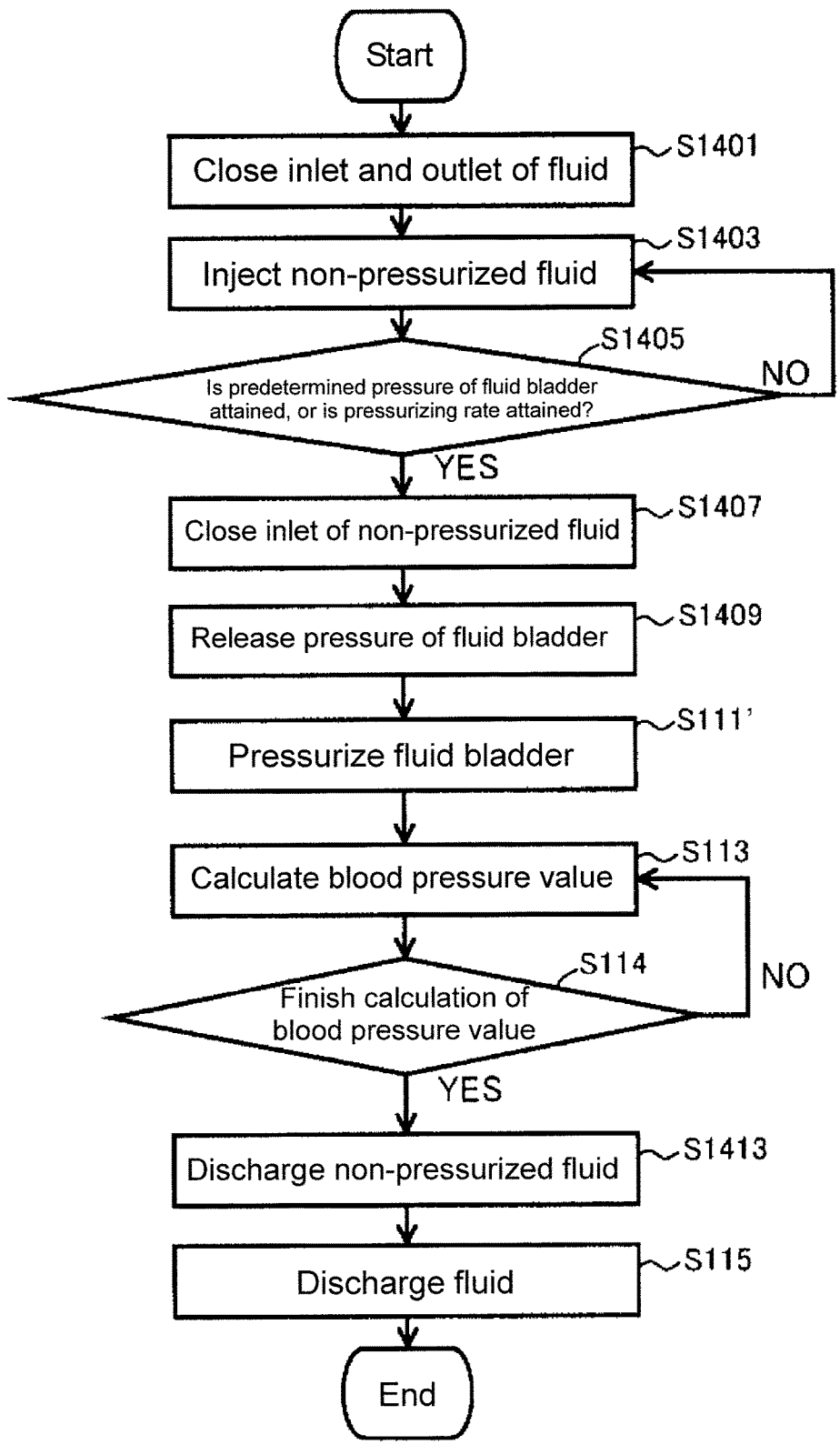
FIG. 25 is a flowchart illustrating a specific example of processing executed in response to an operation of the measurement switch on the sphygmomanometer according to the modification of the second embodiment.

Referring to FIG. 25, the sphygmomanometer 1' performs the same processings as those of the sphygmomanometer 1-1. More specifically, the same processings as those of the sphygmomanometer 1-1 are performed from steps S1401 to S1409. The non-pressurized fluid is caused to flow from the tank 54 into the fluid bladder 13 until the internal pressure of the fluid bladder 13 reaches a predetermined pressure. Thereafter, the inlet of the non-pressurized fluid into the fluid bladder 13 is closed, the valve 22 is opened, and the pressure of the fluid bladder 13 is released. Thereby, a predetermined amount of non-pressurized fluid is injected into the fluid bladder 13, and further, the internal pressure becomes atmospheric pressure.

Thereafter, the processing of step S111, which is similar to the processing according to the second embodiment, is executed. In step S113, the blood pressure value is calculated while the fluid bladder 13 is pressurized. When the sphygmomanometer 1'-1 finishes calculation of the blood pressure value (YES in step S114), the sphygmomanometer 1'-1 operates in the same manner as the sphygmomanometer 1-1 as follows. The CPU 40 outputs a control signal to the valve drive circuit 57 to open the valve 52 in step S1413, and discharges the non-pressurized fluid from the fluid bladder 13. Thereafter, in step S115, the valve 22 is opened according to a control signal given by the CPU 40, and the fluid is discharged from the fluid bladder 13.

In the same manner as the sphygmomanometer 1-1, the sphygmomanometer 1'-1 is characterized as follows. Before pressurizing the fluid bladder 13 in step S111, the sphygmomanometer 1'-1 injects a predetermined amount of non-pressurized fluid into the fluid bladder 13 to increase the volume of the fluid bladder 13, thereby reducing the volume of the fluid flowing into the fluid bladder 13. Accordingly, compared with the method for causing all the fluid to flow from an initial state, the sphygmomanometer 1'-1 reduces a volume change of the fluid bladder 13 in a region in which the pressure of the fluid bladder 13 is low as shown by portion A in FIG. 33, as described above with reference to FIG. 33. Therefore, in the sphygmomanometer 1'-1, the detection accuracy of the volume change of the blood vessel can be improved.

In the same manner as the sphygmomanometer 1-1, the sphygmomanometer 1'-1 may employ the methods as shown in FIG. 15A to 15C or a combination thereof in order to reduce the volume change of the volume change of the fluid bladder 13 in a low pressure region.

Further, the control of the sphygmomanometer 1' according to the second embodiment during pressurizing process and the constitution of the sphygmomanometer 1'-1 according to the modification may be combined. More specifically, the processing of step S101, not shown in FIG. 24, is performed in the processing of the sphygmomanometer 1'-1, in which the perimeter information acquisition unit 41 obtains the perimeter information, and the pump drive voltage determination unit 45 determines the control parameter Ap. Further, the processing of step S111 is executed instead of step S111', in which the pump drive voltage determination unit 45 determines the drive voltage Ep when the fluid bladder 13 is pressurized. Further, during pressurizing process in step S111, the pump drive voltage determination unit 45 may update the drive voltage Ep according to the internal pressure of the fluid bladder 13. Accordingly, relationship between the flow amount of the fluid injected into the fluid bladder 13 per unit time and the pressurizing rate of the fluid bladder 13 can be brought closer to proportional relationship. Accordingly, the detection accuracy of the volume change of the blood vessel can be made almost constant, and the detection accuracy can be improved.

Third Embodiment

When the above-described control is performed in the sphygmomanometer 1 according to the first embodiment, the internal pressure of the fluid bladder 13 changes in the depressurizing process as shown in FIG. 11(A). On the other hand, when the above-described control is performed in the sphygmomanometer 1' according to the second embodiment, the internal pressure of the fluid bladder 13 changes in the pressurizing process as shown in FIG. 22(A). As shown in both of FIGS. 11(A) and 22(A), the rate greatly changes at a high pressure side in these control methods. Therefore, in any of the cases, the number of pulse waves obtained at the high pressure side is small as shown in FIGS. 11(C) and 22(C). In other words, in any of the control methods, less pulse wave information can be obtained from the high pressure side than from the low pressure side.

Accordingly, in the third embodiment, the sphygmomanometer 1 and the sphygmomanometer 1' performs blood pressure measurement in both of the pressurizing process and the depressurizing process.

Figure 26:
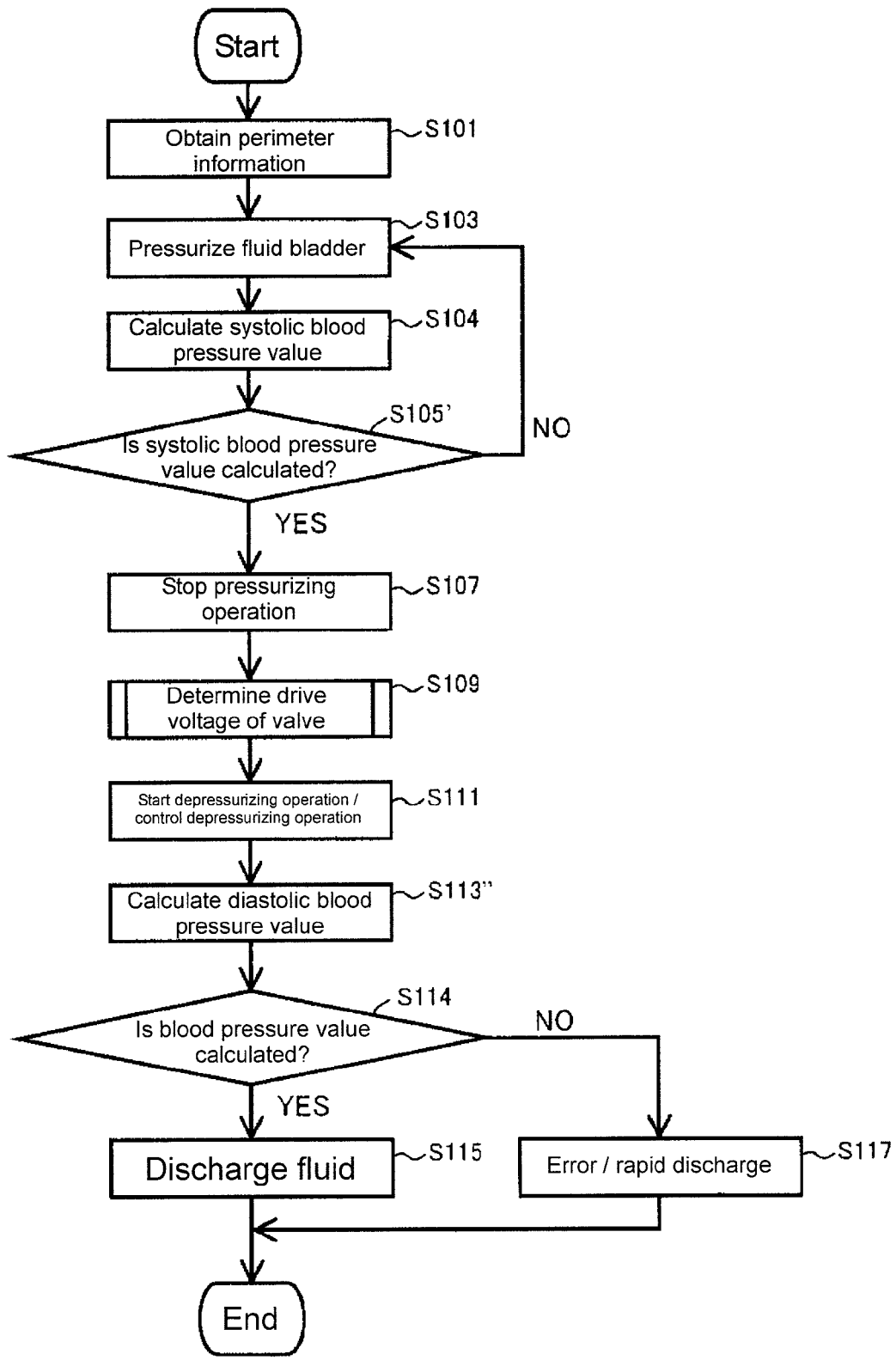
FIG. 26 is a flowchart illustrating a specific example of processing executed in response to an operation of the measurement switch on the sphygmomanometer according to the third embodiment.

First, the sphygmomanometer 1 will be described. A specific example of processing executed in response to an operation of the measurement switch 32 in the sphygmomanometer 1 according to the third embodiment will be described with reference to a flowchart of FIG. 26. When the third embodiment is compared with the processings of the first embodiment shown in FIG. 2 are compared, the difference is as follows. In the pressurizing process of the fluid bladder 13 in step S103, the CPU 40 extracts a vibrational component caused by a volume change of an artery, superposed on the internal pressure of the fluid bladder 13, from an output of the pressure sensor 23 in step S104, and calculates a systolic blood pressure value according to a predetermined calculation. It should be noted that the pressurizing process in step S103 may be an ordinary pressurizing process with a constant rate. Then, the systolic blood pressure value calculated in step S104 (YES in step S105'), and the processings of step S107 and subsequent steps are performed. In the third embodiment, the CPU 40 calculates a diastolic blood pressure value according to a predetermined calculation from an output of the pressure sensor 23 (step S113") in the processing of step S113, i.e., in the depressurizing process of the fluid bladder 13 in which the drive voltage Ev is controlled to be constant (that is, the gap of the valve 22 is constant) in step S111.

Figure 27:
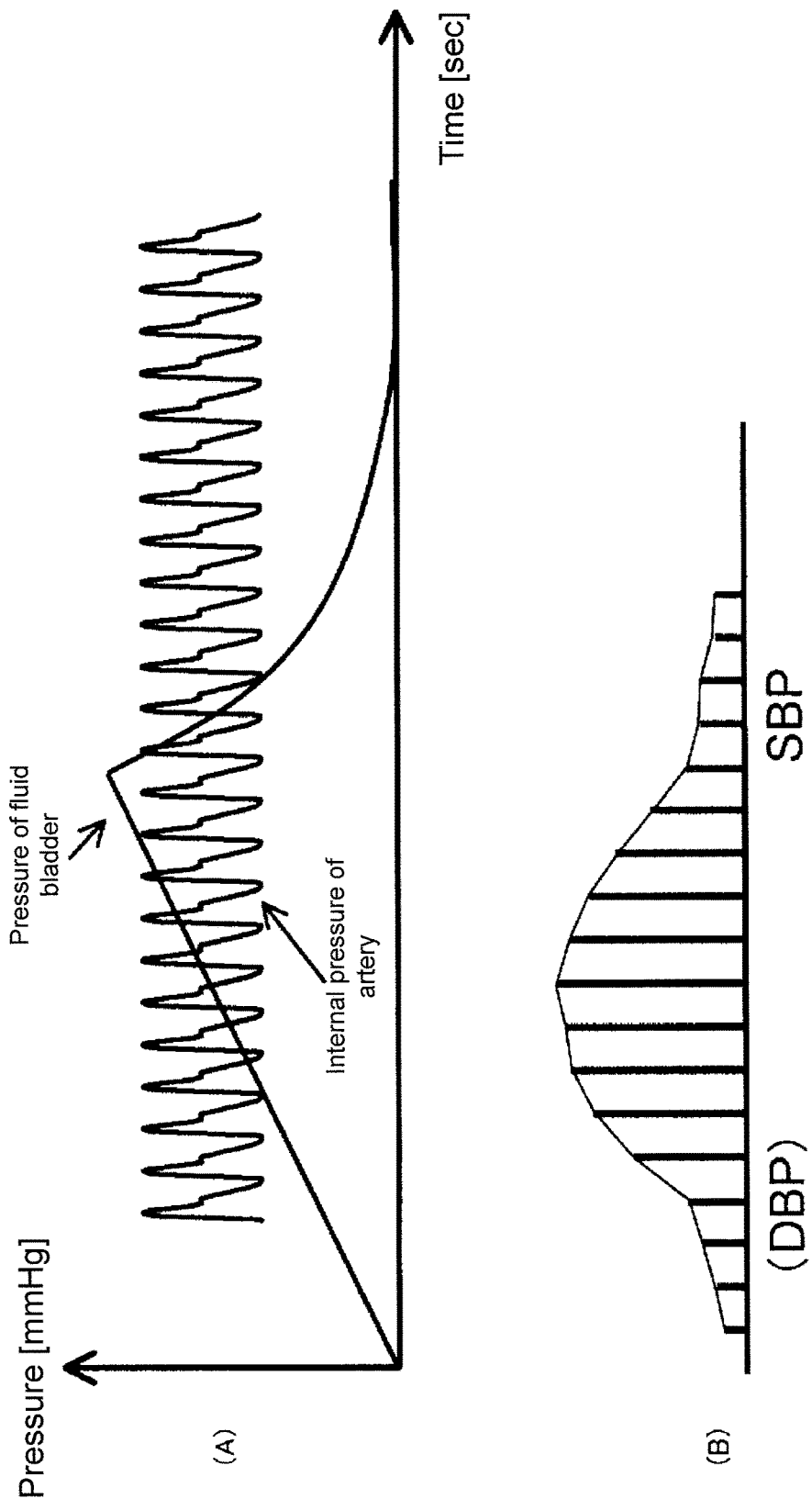
FIG. 27 is a diagram illustrating relationship between a pressure of a fluid bladder and a detected pulse wave amplitude.

FIG. 27 is a diagram illustrating relationship between a pressure of the fluid bladder 13 and a detected pulse wave amplitude. (A) shows a pressure change of the fluid bladder 13 according to an elapsed time and a pressure change of a pressure in an artery. (B) shows a pressure in an artery measured according to (pressurizing) pressure change of the fluid bladder 13 in step S104. The pressure in the artery measured in step S113" is the same as what is shown in FIG. 11(C).

Figure 28:
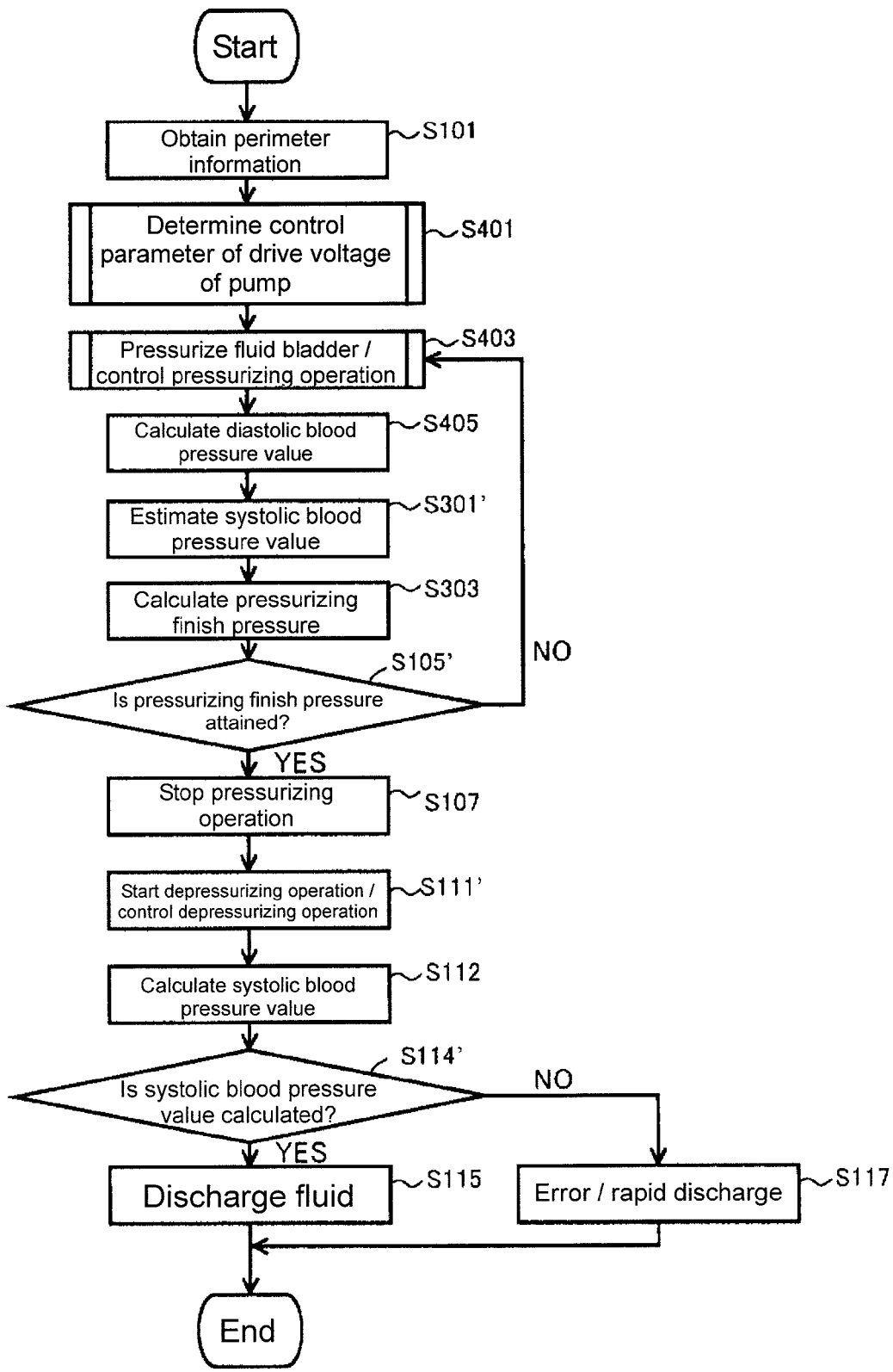
FIG. 28 is a flowchart illustrating a specific example of processing executed in response to an operation of the measurement switch on the sphygmomanometer according to the third embodiment.

Subsequently, the sphygmomanometer 1' will be described. A specific example of processing executed in response to an operation of the measurement switch 32 in the sphygmomanometer 1' according to the third embodiment will be described with reference to a flowchart of FIG. 28. When the third embodiment is compared with the processings of the second embodiment shown in FIG. 17, the difference is as follows. The same processings as those of the second embodiment are performed up to step S403. Thereafter, in the third embodiment, in the process in which the fluid bladder 13 is pressurized and controlled in step S403, the CPU 40 measures a pressure in an artery in step S405, and calculates a diastolic blood pressure value. In step S301', the CPU 40 estimates a systolic blood pressure value based on an internal pressure change of the fluid bladder 13 obtained from the pressure sensor 23, and in step S303, the CPU 40 calculates a pressure of the fluid bladder 13 at the end of the pressurizing process. Then, when the pressure of the fluid bladder 13 reaches the pressurizing finish pressure calculated in step S303 (YES in step S105'), the CPU 40 outputs a control signal to the pump drive circuit 26 in step S107, and stops pressurizing the fluid bladder 13. Thereafter, in step S111', an ordinary depressurizing process with a constant rate is executed. In the depressurizing process, the pressure in the artery is measured, and the systolic blood pressure value is calculated (step S112).

Figure 29:
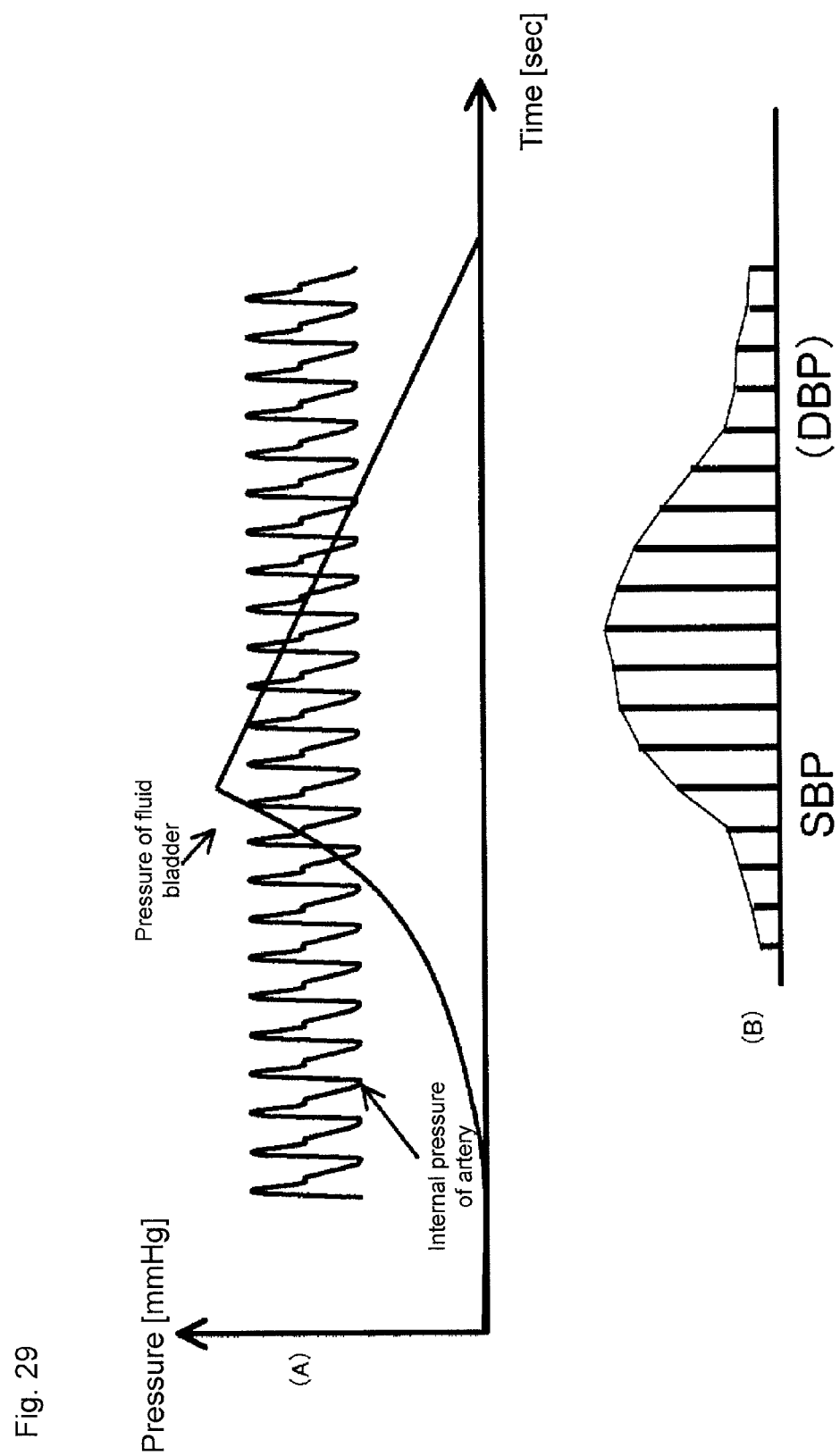
FIG. 29 is a diagram illustrating relationship between a pressure of a fluid bladder and a detected pulse wave amplitude.

FIG. 29 is a diagram illustrating relationship between a pressure of the fluid bladder 13 of the sphygmomanometer 1' and a detected pulse wave amplitude according to the third embodiment. (A) shows a pressure change of the fluid bladder 13 according to an elapsed time and a pressure change of a pressure in an artery. (B) shows a pressure in an artery measured according to (depressurizing) pressure change in depressurizing process of the fluid bladder 13. The pressure in the artery measured in the pressurizing process is the same as what is shown in (C) of FIG. 22.

As can be understood from the comparison between (B) of FIG. 27 and (C) of FIG. 11, the sphygmomanometer 1 measures the pressure in the artery in step S104. Therefore, the number of pulse waves obtained from the high pressure side increases, compared with the case where the pressure in the artery is measured in step S113 or step 113". As can be understood from the comparison between (B) of FIG. 29 and (C) of FIG. 22, the sphygmomanometer 1' measures the pressure in the artery in the depressurizing process. Therefore, the number of pulse waves obtained from the high pressure side increases, compared with the case where the pressure in the artery is measured in pressurizing process. In other words, the sphygmomanometers 1, 1' measure the pressure in the artery according to the measurement method of the third embodiment and calculates the blood pressure value. Therefore, more artery information can be obtained from the high pressure side, compared with the measurement according to the measurement method of the first embodiment or the measurement method of the second embodiment. As a result the measurement accuracy of the systolic blood pressure can be improved. Therefore, when the control described in the first embodiment and the above control are performed in the sphygmomanometer 1, not only detection accuracy of a volume change of a blood vessel in a region in which the pressure of the fluid bladder 13 is low but also detection accuracy of a volume change of a blood vessel in a region in which the pressure of the fluid bladder 13 is high can be improved. Likewise, when the control described in the second embodiment and the above control are performed in the sphygmomanometer 1', not only detection accuracy of a volume change of a blood vessel in a region in which the pressure of the fluid bladder 13 is low but also detection accuracy of a volume change of a blood vessel in a region in which the pressure of the fluid bladder 13 is high can be improved.

Fourth Embodiment

Figure 30:
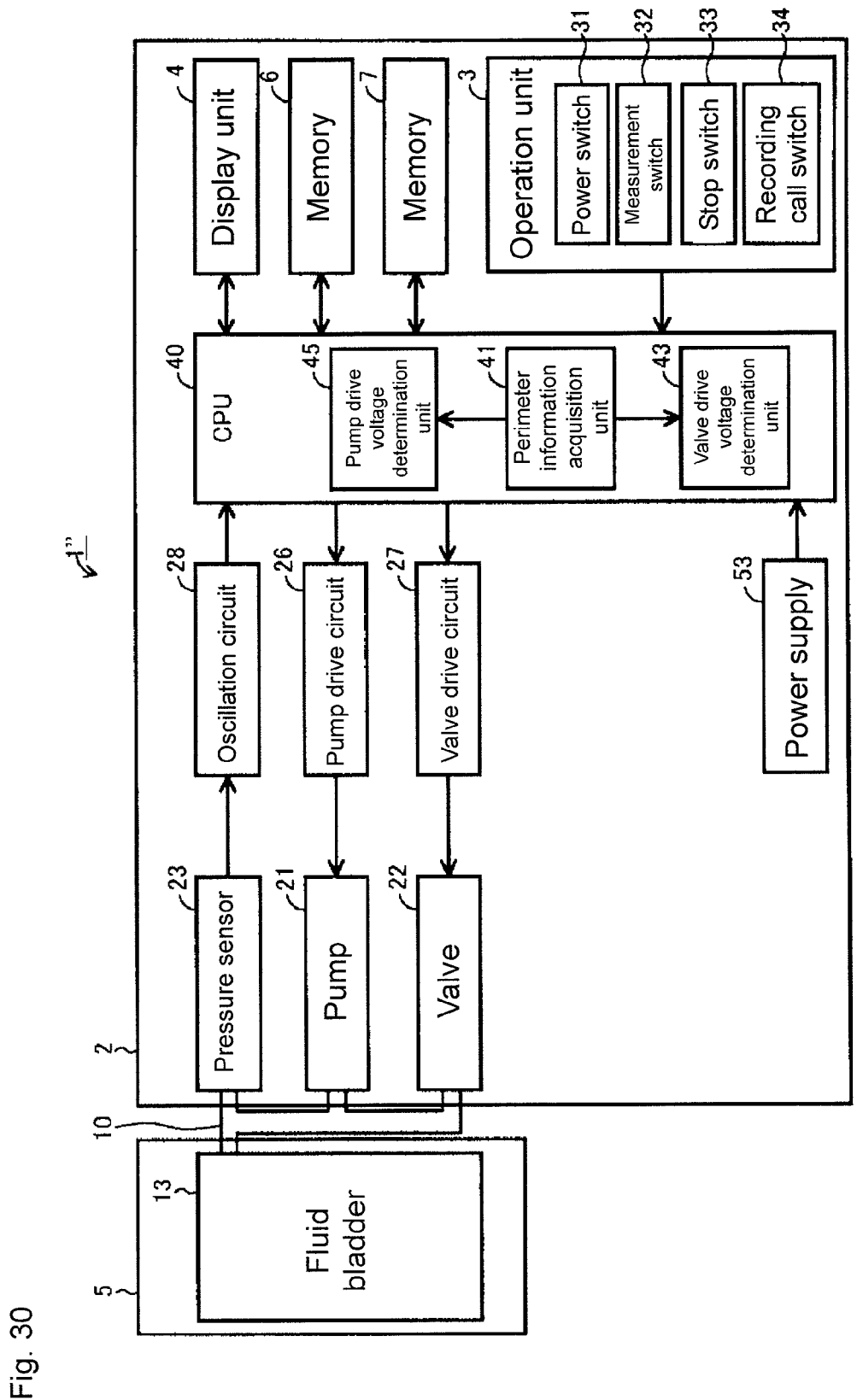
FIG. 30 is a block diagram illustrating a specific example of hardware configuration of a sphygmomanometer serving as a blood pressure measurement device according to the fourth embodiment.

Further, the control described in the second embodiment may be performed during the pressurizing process of the fluid bladder 13, and the control described in the first embodiment may be performed during the depressurizing process. As shown in FIG. 30, a CPU 40 of a sphygmomanometer 1" serving as a blood pressure measurement device according to the fourth embodiment includes the valve drive voltage determination unit 43 described in the first embodiment and the pump drive voltage determination unit 45 described in the second embodiment.

Figure 31:
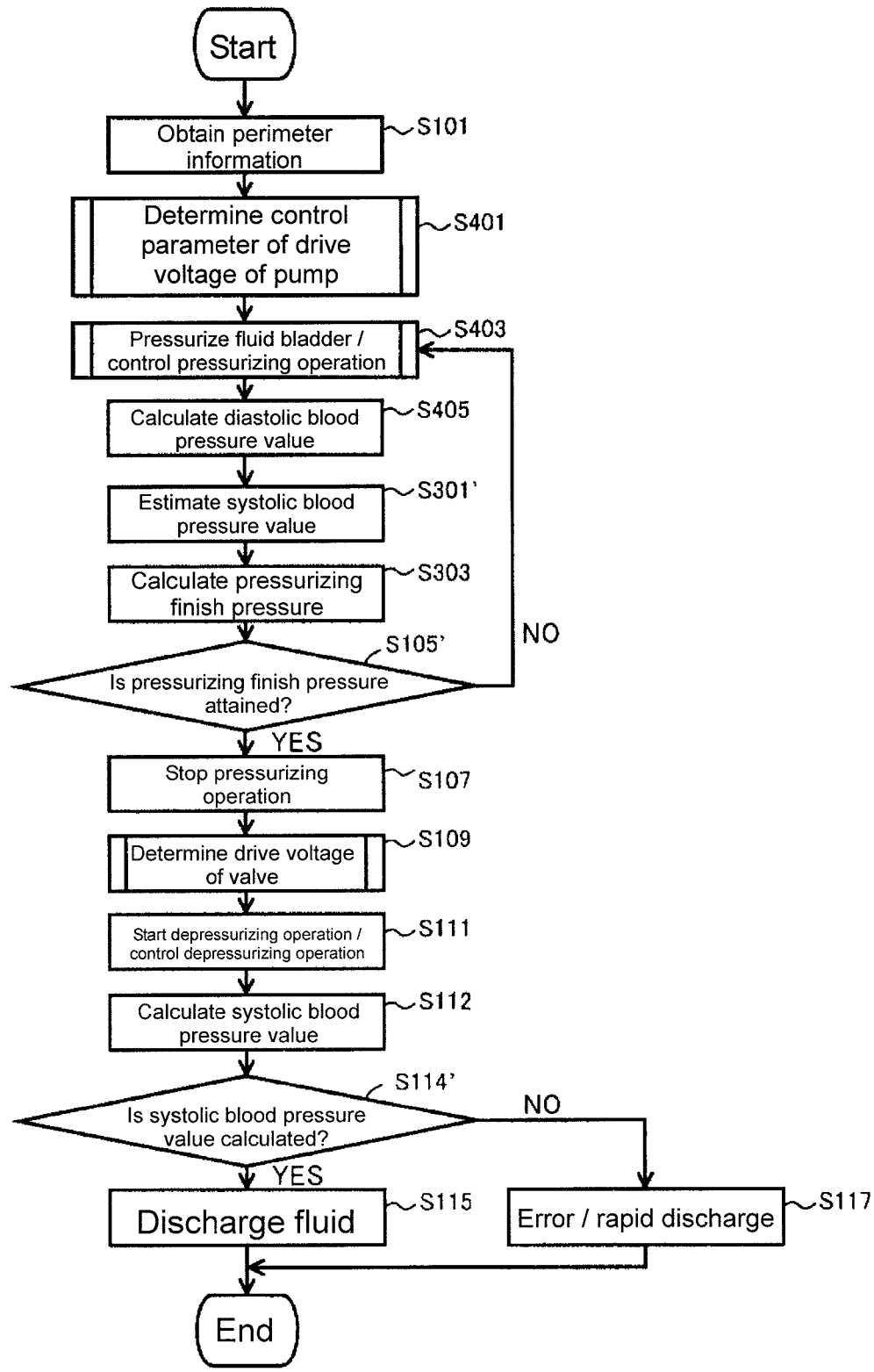
FIG. 31 is a flowchart illustrating a specific example of processing executed in response to an operation of the measurement switch on the sphygmomanometer according to the fourth embodiment.

A specific example of processing executed in response to an operation of the measurement switch 32 in the sphygmomanometer 1" will be described with reference to a flowchart of FIG. 31. The processing shown in the flowchart of FIG. 31 is a combination of the processing shown in the flowchart of FIG. 2, the processing shown in the flowchart of FIG. 8, and the processing shown in the flowchart of FIG. 17 described above. As described in the third embodiment, this processing is to measure a pressure in an artery in any of pressurizing process and depressurizing process of the fluid bladder 13 and calculate a blood pressure value.

More specifically, description will be made with reference to FIG. 31. In step S101, the perimeter information acquisition unit 41 of the CPU 40 obtains perimeter information representing a perimeter of a measurement portion, i.e., a size of the measurement portion. In step S401, the pump drive voltage determination unit 45 of the CPU 40 determines a control parameter Ap for controlling a drive voltage Ep of a pump 21 based on the perimeter information obtained in step S101. Then, in step S403, the CPU 40 uses the internal pressure P and the control parameter Ap determined in step S401 to determine the drive voltage Ep. The CPU 40 outputs a control signal for driving the pump 21 with the determined drive voltage Ep to the pump drive circuit 26, thereby pressurizing the fluid bladder 13. The processings up to this step are the same as the processings of the second embodiment described using the flowchart of FIG. 17.

In the fourth embodiment, in the process in which the fluid bladder 13 is pressurized and controlled in step S403, the CPU 40 measures a pressure in an artery in step S405, and calculates a diastolic blood pressure value. This processing is the same as the processing of the third embodiment. In the fourth embodiment, in step S301', the CPU 40 estimates a systolic blood pressure value based on an internal pressure change of the fluid bladder 13 obtained from the pressure sensor 23, and in step S303, the CPU 40 calculates a pressure of the fluid bladder 13 at the end of the pressurizing process. Then, when the pressure of the fluid bladder 13 reaches the pressurizing finish pressure calculated in step S303 (YES in step S105'), the CPU 40 outputs a control signal to the pump drive circuit 26 in step S107, and stops pressurizing the fluid bladder 13. The processings up to this step are the same as the processings of the modification of the first embodiment described using the flowchart of FIG. 8.

Subsequently, in step S109, the valve drive voltage determination unit 43 of the CPU 40 determines the drive voltage Ev of the valve 22 based on the perimeter information obtained in step S101. In step S111, the CPU 40 outputs a control signal to the valve drive circuit 27 so as to drive the valve 22 while maintaining the drive voltage Ev determined in step S109, and starts depressurizing the fluid bladder 13. The processings up to this step are the same as the processings of the first embodiment described using the flowchart of FIG. 2.

In the fourth embodiment, in the process in which the fluid bladder 13 is depressurized and controlled in step S111, the CPU 40 measures a pressure in an artery in step S112, and calculates a systolic blood pressure value. As described in the third embodiment, in the process for performing depressurizing control described in the first embodiment, a rate greatly changes at a high pressure side as shown in (A) of FIG. 11, and the number of pulse waves obtained from the high pressure side is small as shown in (C) of FIG. 11. Accordingly, in the fourth embodiment, in step S109, a drive voltage Ev is determined to make a smaller gap than a gap when the valve 22 is driven by the drive voltage Ev determined in step S109 of the processing in the first embodiment, so as to prevent a depressurizing rate from increasing at a high pressure side during the depressurizing process in step S111, i.e., prevent rapid depressurizing of the fluid bladder 13 at the high pressure side. More specifically, in the first embodiment, when both of the systolic blood pressure value and the diastolic blood pressure are calculated during the depressurizing process, the gap has such magnitude that achieves a depressurizing rate such that the number of pulses detected between the systolic blood pressure and the diastolic blood pressure is equal to or more than a predetermined number, for example. In the fourth embodiment, the gap has such magnitude that achieves a depressurizing rate such that the number of pulses detected in a predetermined range generally including the systolic blood pressure value but not including the diastolic blood pressure value during depressurizing process is equal to or more than a predetermined number. In the fourth embodiment, depressurizing rates may be stored to the memory 6 in advance in the same manner as the first embodiment. In the fourth embodiment, a drive voltage Ev may be determined upon storing, to the memory 6, coefficients α, β of the above expression (1) according to the depressurizing rate. Alternatively, in the fourth embodiment, the coefficients α, β stored in the memory 6 described in the first embodiment may be different by a predetermined ratio, and such coefficients may be used.

Further, in the fourth embodiment, when the systolic blood pressure value is calculated in step S112 (YES in step S114'), the valve 22 is opened according to a control signal given by the CPU 40 in step S115, so that the fluid is discharged from the fluid bladder 13.

Figure 32:
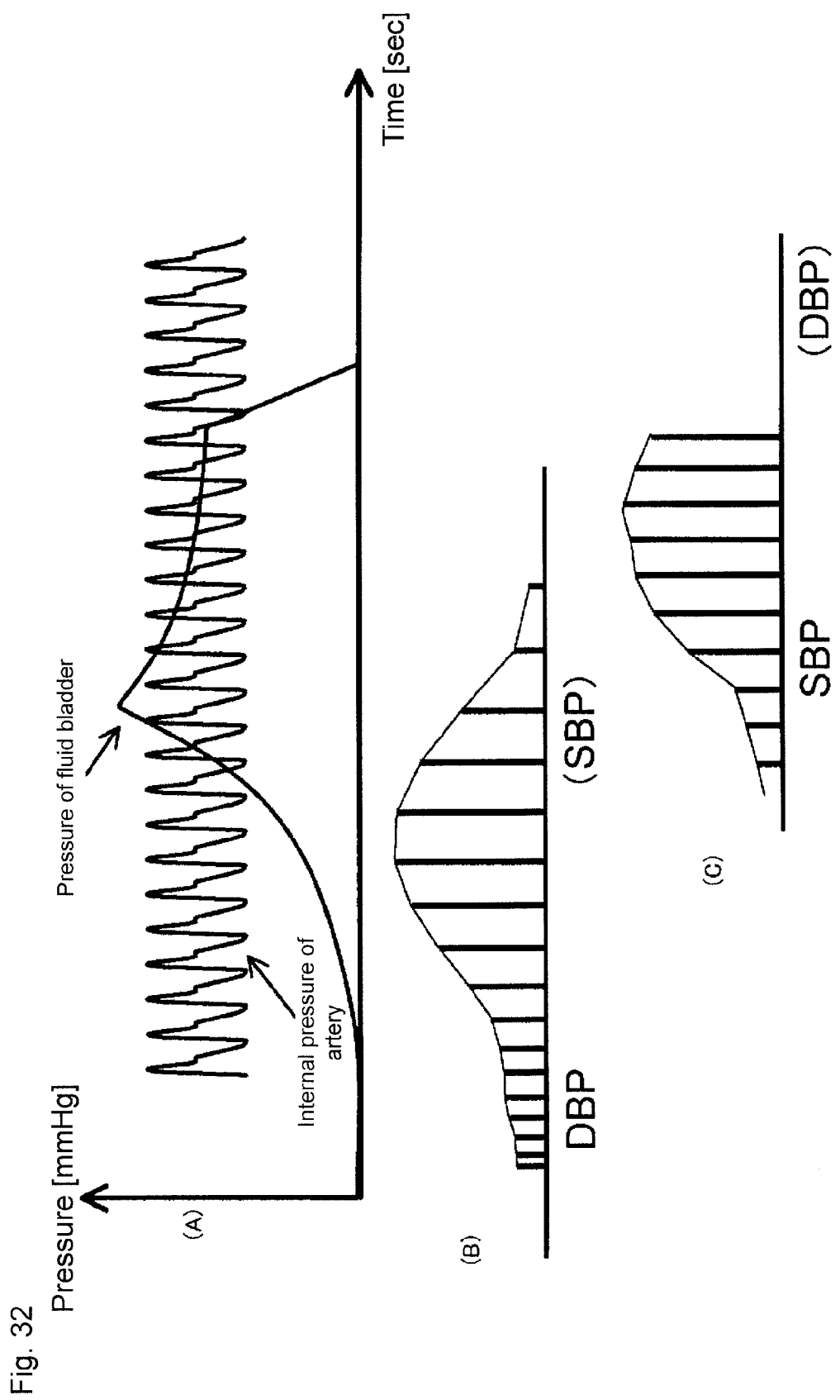
FIG. 32 is a diagram illustrating relationship between a pressure of a fluid bladder and a detected pulse wave amplitude.

FIG. 32 is a diagram illustrating relationship between a pressure of the fluid bladder 13 and a detected pulse wave amplitude. (A) shows a pressure change of the fluid bladder 13 according to an elapsed time and a pressure change of a pressure in an artery. (B) shows a pressure in an artery measured according to (pressurizing) pressure change of the fluid bladder 13 in step S405. (C) shows a pressure in an artery measured according to (depressurizing) pressure change of the fluid bladder 13 in step S112.

In the pressurizing process of the fluid bladder 13, the sphygmomanometer 1" according to the fourth embodiment performs the control for pressurizing the fluid bladder 13 while updating the drive voltage Ep according to the internal pressure P of the fluid bladder 13 described in the second embodiment. Accordingly, as described above, detection accuracy of a volume change of a blood vessel can be improved especially in a region in which the pressure of the fluid bladder 13 is low. In other words, as shown in (A), the increase of the pressure at the low pressure side is moderate, and as shown in (B), the number of pulse waves detected from that region is large. Therefore, a highly accurate diastolic blood pressure value can be obtained by calculating a diastolic blood pressure value from a pressure in an artery measured at the low pressure side of pressurizing process.

Further, the sphygmomanometer 1" according to the fourth embodiment executes the processing described in the modification of the first embodiment, in which the systolic blood pressure value is estimated based on the pressure in the artery measured in the pressurizing process of the fluid bladder 13, and the pressurizing process is finished when the pressure of the fluid bladder 13 reaches the pressure according to the estimated systolic blood pressure value. It should be noted that in the fourth embodiment, this processing may not be performed. Instead, an ordinary processing for pressurizing the fluid bladder 13 to achieve a previously defined pressure may be performed regardless of the systolic blood pressure value. However, when the above processing is performed, the pressure for pressurizing the fluid bladder 13 for measurement during depressurizing process can be reduced to a level lower than the pressure for pressurizing the fluid bladder 13 to achieve a previously defined pressure regardless of the systolic blood pressure value. Further, when compared with the method for pressurizing the fluid bladder 13 to achieve a previously defined pressure regardless of the systolic blood pressure value, the pressurizing time can be reduced, and the overall time needed for blood pressure measurement can be reduced. Therefore, the burden placed on a subject can be reduced.

Further, in the depressurizing process of the fluid bladder 13, the sphygmomanometer 1" according to the fourth embodiment performs control to keep a constant drive voltage Ev, i.e., keep a constant gap of the valve 22, as described in the first embodiment. Accordingly, as described above, detection accuracy of a volume change of a blood vessel can be improved especially in a region in which the pressure of the fluid bladder 13 is low. Further, in the fourth embodiment, as described above, the drive voltage Ev is controlled to be a constant voltage value making a smaller gap, compared with the case where the valve 22 is driven by the voltage value determined in step S109 of the processing of the first embodiment. Therefore, as shown in (A), the decrease of the pressure at the high pressure side is moderate, and as shown in (C), the number of pulse waves detected from that region is large. Therefore, a highly accurate diastolic blood pressure value can be obtained by calculating a systolic blood pressure value from a pressure in an artery measured at the high pressure side of depressurizing process.

Further, as described above, the sphygmomanometer 1" according to the fourth embodiment already obtains the diastolic blood pressure value in the pressurizing process. Accordingly, as soon as the systolic blood pressure value is obtained in the depressurizing process, the fluid is rapidly discharged from the fluid bladder 13, and the measurement processing can be terminated. Therefore, when compared with the method for obtaining the systolic blood pressure value and the diastolic blood pressure value in the depressurizing process, the depressurizing time can be reduced, and the overall time needed for blood pressure measurement can be reduced. Therefore, the burden placed on a subject can be reduced.

It is to be understood that the embodiments disclosed herein are examples in all respects and are not restrictive. While the invention has been described with respect to a limited number of embodiments, those skilled in the art, having benefit of this disclosure, will appreciate that other embodiments can be devised which do not depart from the scope of the invention as disclosed herein. It is to be understood that the scope of the present invention is defined not by the above described explanations, but by the claims, and includes meanings equivalent to the claims and all the modifications and variations within the scope.

DESCRIPTION OF SYMBOLS 1, 1-1, 1', 1'-1, 1" Sphygmomanometer
2 Main body
3 Operation unit
4 Display unit
5 Cuff
6,7 Memory
9 Filter
10 Tube
13 Fluid bladder
31 Power switch
21,51 Pump
22,52 Valve
23 Pressure sensor
26,56 Pump drive circuit
27,57 Valve drive circuit
28 Oscillation circuit
32 Measurement switch
33 Stop switch
34 Recording call switch
40 CPU
41 Perimeter information acquisition unit
43 Valve drive voltage determination unit
45 Pump drive voltage determination unit
53 Power supply
54 Tank
55 Flowmeter

The invention claimed is:

1. A blood pressure measurement device comprising:
a fluid bladder;
a pressurizing unit for pressurizing the fluid bladder by injecting a fluid into the fluid bladder;
a depressurizing unit for depressurizing the fluid bladder by discharging the fluid from the fluid bladder;
a sensor for measuring an internal pressure change of the fluid bladder;
a blood pressure measurement unit for calculating a blood pressure value based on the internal pressure change of the fluid bladder obtained by the sensor in the depressurizing process in which the depressurizing unit discharges the fluid from the fluid bladder; and
a control unit for controlling the pressurizing unit, the depressurizing unit, and the blood pressure measurement unit,
wherein the depressurizing unit includes only one valve arranged on the fluid bladder, so that a gap of an opening on the fluid bladder is controlled by the one valve,
wherein the gap of the one valve is controlled by a drive voltage,
wherein the control unit includes an acquisition unit for obtaining information about a perimeter of a measuring portion,
wherein the control unit determines the drive voltage of the one valve according to the perimeter so that the gap is set to a constant determined gap with respect to the obtained perimeter,
wherein the control unit controls the gap of the one valve to be maintained constant at the constant determined gap during the depressurizing process, resulting in rapid deflation at a beginning of the depressurizing process and slow deflation at an end of the depressurizing process, and
wherein the constant determined gap changes relatively to the perimeter such that the constant determined gap becomes great as the perimeter becomes large.

2. The blood pressure measurement device according to claim 1, wherein the control unit determines the gap of the one valve such that the internal pressure of the fluid bladder attains a depressurizing rate in which a predetermined number of more pulses are included in a time varying from a systolic blood pressure to a diastolic blood pressure.

3. The blood pressure measurement device according to claim 1,
wherein the blood pressure measurement unit further calculates a blood pressure value based on the internal pressure change of the fluid bladder obtained by the sensor in the pressurizing process in which the pressurizing unit injects the fluid into the fluid bladder, and
wherein the control unit determines the gap of the one valve according to the blood pressure value calculated based on the internal pressure change of the fluid bladder in the pressurizing process.

4. The blood pressure measurement device according to claim 1,
wherein the blood pressure measurement unit further calculates a cycle of a pulse wave based on the internal pressure change of the fluid bladder obtained by the sensor in the pressurizing process in which the pressurizing unit injects the fluid into the fluid bladder, and
wherein the control unit determines the gap of the one valve according to the cycle of the pulse wave calculated based on the internal pressure change of the fluid bladder in the pressurizing process.

5. The blood pressure measurement device according to claim 1, further comprising:
a measurement unit for measuring an amount of discharge,
wherein the control unit controls the amount of discharge of the fluid discharged by the depressurizing unit so as to achieve a proportional relationship between the amount of discharge and the depressurizing rate of the fluid bladder in the depressurizing process, based on the amount of discharge measured by the measurement unit and the internal pressure change of the fluid bladder obtained by the sensor.

6. The blood pressure measurement device according to claim 1, further comprising:
an increasing unit for increasing a volume of the fluid bladder,
wherein the pressurizing unit pressurizes the fluid bladder by injecting the fluid into the fluid bladder whose volume has been increased by the increasing unit.

* * * * *